US008492537B2

(12) United States Patent
Fahrig et al.

(10) Patent No.: US 8,492,537 B2
(45) Date of Patent: *Jul. 23, 2013

(54) NUCLEOSIDES FOR SUPPRESSING OR REDUCING THE DEVELOPMENT OF RESISTANCE IN CYTOSTATIC THERAPY

(75) Inventors: Rudolf Fahrig, Dresden (DE); Dieter Lohmann, Radebeul (DE); Andreas Rolfs, Eisenach (DE); Henrik Dieks, Berlin (DE); Janek Teubner, Berlin (DE); Jorg-Christian Heinrich, Dresden (DE)

(73) Assignee: RESprotect GmbH, Dresden (DE)

( * ) Notice: Subject to any disclaimer, the term of this patent is extended or adjusted under 35 U.S.C. 154(b) by 574 days.

This patent is subject to a terminal disclaimer.

(21) Appl. No.: 12/377,239

(22) PCT Filed: Aug. 13, 2007

(86) PCT No.: PCT/EP2007/007147
§ 371 (c)(1),
(2), (4) Date: Apr. 23, 2009

(87) PCT Pub. No.: WO2008/017515
PCT Pub. Date: Feb. 14, 2008

(65) Prior Publication Data
US 2010/0227834 A1 Sep. 9, 2010

(30) Foreign Application Priority Data

Aug. 11, 2006 (DE) .......................... 10 2006 037 786

(51) Int. Cl.
*C07H 19/00* (2006.01)
*C07H 19/048* (2006.01)
(52) U.S. Cl.
USPC ........................................ 536/28.1; 536/28.2
(58) Field of Classification Search
USPC ............................................... 536/28.1, 28.2
See application file for complete search history.

(56) References Cited

U.S. PATENT DOCUMENTS

| 4,544,740 | A | 10/1985 | Szabolcs née Borbás et al. |
| 4,724,232 | A | 2/1988 | Rideout et al. |
| 6,589,941 | B1 | 7/2003 | Fahrig et al. |
| 2004/0127454 | A1 | 7/2004 | Fahrig et al. |
| 2006/0178338 | A1 | 8/2006 | Fahrig et al. |

FOREIGN PATENT DOCUMENTS

| DD | 288 827 A5 | 4/1991 |
| DE | 32 33 198 A1 | 3/1983 |
| DE | 195 45 892 A1 | 6/1997 |
| DE | 101 08 851 A1 | 9/2002 |
| DE | 699 00 841 T2 | 10/2002 |
| EP | 0 097 039 A | 12/1983 |
| EP | 0 104 857 A | 4/1984 |
| EP | 0 368 668 A2 | 5/1990 |
| EP | 0 806 956 B1 | 8/2002 |
| JP | 62-103100 A | 5/1987 |
| NL | 8100177 A | 8/1982 |
| WO | WO 90/15064 A | 12/1990 |
| WO | WO 96/23506 A | 8/1996 |
| WO | WO 98/42351 A | 10/1998 |
| WO | WO 99/37753 A1 | 7/1999 |
| WO | WO 0232920 | * 4/2002 |
| WO | WO 02/39952 A | 5/2002 |
| WO | WO 02/39952 A2 | 5/2002 |
| WO | WO 2004/084917 A | 10/2004 |
| WO | WO 2005/012327 A | 2/2005 |

OTHER PUBLICATIONS

Wittek, et al., Effects of (E)-5-(2-Bromovinyl)-2'-Deoxyuridine on Proliferation of Human Fibroblasts, Peripheral Blood Mononuclear Cells, and Granulocyte-Monocyte Progenitor Cells in Vitro, Antimicrobial Agents and Chemotherapy, 1983, 24, 803-806.*
Lavandera et al., Nucleosides, Nucleotides & Nucleic Acids, 2003, 22, pp. 833-836.*
Mendiratta et al., J. Chem. Inf. Comput. Sei. 1994, 34, 867-871.*
Thornber, C. W., Chem. Soc. Rev., 1979, 8, 563-580.*
Han et al., AAPS Pharmsci 2000; 2 (1) article 6 (http://www.pharmsci.org/), p. 1-11.*
Blackburn et al., Nucleic Acids in Chemistry and Biology, 2006, 14 pages.*
Office Action dated Nov. 26, 2010 in AU 2007283729.
Busson et al., "Synthesis and antiviral activity of some sugar-modified derivatives of (E)-5-(2-bromovinyl)-2'-deoxyuridine," *Nucleic Acids Symposium Series*, vol. 9, pp. 59-52 (1981)—abstract only.
Chu et al., "Structure-Activity Relationships of Pyrimidine Nucleosides as Antiviral Agents for Human Immunodeficiency Virus Type 1 in Peripheral Blood Mononuclear Cells," *J. Med. Chem.*, vol. 32, No. 3, pp. 612-617 (1989).

(Continued)

*Primary Examiner* — Eric S Olson
*Assistant Examiner* — Zhengfu Wang
(74) *Attorney, Agent, or Firm* — Leydig, Voit & Mayer, Ltd.

(57) ABSTRACT

The invention relates to special nucleosides, for example, a nucleoside of the formula I,

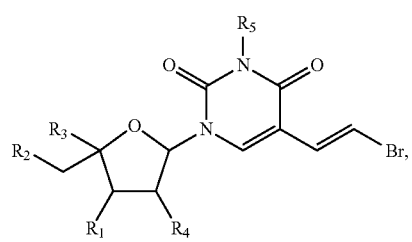

wherein $R_1$-$R_5$ are as described herein, and also to drugs which contain these nucleosides. Furthermore, the invention relates to the use of such nucleosides in a method for suppressing or reducing the formation of resistance in the case of cytotstatic treatment of a cancer patient.

14 Claims, 6 Drawing Sheets

OTHER PUBLICATIONS

Desoize et al., "Multicellular resistance: a paradigm for clinical resistance?" *Crit. Rev. Oncol. Hematol.* Issue 36, pp. 193-207 (2000).

Fahrig et al., "Inhibition of INduced Chemoresistance by Cotreatment with (E)-5-(2-Bromovinyl)-2'-Deoxyuridine (RP101)[1]," *Cancer Res.*, Issue 63, pp. 5745-5753 (2003).

Lefebvre et al., "Mononucleoside Phosphotriester Deriviatives with S-Acyl-2-thioethyl Bioreversible Phosphate-Protecting Groups: Intracellular Delivery of 3'-Azido-2',3'-dideoxythy;midine 5'-Monophosphate," *J. Med. Chem.*, vol. 38, No. 20, pp. 3941-3950 (1995).

Reddy et al., "Solid-Phase Synthesis of Positively Charged Deoxynucleic Guanidine (DNG) Oligonucleotide Mixed Sequences," *Bioorg. Med Chem Lett*. vol. 13, pp. 1281-1285 (2003).

Takara et al., "An update on overcoming MDRI—mediated multidrug resistance in cancer chemotherapy," *Curr. Pharm. Des*. vol. 12, No. 3, pp. 273-286 (2006).

Zou et al., "Differential binding affinities of sugar-modified derivatives of (E)-5-(2-bromovinym)-2'-deoxyuridine for herpes simplex virus-induced and human cellular deoxythy;midine kinases," *Biochem. Pharma.*, vol. 33, No. 11, pp. 1797-1800 (1984)—abstract only.

Office Action dated May 8, 2007 in DE 10 2006 037 786.9.

Korean Patent Office, Office Action in Korean Patent Application No. 10-2009-7004398 (Aug. 11, 2011).

Seela et al., "Dodecanucleotides Containing (E)-5-(2-Bromovinyl)-2'-Deoxyupidine: Influence of a Bulky Major Groove Substituent on Duplex Stability and Endodeoxyribonuclease Eco RI Recognition," *Nucleosides & Nucleotides*, vol. 7(3), pp. 347-363 (1988).

Japanese Patent Office, Office Action in Japanese Patent Application No. 2009-523208 (Jun. 19, 2012).

State Intellectual Property Office of People'S Republic of China, Second Office Action in Chinese Patent Application No. 200780036649.7 (May 31, 2011), 10 pages, which is the Chinese cognate of the present US application.

\* cited by examiner

MMC / BVDU /

A: 3′-bromo-2′,3′-dideoxy-5-(E)-bromovinyluridine

MMC / BVDU /

B: 4-(*t*-butoxycarbonyl)amino-1-(3′-chloro-3′deoxy-5-*(E)*-bromovinyluridin-5′-yl)butanoate

MMC / BVDU /
C:
(*E*)-5-(2-bromovinyl)-3'-chloro-2',3'-dideoxy-uridine-5'-[phenyl-(methoxy-*L*-alaninyl)]-phosphate

MMC / BVDU /
D:
2',5'-dideoxy-5'-fluoro-5-*(E)*-bromovinyluridine

MMC / BVDU / E:

4-ammonium-1-(5'-chloro-2',5'-dideoxy-5-*(E)*-bromovinyluridin-3'-yl)butanoate trifluoroacetate

MMC / BVDU / F:

*(E)*-5-(2-bromovinyl)-5'-chloro-2',5'-dideoxy-uridine-3'-[phenyl-(methoxy-L-alaninyl)]-phosphate

MMC / BVDU /
G:
3′,5′-difluoro-2′,3′,5′-trideoxy-5-(E)-bromovinyluridine

MMC / BVDU /
H:
3′,5′-dibromo-2′,3′,5′-trideoxy-5-(E)-bromovinyluridine

MMC / BVDU / I:

5′-bromo-2′,5′-dideoxy-5-*(E)*-bromovinyluridine

MMC / BVDU / J:

5′-azido-2′,5′-dideoxy-5-*(E)*-bromovinyluridine

MMC / BVDU /
K:
1-(3'-azido-2',3'-dideoxy-β-D-erythro-pentofuranosyl)
-5-*(E)*-(2-bromovinyl)-2,4(1*H*,3*H*)-pyrimidinedione

MMC / BVDU /
L:
3'-chloro-2',3'-dideoxy-5-[E]-bromovinyluridine

NUCLEOSIDES FOR SUPPRESSING OR REDUCING THE DEVELOPMENT OF RESISTANCE IN CYTOSTATIC THERAPY

CROSS-REFERENCE TO RELATED APPLICATIONS

This patent application is the U.S. national phase of International Application No. PCT/EP2007/07147, filed on Aug. 13, 2007, which claims the benefit of German Patent Application No. 10 2006 037 786.9, filed Aug. 11, 2006, the disclosures of which are incorporated by reference.

The invention relates to special nucleosides and also to drugs which contain these nucleosides. Furthermore, the invention relates to the use of nucleosides of this type for the manufacture of a medicament, in particular for suppressing or reducing the formation of resistance in the case of cytostatic treatment.

Chemotherapy is the standard therapy for cancer diseases. Cytostatics influence cell division and are therefore particularly toxic for rapidly growing tumour cells. Cytostatics induce apoptosis, i.e. they lead to the cell death of the tumour cells. Unfortunately, the resistance-free treatment period with the cytostatics which are currently on the market is usually not long enough to destroy the tumour entirely. In order to improve this situation, "chemosensitisers" have been developed, which counteract existing resistance.

If the resistance is caused by amplification (multiplication) and overexpression of the "multi-drug resistance" gene (MDR-1), this can be reduced by inactivation of the gene product thereof (P-glycoprotein) (Takara K, Sakaeda T, Okumura K. An update on overcoming MDR1-mediated multi-drug resistance in cancer chemotherapy. Curr. Pharm. Des. 2006; 12 (3): 273-86).

Severe side effects have blocked the use of P-glycoprotein inhibitors to date. Substances of the third generation can probably be used only for short-term treatment because of their toxic effect and also only in the case of those few tumours, the resistance of which is based exclusively on the effect of the "multi-drug resistance" gene. Furthermore, inhibitors of the receptors for tyrosine kinase or the overexpression of individual oncogenes have been developed. However, still only a few tumours are suitable for treatment (Desoize B., Jardillier J., Multicellular resistance: a paradigm for clinical resistance? Crit. Rev. Oncol. Hematol. 2000; 36: 193-207).

5-substituted nucleosides for inhibiting the formation of resistance in the case of cytostatic treatment are known from EP 0 806 956. The compounds cited here concern (E)-5'-(2-bromovinyl)-2'-deoxyuridine (BVDU) and (E)-5'-(2-bromovinyl)uracil (BVU).

These prevent the formation of resistance and combat resistances which do not already exist. In contrast to the attempts which have been known for decades and are generally unsuccessful for circumventing or reducing already existing chemoresistances, no competition exists worldwide for this technological approach (Fahrig, R., Heinrich, J. C., Nickel, B., Wilfert, F., Leisser, C., Krupitza, G., Praha, C., Sonntag, D., Fiedler, B., Scherthan, H., and Ernst, H. Inhibition of induced chemoresistance by co-treatment with (E)-5-(2-bromovinyl)-2'-deoxyuridine (RP101), Cancer Res. 63 (2003) 5745-5753). The first drug BVDU revealed a statistically significant effect in two clinical studies with pancreas cancer patients. The effect of the co-treatment of cytostatics with BVDU has been more effective than any other previously described chemotherapy.

It was therefore the object of the present invention to provide substances which have higher effectiveness, relative to compounds known from the state of the art, with respect to the suppression or reduction of the formation of resistance in the case of cytostatic treatment.

This object is achieved by the features of the nucleosides and the drug described herein, and the advantageous developments thereof. Uses according to the invention are also described.

According to the invention, nucleosides of the general formula I are provided

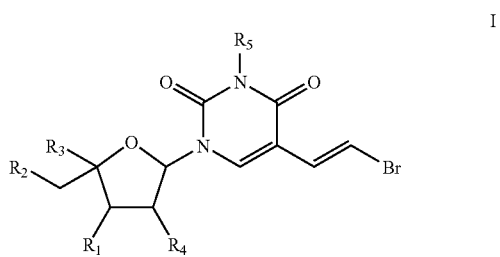

having $R_1$ and $R_2$, independently of each other, selected from the group comprising H, halogen, $OR_8$, CN, $N_3$, $NR_6R_7$ and prodrug radicals bonded via an oxygen atom, $R_3$=H, straight-chain or branched $C_1$-$C_8$ alkyl, straight-chain or branched $C_1$-$C_8$ alkylene, $R_4$=H, halogen, $OR_8$, $N_3$, $NR_6R_7$ or $R_4$ together with $R_1$ represent a second bond between the C-atoms adjacent to $R_1$ and $R_4$, $R_5$=H, $C_1$-$C_8$ alkyl or aryl and $R_6$, $R_7$ and $R_8$, independently of each other, H, straight-chain or branched $C_1$-$C_8$ alkyl or acetyl, the compounds with the following radicals being excluded:
$R_1$=$N_3$, $R_2$=OH, $R_3$=$R_4$=$R_5$=H,
$R_1$=$N_3$, $R_2$=O-acetyl, $R_3$=$R_4$=$R_5$=H,
$R_1$=$N_3$, $R_2$=O-triphenylmethyl, $R_3$=$R_4$=$R_5$=H,
$R_1$=$N_3$, $R_2$=phosphate, $R_3$=$R_4$=$R_5$=H,
$R_1$=$N_3$, $R_2$=triphosphate, $R_3$=$R_4$=$R_5$=H,
$R_1$=$NH_2$, $R_2$=OH, $R_3$=$R_4$=$R_5$=H,
$R_1$=$NH_2$, $R_2$=triphosphate, $R_3$=$R_4$=$R_5$=H,
$R_1$=F, $R_2$=OH, $R_3$=$R_4$=$R_5$=H,
$R_1$=F, $R_2$=O-acetyl, $R_3$=$R_4$=$R_5$=H,
$R_1$=F, $R_2$=triphosphate, $R_3$=$R_4$=$R_5$=H,
$R_1$=Cl, $R_2$=OH, $R_3$=$R_4$=$R_5$=H,
$R_1$=OH, $R_2$=$N_3$, $R_3$=$R_4$=$R_5$=H,
$R_1$=OH, $R_2$=$NH_2$, $R_3$=$R_4$=$R_5$=H,
$R_1$=OH, $R_2$=NH—$SO_2$—$(CH_2)_3$—Cl, $R_3$=$R_4$=$R_5$=H,
$R_1$=OH, $R_2$=NH—$SO_2$—$(CH_2)_3$—$SO_3$H, $R_3$=$R_4$=$R_5$=H,
$R_1$=OH, $R_2$=$C_1$, $R_3$=$R_4$=$R_5$=H,
$R_1$=OH, $R_2$=Br, $R_3$=$R_4$=$R_5$=H,
$R_1$=OH, $R_2$=I, $R_3$=$R_4$=$R_5$=H,
$R_1$=OH, $R_2$=prodrug radical, $R_3$=$R_4$=$R_5$=H,
$R_1$=prodrug radical selected from the group consisting of ester, amino acid ester, carbonates and ether, $R_2$=OH, $R_3$=$R_4$=$R_5$=H,
$R_1$=prodrug radical selected from the group consisting of ester, amino acid ester, carbonates and ether, $R_2$=prodrug radical selected from the group consisting of ester, amino acid ester, carbonates and ether, $R_3$=$R_4$=$R_5$=H,
$R_1$=$N_3$, $R_2$=$N_3$, $R_3$=$R_4$=$R_5$=H, $R_1=NH_2$, $R_2=NHR_9$ with $R_9=H$, $COCH_3$, $COC_3H_7$, $COPh$, $COOC_2H_5$, $COOCH_2CH=CH_2$, $COCH=CHCH_3$, $CHO$ or $COOCH_2Ph$,
$R_3=R_4=R_5=H$,
$R_1=NHR_9$ with $R_9=COCH_3$, $COOC_2H_5$, $R_2=NH_2$,
$R_3=R_4=R_5=H$,
$R_1=NHCOOCH_2Ph$, $R_2=NHCOOCH_2CHCH_2$,
$R_3=R_4=R_5=H$,
$R_1=NHCOOCH_2Ph$, $R_2=NH_2$, $R_3=R_4=R_5=H$,
$R_1=NHCOOCH_2CH=CH_2$, $R_2=NH_2$, $R_3=R_4=R_5=H$ and $R_1=NHCHO$,
$R_2=NHCHO$, $R_3=R_4=R_5=H$.

Drugs which comprise nucleosides of the general formula I are likewise provided.

With respect to the use, this relates in particular to the suppression or reduction of the formation of resistance in the case of cytostatic treatment. Nucleosides of the general formula I are hereby used.

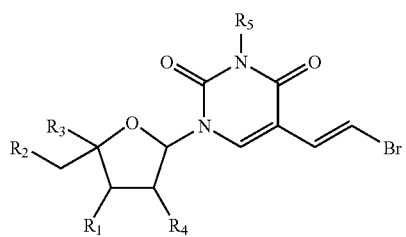

having
$R_1$ and $R_2$, independently of each other, selected from the group consisting of H, halogen, $OR_8$, CN, $N_3$, $NR_6R_7$ and prodrug radicals bonded via an oxygen atom,
$R_3=H$, straight-chain or branched $C_1$-$C_8$ alkyl, straight-chain or branched $C_1$-$C_8$ alkylene,
$R_4=H$, halogen, $OR_8$, $N_3$, or $NR_6R_7$
$R_5=H$, $C_1$-$C_8$ alkyl or aryl and
$R_6$, $R_7$ and $R_8$, independently of each other, H, straight-chain or branched $C_1$-$C_8$ alkyl or acetyl,
the compounds with the following radicals being excluded:
$R_1=OH$, $R_2=OH$, $R_3=R_4=R_5=H$ and
$R_1=OH$, $R_2=$prodrug radical, $R_3=R_4=R_5=H$.

Further uses relate to the resistance-free therapy of infectious diseases caused by bacteria, plasmodia or Leishmania.

The application can thereby be effected both in a single formulation, i.e. as combination preparation, or also in separate formulations. In the case of the separate formulation, a temporally offset administration of the two formulations is also possible.

With respect to the galenics, there are no restrictions so that all formulation forms known from the state of the art can be used. There are included for this purpose for example tablets, capsules, sprays, dragees, emulsions, liquids and ampoules.

Contrary to the current and not very successful mode of operation for combating resistances, the substances cited according to the invention intervene much earlier. They prevent the formation of resistances. The causes and not the symptoms of an illness are therefore combated.

The subject according to the invention is intended to be explained in more detail with reference to the subsequent Figures and Examples without wishing to restrict the latter to the special embodiments shown here.

FIGS. 1 to 12 show the influence of compounds according to the invention in combination with mitomycin C (MMC) in comparison with administration solely of MMC or for the administration of MMC with BVDU on the cell count of AH13r cells in the course of time. AH13r cells were thereby subjected to increasing doses of the cytostatic MMC. It can be detected in all Figures that the effect of MMC together with the compounds according to the invention is significantly greater in comparison with MMC and BVDU.

EXAMPLES

In General

The educts 5'-O-(4-chlorobenzoyl)-2'-deoxy-5-(E)-bromovinyluridine (P. Herdewijn, J. Balzarini, E. De Clerq, R. Pauwels, M. Baba, J. Med. Chem. 1987, 30, 1270-1278), 5'-O-methylsulphonyl-2'-deoxy-5-(E)-bromovinyluridine (P. M. Reddy, T. C. Bruice; Bioorg. Med. Chem. Lett. 2003, 13; 1281-1286), 5'-O-trityl-2'-deoxy-5-ethyl-uridine (C. K. Chu, R. F: Raymond, M. K: Ahn, V. Giliyar, Z. P. Gu, J. Med. Chem. 1989, 32, 612-617), S-(2-hydroxyethyl)-thiopivaloate (I. Lefebvre, C. Périgaud, A. Pompon, A.-M. Aubertin, J.-L. Girardet, A. Kim, G. Gilles and J.-L. Imbach, J. Med. Chem. 1995, 38, 3941-3950), 5-(E)-bromovinyluridine (E. De Clercq, C. Desgranges, P. Herdewijn, A. S. Jones, M. J. McLean, R. T. Walker, J. Med. Chem. 1986, 29, 213-217), 5-iodouracil (J. Asakura, M. J. Robins, J. Org. Chem. 1990, 55, 4928-4933), 2'-deoxy-2'-fluorouridine (Y. Saito, K. Utsumi, T. Maruyama, T. Kimura, I. Yamamoto, D. D. Richman, Chem. Pharm. Bull. 1994, 42, 595-598), 5-iodo-2'-deoxy-2'-fluorouridine (T. Kniess, M. Grote, B. Noll, B. Johannsen, P. Naturforsch. 2003, 58b, 226-230), 3-(2'-deoxy-2'-fluorouridin-5-yl)-acrylic acid methyl ester (J. Matulic-Adamic, A. T. Daniher, A. Karpeisky, P. Haeberli, D. Sweedler, L. Beigelman, Bioorg. Med. Chem. Lett. 2000, 10, 1299-1302), 3,5-di-O-benzoyl-2-deoxy-2-fluoro-α-D-arabinosylbromide, 1-(2'-deoxy-2'-fluoro-β-D-arabinofuranosyl)-5-ethyluracil (H. G. Howell, P. R. Brodfuehrer, S. R. Brundige, D. A. Benigni, C. Sapino, J. Org. Chem. 1988, 53, 85-88), 5-(E)-bromovinyluracil (P. J. Barr, A. S. Jones, G. Verhelst, R. T. Walker, J. Chem. Soc. Perkin Transactions 1, 1981, 565-570) and 1-(2,3,6-tri-O-acetyl-β-D-arabinofuranosyl)-5-iodouracil (M. J. Robins, S. Manfredini, S. G. Wood, R. J. Wanklin, B. A. Rennie, S. L. Sacks, J. Med. Chem. 1991, 34, 2275-2280), 5'-amino-2',5'-dideoxy-5-(E)-bromovinyluridine, 5'-bromo-2',5'-dideoxy-5-(E)-bromovinyluridine, 5'-chloro-2,5'-dideoxy-5-(E)-bromovinyluridine, 5'-azido-2',5'-dideoxy-5-(E)-bromovinyluridine, 3'-chloro-2',3'-dideoxy-5-(E)-bromovinyluridine and 3'-azido-2',3'-dideoxy-5-(E)-bromovinyluridine (R. Busson, L. Colla, H. Vanderhaeghe, E. De Clercq, Nucleic Acids Research, Symposium Series, 1981, 9, 49-52), 3'-O-(t-butyldimethylsilyl-2'-deoxy-5-(E)-bromovinyluridine (P. Herdewijn, R. Ramamurthy, E. De. Clercq, W. Pfleiderer, Helv. Chim. Acta, 1989, 72, 1739-1748), 2'-deoxy-3'-methoxy-5-(E)-bromovinyluridine (M. Ashwell, A. S. Jones, A. Kumar, J. R. Sayers, R. T. Walker, Tetrahedron, 1987, 43, 20, 4601-4608) were synthesised analogously to the mentioned literature data.

All further educts were commercially available.

The column-chromatographic purification of the substances was effected with the indicated solvents on silica gel 60 (FLUKA, 0.040-0.063 mm). For thin-film chromatography, silica gel films (Merck, silica gel 60 $F_{254}$) were used.

The $^{31}$P-NMR spectra were measured with 85% phosphoric acid as external standard.

1. 3'-substituted BVDU derivates

1.1. 3'-halogen-BVDU

1.1.1. 2',3'-dideoxy-3'-bromo-5-(E)-bromovinyluridine

1.1.1.1. 2,3'-anhydro-2'-deoxy-5'-O-benzoyl-5-(E)-bromovinyluridine

A solution of 13.8 g (68 mmol) diisopropylazodicarbonic ester and 8.3 g (68 mmol) benzoic acid in 75 ml DMF are added in drops within 155 min to a solution of 15.0 g (45 mmol) BVDU and 17.8 g (68 mmol) triphenylphosphine. Agitation takes place thereafter for another 30 min at room temperature and 17.8 g triphenylphosphine is added again thereto. Within 10 min, a solution of 13.8 g (68 mmol) diisopropylazodicarbonic ester in 10 ml DMF is added thereto in drops and left for 3 h to agitate at room temperature. DC-control (dichloromethane/methanol 5:1) reveals that the reaction is finished. The reaction mixture is poured into 1.5 l diethylether, the precipitated precipitate is suctioned off and washed with diethylether. After drying, the yield is 10.1 g (53.5%).

1.1.1.2. 2',3'-dideoxy-3'-bromo-5'-O-benzoyl-5-(E) bromovinyluridine 3.0 g (7.16 mmol) 2,3'-anhydro-2'-deoxy-5'-O-benzoyl-5-(E)-bromovinyluridine and 2.40 g (15.0 mmol) pyridinium-hydrobromide are suspended in 20 ml DMF and heated to 100° C. After 3 h the reaction is terminated (DC-control with dichloromethane/methanol 20:1). The obtained solution is diluted with 200 ml water and extracted with acetic ester. The purified acetic ester phases are washed twice with respectively 100 ml 0.5 M hydrochloric acid and three times with 100 ml common salt solution, dried with magnesium sulphate, filtered off and purified firstly with dichloromethane/acetic ester 12:1, then with chloroform/methanol 25:1 several times by column chromatography. The yield is 2.0 g (55.8%) of a colourless foam.

1.1.1.3. 2',3'-dideoxy-3'-bromo-5'-(E)-bromovinyluridine 1.92 (3.84 mmol) of 2,3'-dideoxy-3'-bromo-5'-O-benzoyl-5-(E)-bromovinyluridine are dissolved in 25 ml THF and mixed with 10 ml water and with 9.6 ml (19.2 mmol) 2 M sodium hydroxide solution. After 2.5 h the conversion is terminated (DC-control with chloroform/methanol 15:1). The batch is poured into 50 ml saturated common salt solution and extracted with acetic ester. The combined extracts are dried with magnesium sulphate. After filtration and distilling-off of the solvent, 1.3 g (81.2%) of a white, solid foam is obtained by repeated purification by column chromatography (chloroform/methanol 15:1).

$^1$H-NMR (500 MHz, DMSO-d$_6$): 2.45 (m, 1H); 2.72 (m, 1H); 3.71 (m, 2H); 4.19 (m, 1H); 4.61 (m, 1H); 5.31 (s, 1H); 6.17 (t, 1H); 6.83 (d, 1H); 7.25 (d, 1H); 8.07 (s, 1H); 11.60 (s, 1H) ppm.

FIG. 1 shows the results of this compound according to the invention in combination with mitomycin C (MMC) in comparison with MMC alone and MMC in combination with BVDU.

1.1.2. 1-(3'-chloro-2,3-dideoxy-β-D-threo-pentofuranosyl)-5-(E)-(2-bromovinyl)-2,4-(1H, 3H)-pyrimidinedione

1.1.2.1 1-(5'-O-(4-chlorobenzoyl)-3'-chloro-2,3'-dideoxy-β-D-threo-pentofuranosyl)-5-(E)-(2-bromovinyl)-2,4-(1H,3H)-pyrimidinedione 2.0 g (4.24 mmol) 5'-O-(4-chlorobenzoyl)-2'-deoxy-5-(E)-bromovinyluridine are dissolved in 40 g HMPT and 1.6 g (13.44 mmol) thionylchloride are added thereto. After 45 min the reaction is terminated. It is mixed with water and extracted with acetic ester. After drying with sodium sulphate, filtration and centrifugation of the solvent, it is purified by column chromatography (cyclohexane/acetic ester 7:3). 1.32 g (64%) of a colourless solid with a melting point 89-91° C. is obtained.

1.1.2.2. 1-(3'-chloro-2',3'-dideoxy-β-D-threo-pentofuranosyl)-5-(E)-(2-bromovinyl)-2,4-(1H, 3H)-pyrimidinedione 0.9 g (1.84 mmol) 1-(5'-O-(4-chlorobenzoyl)-3'-chloro-2,3'-dideoxy-β-D-threo-pentofuranosyl)-5-(E)-(2-bromovinyl)-2,4-(1H,3H)-pyrimidinedione are dissolved in 50 ml methanol and 0.15 g (2.78 mmol) sodium methylate are added. After 2 h, the DC-control (dichloromethane/methanol 95:5) reveals that the reaction is terminated. Ion exchanger (DOWEX-H$^+$50 WX 4 (Merck, 105238), activated under methanol) is added, filtered and washed again with methanol. After centrifugation of methanol, purification by column chromatography is effected (acetic ester). 0.43 g (67%) of a colourless solid with a melting point of 183-185° C. is obtained.

$^1$H-NMR (300 MHz, DMSO-d$_6$): 2.37 (m, 1H); 3.00 (m, 1H); 3.77 (m, 2H); 4.20 (m, 1H); 4.76 (m, 1H); 5.00 (t, 1H); 6.00 (m, 1H); 6.95 (d, 1H); 7.27 (d, 1H); 7.92 (s, 1H); 11.63 (s, 1H) ppm.

1.2. 5'-O-derivatives of 3'-halogen-BVDU

1.2.1. 5'-O-acyl derivatives of 3'-halogen-BVDU

1.2.1.1. 5'-O-pivaloyl-3'-chloro-2',3'-deoxy-5-(E)-bromovinyl-uridine 1.25 g (3.55 mmol) 2',3'-dideoxy-3'-chloro-5-(E)-bromovinyluridine, 0.05 g (0.41 mmol) 4-dimethylaminopyridine are dissolved in THF/pyridine (5 ml respectively), cooled to 0° C. and mixed with 0.54 g (4.44 mol) pivaloyl-chloride. It is left to heat to room temperature.

After 2 h the reaction is terminated (DC-control with dichloromethane/methanol 20:1). After pouring into a solution comprising citric acid in 50 ml water, extraction takes place with acetic ester and the combined extracts are washed with phosphate buffer and dried with magnesium sulphate. After filtration and centrifugation of the solvent, purification by column chromatography is effected (dichloromethane/methanol 75:1). 1.33 g (86.4%) of a colourless solid with a melting point of 136° C. is obtained.

$^1$H-NMR (300 MHz, DMSO-d$_6$): 1.14 (s, 9H); 2.57 (m, 1H); 2.71 (m, 1H); 4.28 (m, 3H); 4.70 (m, 1H); 6.23 (m, 1H); 6.90 (d, 1H); 7.29 (s, 1H); 7.76 (s, 1H); 11.65 (s, 1H) ppm.

1.2.1.2. 5'-O-ethoxycarbonyl-(E)-5-(2-bromovinyl)-3'-chloro-2',3'-dideoxyuridine)

310 mg (0.88 mmol) 2',3'-dideoxy-3'-chloro-5-(E)-bromovinyluridine is dissolved in dichloromethane/pyridine (respectively 3 ml) and mixed with 108 mg (1 mmol) ethoxycarbonyl chloride at 0° C. After 2 h the reaction is terminated (DC-control with chloroform/methanol 25:1). Dilution takes place with 20 ml dichloromethane, washing with 1 M hydrochloric acid and with phosphate buffer. After drying over magnesium sulphate, filtration and centrifugation of the solvent, purification by column chromatography is effected with chloroform/methanol 25:1. 200 mg (53.6%) of a colourless solid with a melting point of 181° C. is obtained.

$^1$H-NMR (500 MHz, DMSO-$d_6$): 1.23 (t, 3H); 2.65 (m, 2H); 4.15 (q, 2H); 4.37 (m, 3H); 4.71 (m, 1H); 6.22 (m, 1H); 6.87 (d, 1H); 7.29 (d, 1H); 7.78 (s, 1H); 11.64 (s, 1H) ppm.

1.2.2. amino acid ester of 3'-halogen-BVDU 1.2.2.1. 5'-O-(t-butoxycarbonylaminoacetyl)-3'-chloro-2',3'-dideoxy-5-(E)-bromovinyluridine 1.06 g (3 mmol) 2',3'-dideoxy-3'-chloro-5-(E)-bromovinyluridine, 0.58 g (3.3 mmol) N—BOC-glycine, 0.45 g (3.3 mmol) 1-hydroxybenzotriazole and 0.99 g (3.3 mmol) 1-(3-dimethylaminopropyl)-3-ethylcarbodiimide methiodide are dissolved in 25 ml dichloromethane. After 8 h, respectively the same quantity of N—BOC-glycine, 1-hydroxybenzotriazole and 1-(3-dimethylaminopropyl)-3-ethylcarbodiimide methiodide are added once again. After a further 16 h the reaction is terminated (DC-control with dichloromethane/methanol 25:1). The dichloromethane solution is washed with water and dried with sodium sulphate. After filtration and centrifugation of the solvent, purification is effected by column chromatography (dichloromethane/methanol 25:1). 1.03 g (68%) of a colourless foam is obtained.

$^1$H-NMR (300 MHz, DMSO-$d_6$): 1.37 (s, 9H); 2.57 (m, 1H); 2.71 (m, 1H); 3.72 (m, 2H); 4.23 (m, 1H); 4.33 (m, 2H); 4.69 (m, 1H); 6.24 (m, 1H); 6.93 (d, 1H); 7.26 (t, 1H); 7.31 (d, 1H); 7.77 (s, 1H); 11.66 (s, 1H) ppm.

1.2.2.2. 5'-O-(ammoniumacetyl-3'-chloro-2',3'-dideoxy-5-(E)-bromovinyluridine-trifluoroacetate 0.81 g (1.6 mmol) 5'-O-(t-butoxycarbonylaminoacetyl)-3'-chloro-2',3'-dideoxy-5-(E)-bromovinyluridine are dissolved in 20 ml trifluoroacetic acid. After 45 min the splitting of the BOC protective group is complete (DC-control with dichloromethane/methanol 95:5). Trifluoroacetic acid is centrifuged off, the residue is absorbed in some methanol and treated with diethylether. The precipitated precipitate is suctioned off, washed with diethylether and reprecipitated again from methanol/diethylether. After filtering-off, washing with diethylether and drying, the yield is 0.38 g (45.7%) of a colourless powder.

$^1$H-NMR (300 MHz, DMSO-$d_6$): 2.59 (m, 1H); 2.75 (m, 1H); 3.87 (m, 2H); 4.26 (m, 1H); 4.44 (m, 2H); 4.73 (m, 1H); 6.24 (m, 1H); 6.93 (d, 1H); 7.32 (d, 1H); 7.80 (s, 1H); 8.32 (s, 3H); 11.68 (s, 1H) ppm.

1.2.2.3. 4-(t-butoxycarbonyl)amino-1-(3'-chloro-2',3'-dideoxy-5-(E)-bromovinyluridin-5'-yl)butanoate 2.0 g (9.84 mmol) N—BOC-4-aminobutanoic acid and 1.2 g (9.84 mmol) 4-dimethylaminopyridine are dissolved in 20 ml dichloromethane. 3.46 g (9.84 mmol) 2',3'-dideoxy-3'-chloro-5-(E)-bromovinyluridine are added thereto and, after cooling to 0° C., 2.03 g (9.84 mmol) N,N'-dicyclohexylcarbodiimide. After heating to room temperature and after 20 h agitation at room temperature the reaction is terminated (DC-control with dichloromethane/methanol 20:1). The batch is filtered and mixed in. After dissolving in acetic ester it is cooled to −20° C., the precipitate is filtered off and washed with a little acetic ester cooled to −20° C. The filtrate is mixed in and purified several times by column chromatography with dichloromethane/acetic ester (4:1). 3.2 g (60.6%) of a colourless foam is obtained.

$^1$H-NMR (500 MHz, DMSO-$d_6$): 1.36 (s, 9H); 1.62 (m, 2H); 2.31 (m, 2H); 2.52 (m, 1H); 2.72 (m, 1H); 2.92 (m, 2H); 4.31 (m, 3H); 4.71 (m, 1H); 6.22 (m, 1H); 6.79 (m, 1H); 6.92 (d, 1H); 7.31 (m, 1H); 7.77 (s, 1H); 11.64 (s, 1H).

FIG. 2 shows the results of this compound according to this invention in combination with mitomycin C (MMC) in comparison with MMC alone and MMC in combination with BVDU.

1.2.2.4. 4-ammonium-1-(3'-chloro-2',3'-dideoxy-5-(E)-bromovinyluridin-5'-yl)butanoate-trifluoroacetate 310 mg (0.577 mmol) 4-(t-butoxycarbonyl)amino-1-(3'-chloro-2',3'-dideoxy-5-(E)-bromovinyluridin-5'-yl)butanoate are dissolved in 5 ml dichloromethane and mixed with 5 ml trifluoroacetic acid. After 30 min agitation at room temperature the conversion is complete. (DC-control dichloromethane/methanol 20:1). Dichloromethane and trifluoroacetic acid are distilled off and the residue is mixed with 20 ml diethylether. It is left to agitate for 2 h until a fine, pulverulent precipitate is produced, filtered, washed with diethylether and dried in a vacuum. 250 mg (78.7%) of a colourless solid with a melting point of 89° C. is obtained.

$^1$H-NMR (500 MHz, DMSO-$d_6$): 1.82 (m, 2H); 2.49 (m, 2H); 2.59 (m, 1H); 2.72 (m, 1H); 2.81 (m, 2H); 4.22 (m, 1H); 4.32 (m, 2H); 4.69 (m, 1H); 6.22 (m, 1H); 6.94 (d, 1H); 7.29 (d, 1H); 7.73 (s, 3H); 7.78 (s, 1H); 11.65 (s, 1H).

1.2.2.5. 5'-O—(N-t-butyloxycarbonyl-L-valinoyl)-3'-chloro-2',3'-dideoxy-5-(E)-bromovinyluridine At 0° C., 1.00 g (2.84 mmol) 3'-chloro-2',3'-dideoxy-5-(E)-bromovinyluridine are placed in 20 ml dichloromethane. Then 618 mg (2.84 mmol, 1.0 eq.) N-t-butyloxycarbonyl-L-valine, 347 mg (2.84 mmol, 1.0 eq.) N,N-dimethylaminopyridine and also 587 mg (2.84 mmol, 1.0 eq.) N,N'-dicyclohexylcarbodiimide are added and subsequently the reaction mixture is agitated for 20 h at room temperature. The resulting precipitate is filtered off and washed with dichloromethane. The filtrate is washed with diluted citric acid solution, NaHCO$_3$ solution and also NaCl solution and subsequently dried with Na$_2$SO$_4$. The solvent is removed on the rotary evaporator. Purification by column chromatography (CHCl$_3$/MeOH, 95/5) yields 1.09 g (1.98 mmol, 70%) 5'-O—(N-t-butyloxycarbonyl-L-valinoyl)-3'-chloro-2',3'-dideoxy-5-(E)-bromovinyluridine as a white solid with a melting point of 75-76° C.

$^1$H-NMR (500 MHz, DMSO-$d_6$): 0.85 (d, 3H); 0.87 (d, 3H); 1.38 (s, 9H); 1.98 (m, 1H); 2.54 (m, 1H); 2.73 (m, 1H); 3.81 (t, 1H); 4.26 (m, 2H); 4.34 (m, 1H); 4.68 (q, 1H); 6.24 (t, 1H); 6.91 (d, 1H); 7.21 (d, 1H); 7.31 (d, 1H); 7.76 (s, 1H); 11.67 (s, 1H) ppm.

1.2.2.6. (3'-chloro-2',3'-dideoxy-5'-O-L-valinoyl-5-(E)-bromovinyluridine)trifluoroacetate At 0° C., 600 mg (1.09 mmol) 5'-O—(N-t-butyloxycarbonyl-L-valinoyl)-3'-chloro-2',3'-dideoxy-5-(E)-bromovinyluridine are placed in 5 ml dichloromethane, 1.0 ml (14 mmol) trifluoroacetic acid are added and subsequently the reaction mixture is agitated for 3 h at room temperature. The solvent is removed on the rotary evaporator. The crude product is mixed with 5 ml diethylether and agitated for 20 h at room temperature. The solvent is decanted off and the residue left on the rotary evaporator for 1 h at 40° C. The result is 540 mg (956 μmol 88%) (3'-chloro-2',3'-dideoxy-5'-O-L-valinoyl-5-(E)-bromovinyluridine) trifluoroacetate as a white solid with a melting point of 110-112° C.

$^1$H-NMR (500 MHz, DMSO-d$_6$): 0.95 (d, 3H); 0.97 (d, 3H); 2.17 (m, 1H); 2.60 (m, 1H); 2.79 (m, 1H); 3.93 (bs, 1H); 4.27 (m, 1H); 4.46 (m, 2H); 4.74 (q, 1H); 6.26 (dd, 1H); 6.91 (d, 1H); 7.32 (d, 1H); 7.80 (s, 1H); 8.34 (bs, 3H); 11.69 (s, 1H) ppm.

1.2.2.7. 5'-O—(N-t-butyloxycarbonyl-L-valyl-L-valinoyl)-3'-chloro-2',3'-dideoxy-5-(E)-bromovinyluridine At 0° C., 1.00 g (2.84 mmol) (3'-chloro-2',3'-dideoxy-5'-(E)-bromovinyluridine are placed in 20 ml dichloromethane. Then 880 mg (2.78 mmol, 1.0 eq.) N-t-butyloxycarbonyl-L-valyl-L-valine, 347 mg (2.84 mmol, 1.0 eq.) N,N-dimethylaminopyridine and also 587 mg (2.84 mmol, 1.0 eq.) N,N'-dicyclohexylcarbodiimide are added and subsequently the reaction mixture is agitated for 3 d at room temperature. The resulting precipitate is filtered off and washed with dichloromethane. The filtrate is washed with diluted citric acid solution, NaHCO$_3$ solution and NaCl solution and subsequently dried with Na$_2$SO$_4$. The solvent is removed on the rotary evaporator. Purification by column chromatography (dichloromethane/acetic ester, 3/1) yields 610 mg (939 μmol, 33%) 5'-O—(N-t-butyloxycarbonyl-L-valyl-L-valinoyl)-3'-chloro-2',3'-dideoxy-5-(E)-bromovinyluridine as a white solid with a melting point of 102-103° C.

$^1$H-NMR (500 MHz, DMSO-d$_6$): 0.81-0.90 (m, 12H); 1.37 (s, 9H); 1.91 (m, 1H); 2.06 (m, 1H); 2.54 (m, 1H); 2.74 (m, 1H); 3.88 (t, 1H); 4.19 (t, 1H); 4.23-4.35 (m, 3H); 4.68 (q, 1H); 6.24 (t, 1H); 6.64 (d, 1H); 6.91 (d, 1H); 7.31 (d, 1H); 7.77 (s, 1H); 8.03 (d, 1H); 11.67 (s, 1H) ppm.

1.2.2.8. [3'-chloro-2',3'-dideoxy-5'-O-(L-valyl-L-valinoyl)-5-(E)-bromovinyluridine]trifluoroacetate At 0° C., 300 mg (462 μmol) 5'-O—(N-t-butyloxycarbonyl-L-valyl-L-valinoyl)-3'-chloro-2',3'-dideoxy-5-(E)-bromovinyluridine are placed in 5 ml dichloromethane, 0.5 ml (6.7 mmol) trifluoroacetic acid are added and subsequently the mixture is agitated for 3 h at room temperature. The solvent is removed on the rotary evaporator. The crude product is mixed with 5 ml diethylether and agitated for 1 h at room temperature. The solvent is decanted off and the residue is left on the rotary evaporator for 1 h at 40° C. The result is 280 mg (422 μmol, 91%) [3'-chloro-2',3'-dideoxy-5'-O-(L-valyl-L-valinoyl)-5-(E)-bromovinyluridine]trifluoroacetate as a white solid with a melting point of 169-170° C.

$^1$H-NMR (500 MHz, DMSO-d$_6$): 0.91-0.96 (m, 12H); 2.08-2.14 (m, 2H); 2.59 (m, 1H); 2.76 (m, 1H); 3.71 (t, 1H); 4.22-4.26 (m, 2H); 4.31-4.38 (m, 2H); 4.68 (q, 1H); 6.25 (t, 1H); 6.90 (d, 1H); 7.32 (d, 1H); 7.81 (s, 1H); 8.06 (bs, 3H); 8.56 (d, 1H); 11.68 (s, 1H) ppm.

1.2.2.9 3'-azido-5'-O—(N-t-butyloxycarbonyl-L-valyl-L-valinoyl)-2',3'-dideoxy-5-(E)-bromovinyluridine At 0° C., 1.02 g (2.84 mmol) 3'-azido-2',3'-dideoxy-5-(E)-bromovinyluridine are placed in 20 ml dichloromethane. Then 880 mg (2.78 mmol, 1.0 eq.) N-t-butyloxycarbonyl-L-valyl-L-valine, 347 mg (2.84 mmol, 1.0 eq.) N,N-dimethylaminopyridine and also 587 mg (2.84 mmol, 1.0 eq.) N,N'-dicyclohexylcarbodiimide are added and subsequently the reaction mixture is agitated for 24 h at room temperature. The resulting precipitate is filtered off and washed with dichloromethane. The filtrate is washed with diluted citric acid solution, NaHCO$_3$ solution and also NaCl solution and subsequently dried with Na$_2$SO$_4$. The solvent is removed on the rotary evaporator. Purification by column chromatography (dichloromethane/acetic ester, 3/1) yields 550 mg (838 μmol, 30%) 3'-azido-5'-O—(N-t-butyloxycarbonyl-L-valyl-L-valinoyl)-2',3'-dideoxy-5-(E)-bromovinyluridine as white solid with a melting point of 95-97° C.

$^1$H-NMR (500 MHz, DMSO-d$_6$): 0.81-0.91 (m, 12H); 1.37 (s, 9H); 1.91 (m, 1H); 2.07 (m, 1H); 2.38 (m, 1H); 2.51 (m, 1H); 3.88 (t, 1H); 4.01 (q, 1H); 4.19 (t, 1H); 4.30 (m, 2H); 4.45 (q, 1H); 6.12 (t, 1H); 6.64 (d, 1H); 6.92 (d, 1H); 7.31 (d, 1H); 7.77 (s, 1H); 8.04 (d, 1H); 11.66 (s, 1H) ppm.

1.2.2.10. [3'-azido-2',3'-dideoxy-5'-O-(L-valyl-L-valinoyl)-5-(E)-bromovinyluridine]trifluoroacetate At 0° C., 200 mg (305 μmol) 3'-azido-5'-O—(N-t-butyloxycarbonyl-L-valyl-L-valinoyl)-2',3'-dideoxy-5-(E)-bromovinyluridine are placed in 4 ml dichloromethane, 0.33 ml (4.47 mmol) trifluoroacetic acid are added and subsequently the reaction mixture is agitated for 3 h at room temperature. The solvent is removed on the rotary evaporator. The crude product is mixed with 5 ml diethylether and agitated for 1 h at room temperature. The solvent is decanted off and the residue is left on the rotary evaporator for 1 h at 40° C. The result is 200 mg (298 μmol 98%) [3'-azido-2',3'-dideoxy-5'-O-(L-valyl-L-valinoyl)-5-(E)-bromovinyluridine]trifluoroacetate as a white solid with a melting point of 113-115° C.

$^1$H-NMR (500 MHz, DMSO-d$_6$): 0.91-0.96 (m, 12H); 2.08-2.14 (m, 2H); 2.40 (m, 1H); 2.53 (m, 1H); 3.72 (t, 1H); 4.00 (q, 1H); 4.25 (m, 1H); 4.31-4.38 (m, 2H); 4.45 (q, 1H); 6.13 (t, 1H); 6.90 (d, 1H); 7.31 (d, 1H); 7.80 (s, 1H); 8.08 (m, 3H); 8.58 (d, 1H); 11.67 (s, 1H) ppm.

1.2.3. phosphoramidates of 3'-halogen-BVDU

1.2.3.1. (E)-5-(2-bromovinyl)-3'-fluoro-2',3'-dideoxyuridine-5'-[phenyl-(methoxy-L-alaninyl)]-phosphate 255 mg (1.20 mmol) phenyldichlorophosphate and 169 mg (1.20 mmol) L-alaninemethylester hydrochloride are dissolved or suspended in 4 ml THF. This is cooled to −78° C. with a dry ice bath and, at this temperature, 244 mg (2.40 mmol) triethylamine are added in drops, said triethylamine being dissolved in 4 ml THF. After 30 min the addition in drops is terminated and heating to room temperature takes place gradually and agitation takes place in total for 24 h. Thereafter 270 mg (0.80 mmol) 2',3'-dideoxy-3'-fluoro-5-(E)-bromovinyluridine are added and cooled to −78° C. with a dry ice bath. There is added to the obtained suspension in drops a solution of 265 mg (3.22 mmol) N-methylimidazole in 5 ml THF. After 30 min the addition in drops is terminated and heating to room temperature takes place gradually. After a further 48 h the reaction is terminated (DC-control with chloroform/acetic ester 3:2). The batch is added to a mixture of 20 ml phosphate buffer and 25 ml acetic ester and the aqueous phase is extracted another twice with respectively 20 ml acetic ester. After drying with magnesium sulphate, filtration and centrifugation of the solvent, purification by column chromatography with dichloromethane/acetic ester 3:2 is effected. 180 mg (38.8%) of a colourless foam is obtained.

$^1$H-NMR (500 MHz, DMSO-d$_6$): 1.23 (d, 3H); 2.35 (m, 1H); 2.49 (m, 1H); 3.58 (s, 3H); 3.85 (m, 1H); 4.21 (m, 2H); 4.39 (m, 1H); 5.32 (m, 1H); 6.18 (m, 2H); 6.84 (d, 1H); 7.19 (m, 3H); 7.29 (d, 1H); 7.36 (m, 2H); 7.87 (s, 1H); 11.67 (s, 1H) ppm.

$^{31}$P-NMR (122 MHz, DMSO-d$_6$): 5.08; 5.29 ppm.

1.2.3.2. (E)-5-(2-bromovinyl)-3'-chloro-2',3'-dideoxyuridine-5'-[phenyl-(methoxy-L-alaninyl)]-phosphate 1.19 g (5.67 mmol) phenyldichlorophosphate and 0.79 g (5.67 mmol) L-alaninemethylester hydrochloride are dissolved or suspended in 12 ml THF. Cooling takes place to −78° C. with a dry ice bath and, at this temperature, 1.15 g (11.34 mmol) triethylamine are added in drops, said triethylamine being dissolved in 12 ml THF. After 30 min the addition in drops is terminated and heating to room temperature takes place gradually and agitation takes place in total for 24 h.

Thereafter 1.0 mg (2.84 mmol) 2',3'-dideoxy-3'-chloro-5-(E)-bromovinyluridine is added and cooled to −78° C. with a dry ice bath. There is added to the obtained suspension in drops a solution of 1.17 g (14.2 mmol) N-methylimidazole in 12 ml THF. After 30 min the addition in drops is terminated and heating to room temperature takes place gradually. After a further 48 h the reaction is terminated (DC-control with dichloromethane/acetic ester 3:2. The batch is added to a mixture of 75 ml phosphate buffer and 50 ml acetic ester and the aqueous phase is extracted another twice with respectively 40 ml acetic ester. After drying with magnesium sulphate, filtration and centrifugation of the solvent, purification by column chromatography is effected with dichloromethane/acetic ester 3:2 and chloroform/acetone 3:1. 950 mg (56.5%) of a colourless foam is obtained.

$^1$H-NMR (500 MHz, CDCl$_3$): 1.37 (m, 3H); 2.38 (m, 1H); 2.62 (m, 1H); 3.71, 3.72 (s, 3H); 3.75, 3.85 (m, 1H); 4.09 (m, 1H); 4.41 (m, 4H); 6.24, 6.32 (m, 1H); 6.71 (m, 1H); 7.41 (m, 6H); 7.66, 7.70 (s, 1H); 8.88, 8.92 (s, 1H) ppm.

$^{31}$P-NMR (122 MHz, CDCl$_3$): 2.87; 2.74 ppm.

FIG. 3 shows the results of this compound according to the invention in combination with mitomycin C (MMC) in comparison with MMC alone and MMC in combination with BVDU.

1.2.3.3. (E)-5-(2-bromovinyl)-3'-chloro-2',3'-dideoxyuridine-5'-[phenyl-benzyloxy-L-alaninyl)]-phosphate 606 mg (2.87 mmol) phenyldichlorophosphate and 1010 mg (2.87 mmol) L-alaninebenzylester 4-methylbenzenesulphonate are dissolved in 15 ml THF. Cooling takes place to −78° C. with a dry ice bath and, at this temperature, 582 mg (5.75 mmol) triethylamine are added in drops, said triethylamine being dissolved in 5 ml THF. After 35 min the addition in drops is terminated and heating to room temperature takes place gradually and agitation takes place in total for 24 h. Thereafter 505 mg (1.44 mmol) 2',3'-dideoxy-3'-chloro-5-(E)-bromovinyluridine are added and cooled to −78° C. with a dry ice bath. There is added to the obtained suspension in drops a solution of 650 mg (8.0 mmol) N-methylimidazole in 5 ml THF. After 30 min the addition in drops is terminated and heating to room temperature takes place gradually. After a further 48 h the reaction is terminated (DC-control with chloroform/methanol 25:1. The batch is added to a mixture of 50 ml phosphate buffer and 25 ml acetic ester and the aqueous phase is extracted another twice with respectively 25 ml acetic ester. After drying with magnesium sulphate, filtration and centrifugation of the solvent, purification by column chromatography is effected with chloroform/acetic ester 3:2. 520 mg (53.0%) of a colourless foam is obtained.

$^1$H-NMR (500 MHz, DMSO-d$_6$): 1.25 (2×d, 3H); 2.58 (m, 2H); 3.92 (m, 1H); 4.26 (m, 3H); 4.67 (m, 1H); 5.08 (m, 2H); 6.25 (m, 2H); 6.88 (2×d, 1H); 7.18 (m, 3H); 7.36 (m, 8H); 7.81 (2×s, 1H); 11.87 (2×d, 1H) ppm.

$^{31}$P-NMR (122 MHz, DMSO-d$_6$): 4.40; 4.57 ppm.

1.2.3.4. (E)-5-(2-bromovinyl)-3'-bromo-2',3'-dideoxyuridine-5'-[phenyl-(methoxy-L-alaninyl)]-phosphate 401 mg (1.9 mmol) phenyldichlorophosphate and 265 mg (1.9 mmol) L-alaninemethylester hydrochloride are dissolved or suspended in 6 ml THF. Cooling takes place to −78° C. with a dry ice bath and, at this temperature, 385 mg (3.8 mmol) triethylamine are added in drops, said triethylamine being dissolved in 6 ml THF. After 30 min the addition in drops is terminated and heating to room temperature takes place gradually and agitation takes place in total for 24 h. Thereafter 500 mg (1.26 mmol) 2',3'-dideoxy-3'-bromo-5-(E)-bromovinyluridine are added and cooled to −78° C. with a dry ice bath. There is added to the obtained suspension in drops a solution of 415 mg (5.05 mmol) N-methylimidazole in 6 ml THF. After 30 min the addition in drops is terminated and heating to room temperature takes place gradually. After a further 48 h the reaction is terminated (DC-control with chloroform/acetic ester 1:1. The batch is added to a mixture of 25 ml phosphate buffer and 25 ml acetic ester and the aqueous phase is extracted another twice with respectively 20 ml acetic ester. After drying with magnesium sulphate, filtration and centrifugation of the solvent, purification by column chromatography is effected (dichloromethane/acetic ester 3:2). 386 g (48.1%) of a colourless foam is obtained.

$^1$H-NMR (500 MHz, DMSO-d$_6$): 1.25 (d, 3H); 2.71 (m, 2H); 3.61 (s, 3H); 3.85 (m, 1H); 4.18 (m, 1H); 4.27 (m, 1H); 4.42 (m, 1H); 4.66 (m, 1H); 6.11 (m, 1H); 6.28 (m, 1H); 6.88 (d, 1H); 7.19 (m, 3H); 7.31 (m, 1H); 7.38 (m, 2H); 7.81 (s, 1H); 11.65 (s, 1H) ppm.

$^{31}$P-NMR (122 MHz, DMSO-d$_6$): 5.04; 5.11 ppm.

1.2.3.5. 3'-azido-5-(E)-bromovinyl-2',3'-dideoxyuridin]-5'-yl-(methoxy-L-alaninyl]-phenylphosphate 600 mg (2.84 mmol, 2 eq.) phenyldichlorophosphate and 397 mg (2.84 mmol, 2. eq.) L-alaninemethylester hydrochloride are placed in 7 ml THF at −78° C. 576 mg (5.69 mmol, 4 eq.) triethylamine are dissolved in 7 ml THF, added in drops within 30 min and subsequently agitated for 20 h at room temperature. The reaction mixture is cooled to −78° C. and 509 mg (1.42 mmol) 3'-azido-2',3'-dideoxy-5-(E)-bromovinyluridine are added. There is added to the obtained solution in drops a solution of 700 mg (8.53 mmol, 6 eq.) N-methylimidazole in 7 ml THF within 30 min and subsequently agitation takes place for 20 h at room temperature. The batch is added to a mixture of 25 ml phosphate buffer and 25 ml acetic ester and the aqueous phase is extracted another twice with respectively 20 ml acetic ester. The combined organic phase is dried over Na$_2$SO$_4$, filtered and the solvent is removed on the rotary evaporator. Purification by column chromatography, (dichloromethane/acetic ester, 1/1; acetic ester) yields 250 mg (417 μmol, 29%) [3'-azido-5-(E)-bromovinyl-2',3'-dideoxyuridin]-5'-yl-(methoxy-L-alaninyl]-phenylphosphate as white solid.

¹H-NMR (500 MHz, DMSO-d₆): 1.20 (d, 3H); 1.23* (d, 3H); 2.38-2.47 (m, 4H); 3.57 (s, 3H); 3.59* (s, 3H); 3.80-3.91 (m, 2H); 4.03 (q, 1H); 4.08 (q, 1H); 4.16-4.21 (m, 1H); 4.23-4.29 (m, 3H); 4.45-4.52 (m, 2H); 6.09-6.16 (m, 4H); 6.86-6.89 (m, 2H); 7.16-7.22 (m, 6H); 7.28-7.32 (m, 2H); 7.34-7.38 (m, 4H); 7.82 (s, 2H); 11.65 (s, 1H); 11.66* (s, 1H) ppm. The substance comprises a diastereomer mixture (ratio approx. 1.2:1). The signals characterised with * relate to the deficit isomer.

³¹P-NMR (122 MHz, DMSO-d₆): 5.06; 5.20 ppm

1.2.4. phosphoric acid derivatives of 3'-halogen-BVDU

1.2.4.1 3'-chloro-2',3'-dideoxy-5-(E)-(2-bromovinyluridinyl)-5'-yl-diethylphosphate 500 mg (1.42 mmol) 2',3'-dideoxy-3'-chloro-5-(E)-bromovinyluridine are dissolved in 10 ml THF and 1 ml pyridine. Cooling takes place in the ice bath to 0° C., and a solution of 735 mg (4.3 mmol) diethylchlorophosphate are added in drops within 5 min. After 18 h, 1 ml pyridine and 735 mg diethylchlorophosphate are added again and, after a further 18 h, the conversion is complete (DC-control with chloroform/methanol 10:1). The batch is added to a mixture of 20 ml phosphate buffer and 25 ml acetic ester and the aqueous phase is extracted another three times with 15 ml acetic ester. The combined extracts are dried with magnesium sulphate. After filtration and centrifugation of the solvent, purification by repeated column chromatography is effected (chloroform/methanol 15:1). The obtained oil solidifies after pasting with cyclohexane. After drying, 510 mg (73.6%) of a colourless foam is obtained.

¹H-NMR (300 MHz, CDCl₃): 1.38 (m, 6H); 2.55 (m, 1H); 2.67 (m, 1H); 4.21 (m, 5H); 4.32 (m, 2H); 4.49 (m, 1H); 6.35 (t, 1H); 6.78, (d, 1H); 7.44 (d, 1H); 7.74 (s, 1H); 8.91 (s, 1H) ppm.

³¹P-NMR (122 MHz, CDCl₃): 0.75 ppm.

1.2.4.2. cyclosaligenyl-5'-O-(E)-(2-bromovinyl)-3'-chloro-2',3'-dideoxyuridinyl-phosphate 265 mg (2.13 mmol) 2-hydroxybenzylalcohol are dissolved in 5 ml THF and cooled to −78° C. (acetone/dry ice). Thereafter, 327 mg phosphoroxychloride are added and finally 5 ml of a solution of 431 mg triethylamine in THF. After 20 min the addition is terminated. Agitation takes place for another 45 min at −78° C., then the cold bath is removed and heating to room temperature takes place. A colourless suspension is produced which is agitated for 2.5 h at room temperature.

Thereafter, cooling takes place again to −78° C. and 466 mg (5.68 mmol) N-methylimidazole is added, dissolved in 2.5 ml THF. 500 mg (1.42 mmol) 2',3'-dideoxy-3'-chloro-5-(E)-bromovinyluridine are dissolved in 10 ml THF and added in drops within 30 min. Heating to room temperature takes place gradually and agitation for another 18 h at room temperature. The reaction is terminated thereafter (DC-control with chloroform/methanol 20:1). The batch is added to a mixture of 20 ml phosphate buffer and 20 ml MTBE and extracted several times with MTBE and the combined extracts are dried with magnesium sulphate. After filtration and centrifugation of the solvent and after purification by column chromatography (chloroform/methanol 3:2), 210 mg (28.5%) of a colourless foam is obtained.

¹H-NMR (300 MHz, CDCl₃): 2.50 (m, 1H); 2.67 (m, 1H); 4.34 (m, 1H); 4.48, (m, 3H); 5.45 (m, 2H); 6.27 (m, 1H); 6.62 (m, 1H); 7.15, (m, 3H); 7.42 (m, 2H); 7.58 (m, 1H); 8.23 (s, 1H) ppm.

³¹P-NMR (122 MHz, CDCl₃): −7.84; −7.99 ppm.

1.2.4.3. phenyl-5-pivaloyl-2-thioethyl-3'-bromo-2',3'-dideoxy-5-(E)-bromovinyluridin-5'-yl-phosphate 1.50 g (9.24 mmol) S-(2-hydroxyethyl)-thiopivaloate are dissolved in 80 ml THF, cooled to −78° C. and mixed with 0.95 g (9.44 mmol) triethylamine. 1.99 g (9.44 mmol) phenyldichlorophosphate are dissolved in 5 ml THF and added in drops at −78° C. Agitation takes place for 20 h and heating to room temperature takes place gradually thereby. Thereafter filtering takes place, washing with THF (2×10 ml) and the solvent is distilled off. The yellowish oil is absorbed in 50 ml tetrachloromethane, filtered again and the residue is washed with tetrachloromethane. After withdrawing the solvent, the oily residue is dried in a vacuum. 2.55 g (phenyl-S-(2-hydroxyethyl)-thiopivaloate)-monochlorophosphate is obtained as crude product which is used without further purification.

The previously obtained crude product (2.55 g) is dissolved in 15 ml THF and thereafter 1.0 g (2.52 mmol) 2',3'-dideoxy-3'-bromo-5-(E)-bromovinyluridine are added. After 5 min agitation at room temperature, 1.24 g (15.15 mmol) N-methylimidazole are added and agitation takes place for 3 h at room temperature. The reaction is thereafter terminated (DC-control with chloroform/methanol 20:1; dichloromethane/acetone 10:1). The reaction mixture is poured into a two-phase mixture of 100 ml phosphate buffer and 60 ml acetic ester and the aqueous phase is extracted another twice with respectively 50 ml acetic ester. The combined acetic ester phases are washed with 5% citric acid, then with 5% sodium hydrogen carbonate solution and finally with saturated common salt solution. After drying with magnesium sulphate, filtering-off and distilling-off of the solvent, column chromatography is effected with chloroform/acetone 10:1. 920 mg (52.6%) of a light yellowish foam is obtained.

¹H-NMR (500 MHz, CDCl₃): 8.97 (s, 1H); 7.63 and 7.68 (s, 1H); 7.39 (m, 3H); 7.22, (m, 3H); 6.66 (d, 1H); 6.29 (m, 1H); 4.43 (m, 4H); 4.26 (m, 2H); 3.16 (m, 2H); 2.75 (m, 1H); 2.60 (m, 1H); 1.21 and 1.22 (s, 9H) ppm.

³¹P-NMR (122 MHz, CDCl₃): −5.67; −5.90 ppm.

1.3. 3'- or 5'-amino acid ester of BVDU

1.3.1. 5'-O—(N-t-butyloxycarbonyl-ε-aminocaproyl)-2'-deoxy-5-(B)-bromovinyluridine At 0° C., 7.72 g (23.2 mmol) 5-(E)-bromovinyl-2'-deoxyuridine and 9.12 g (34.8 mmol, 1.5 eq.) triphenylphosphine are placed in 80 ml DMF. Then 8.04 g (34.8 mmol, 1.5 eq.) N-t-butyloxycarbonyl-ε-aminocaproic acid and 7.03 g (34.8 mmol, 1.5 eq.) diisopropylazodicarboxylate are dissolved in 50 ml DMF and added in drops within 1 h. Subsequently the reaction mixture is agitated for 2 h at room temperature. The solvent is removed on the rotary evaporator. Purification by column chromatography (CHCl₃/MeOH, 95/5 acetic ester) yields 2.98 g (5.45 mmol, 23%) 5'-O—(N-t-butyloxycarbonyl-ε-aminocaproyl)-2'-deoxy-5-(E)-bromovinyluridine as white solid with a melting point of 121-122° C. As by-product, 1.05 g (1.92 mmol, 8%) of 3'-O—(N-t-butyloxycarbonyl-ε-aminocaproyl)-2'-deoxy-5-(E)-bromovinyluridine were able to be isolated as white solid with a melting point of 204-205° C.

5'-O—(N-t-butyloxycarbonyl-ε-aminocaproyl)-2'-deoxy-5-(E)-bromovinyluridine:

$^1$H-NMR (500 MHz, DMSO-d$_6$): 1.20-1.26 (m, 2H); 1.31-1.40 (m, 2H); 1.36 (s, 9H); 1.48-1.53 (m, 2H); 2.15-2.26 (m, 2H); 2.28-2.32 (m, 2H); 2.87 (q, 2H); 3.92 (q, 1H); 4.19-4.25 (m, 3H); 5.43 (d, 1H); 6.15 (t, 1H); 6.74 (t, 1H); 6.93 (d, 1H); 7.30 (d, 1H); 7.31 (d, 1H); 7.77 (s, 1H); 11.62 (s, 1H) ppm.

1.3.2. 3'-O—(N-t-butyloxycarbonyl-ε-aminocaproyl)-2'-deoxy-5-(E)-bromovinyluridine 3'-O—(N-t-butyloxycarbonyl-ε-aminocaproyl)-2'-deoxy-5-(E)-bromovinyluridine:

$^1$H-NMR (500 MHz, DMSO-d$_6$): 1.20-1.26 (m, 2H); 1.31-1.40 (m, 2H); 1.36 (s, 9H); 1.47-1.52 (m, 2H); 2.09-2.32 (m, 6H); 2.87 (q, 2H); 3.93-3.97 (m, 2H); 4.10-4.14 (m, 1H); 4.21-4.28 (m, 5H); 5.42 (d, 1H); 5.45 (d, 1H); 6.09-6.12 (m, 1H); 6.18-6.21 (m, 1H); 6.73 (t, 1H); 6.96 (d, 1H); 6.99 (d, 1H); 7.29-7.36 (m, 2H); 7.86 (s, 1H); 8.01 (s, 1H); 11.58 (s, 1H) ppm. A mixture of two rotational isomers is present.

1.3.3. [5'-O-(e-aminocaproyl)-2'-deoxy-5-(E)-bromovinyluridine]trifluoroacetate At 0° C., 300 mg (549 μmol) 5'-O—(N-t-butyloxycarbonyl-ε-aminocaproyl)-2'-deoxy-5-(E)-bromovinyluridine are placed in 5 ml dichloromethane, 0.4 ml (5.6 mmol) trifluoroacetic acid are added and subsequently the reaction mixture is agitated for 2 h at room temperature. The solvent is removed on the rotary evaporator. The crude product is mixed with 5 ml diethylether and agitated for 20 h at room temperature. The solvent is decanted off and the residue is left on the rotary evaporator for 1 h at 40° C. The result is 300 mg (535 μmol, 98%) [5'-O-(c-aminocaproyl)-2'-deoxy-5-(E)-bromovinyluridine]trifluoroacetate as a white solid with a melting point of 169-170° C.

$^1$H-NMR (300 MHz, DMSO-d$_6$): 1.23-1.38 (m, 2H); 1.45-1.58 (m, 4H); 2.12-2.27 (m, 2H); 2.29-2.37 (m, 2H); 2.70-2.80 (m, 2H); 3.89-3.94 (m, 1H); 4.19-4.29 (m, 3H); 5.46 (d, 1H); 6.16 (t, 1H); 6.94 (d, 1H); 7.30 (d, 1H); 7.69 (bs, 3H); 7.77 (s, 1H); 11.62 (s, 1H) ppm.

1.3.4. [3'-O-(e-aminocaproyl)-2'-deoxy-5-(E)-bromovinyluridine]trifluoroacetate At 0° C., 300 mg (549 μmol) 5'-O—(N-t-butyloxycarbonyl-ε-aminocaproyl)-2'-deoxy-5-(E)-bromovinyluridine are placed in 5 ml dichloromethane, 0.4 ml (5.6 mmol) trifluoroacetic acid are added and subsequently the reaction mixture is agitated for 2 h at room temperature. The solvent is removed on the rotary evaporator. The crude product is mixed with 5 ml diethylether and agitated for 20 h at room temperature. The solvent is decanted off and the residue is left on the rotary evaporator for 1 h at 40° C. The result is 280 mg (500 μmol, 91%) [3'-O-(e-aminocaproyl)-2'-deoxy-5-(E)-bromovinyluridine]trifluoroacetate as a white solid which decomposes at temperatures above 180° C.

$^1$H-NMR (300 MHz, DMSO-d$_6$): 1.21-1.35 (m, 2H); 1.45-1.58 (m, 4H); 2.08-2.38 (m, 6H); 2.70-2.80 (m, 2H); 3.91-3.98 (m, 2H); 4.10-4.32 (m, 6H); 5.41-5.49 (m, 2H); 6.08-6.15 (m, 1H); 6.16-6.23 (t, 1H); 6.95 (d, 1H); 7.00 (d, 1H); 7.31 (d, 1H); 7.35 (d, 1H); 7.62 (bs, 3H); 7.86 (s, 1H); 8.01 (s, 1H); 11.59 (s, 1H) ppm. The substance is present as a mixture of two rotational isomers.

1.4. 3'- or 5'-acetamido derivatives of BVDU

1.4.1. 5'-acetamido-3'-chloro-2',3',5'-trideoxy-5-(E)-bromovinyluridine

1.4.1.1. 5'-acetamido-2',5'-dideoxy-5-(E)-bromovinyluridine 1.41 g (4.26 mmol) 5'-amino-2',5'-dideoxy-5-(E)-bromovinyluridine are placed in 15 ml DMF at 0° C. and 674 mg (8.52 mmol) pyridine are added. 401 mg (5.11 mmol) acetyl chloride in 5 ml DMF are added in drops and subsequently agitated for a further 2 h. The reaction mixture is poured onto 50 g ice and adjusted to pH=7 with concentrated hydrochloric acid. The mixture is extracted three times with respectively 100 ml acetic ester. The organic phase is dried with Na$_2$SO$_4$, filtered and the solvent is removed on the rotary evaporator. Purification by column chromatography (CHCl$_3$/MeOH, 9/1) yields 870 mg (2.33 mmol, 55%) 5'-acetamido-2',5'-dideoxy-5-(E)-bromovinyluridine as white solid.

1.4.1.2. 5'-acetamido-2',3'-anhydro-2',5'-dideoxy-5-(E)-bromovinyluridine 870 mg (2.33 mmol) 5'-acetamido-2',5'-dideoxy-5-(E)-bromovinyluridine are placed in 15 ml DMF and 915 mg (3.49 mmol) PPH$_3$ are added. Subsequently 705 mg (3.49 mmol) diisopropylazodicarboxylate are dissolved in 5 ml DMF and added in drops. After an hour, the reaction mixture is poured onto 100 ml diethylether, the resulting solid is suctioned off and washed three times with 20 ml diethylether. After drying, the result is 720 mg (2.02 mmol, 87%) of 5'-acetamido-2',3'-anhydro-2',5'-dideoxy-5-(E)-bromovinyluridine as white solid.

1.4.1.3. 5'-acetamido-3'-chloro-2',3',5'-triideoxy-5-(E)-bromovinyluridine 720 mg (2.02 mmol) 5'-acetamido-2',3'-anhydro-2',5'-dideoxy-5-(E)-bromovinyluridine are placed in 10 ml DMF and 467 mg (4.04 mmol) pyridine hydrochloride are added and subsequently heating takes place for 2 h with reflux. The solvent is removed on the rotary evaporator, purification by column chromatography (CHCl$_3$/MeOH, 9/1, dichloromethane/acetic ester 1/2) yields 460 mg (1.17 mmol, 58%) 5'-acetamido-3'-chloro-2',3',5'-trideoxy-5-(E)-bromovinyluridine as white solid with a melting point of 163-165° C.

$^1$H-NMR (300 MHz, DMSO-d$_6$): 1.83 (s, 3H); 2.47-2.73 (m, 2H); 3.36-3.43 (m, 2H); 4.02 (q, 1H); 4.55 (q, 1H); 6.19 (t, 1H); 6.96 (d, 1H); 7.32 (d, 1H); 7.84 (s, 1H); 8.10 (t, 1H); 11.64 (s, 1H).

1.4.2. 3'-acetamido-5'-bromo-2',3',5'-trideoxy-5-(E)-bromovinyluridine

1.4.2.1. 3'-acetamido-2',3'-dideoxy-5-(E)-bromovinyluridine 1.00 g (2.79 mmol) 3'-azido-2',3'-dideoxy-5-(E)-bromovinyluridine are placed in 40 ml (0.1 M, pH=7.4) phosphate buffer solution. 638 mg (8.38 mmol) thioacetic acid are added and agitated at 60° C. for 30 h. The solvent is removed on the rotary evaporator. Purification by column chromatography (CHCl$_3$/MeOH, 9/1) yields 470 mg (1.26 mmol, 45%) 3'-acetamido-2',3'-dideoxy-5-(E)-bromovinyluridine as white solid.

1.4.2.2 3'-acetamido-5'-O-(methylsulphonyl)-2',3'-dideoxy-5-(E)-bromovinyluridine 500 mg (1.34 mmol) 3'-acetamido-2',3'-dideoxy-5-(E)-bromovinyluridine are placed in 5 ml pyridine at 0° C. 160 mg (1.40 mmol) methanesulphonic acid chloride in 2 ml THF are added in drops and subsequently agitated for 4 h at room temperature. The reaction mixture is poured onto ice, adjusted to pH=5 with concentrated hydrochloric acid and extracted three times with acetic ester. The organic phase is washed with diluted hydrochloric acid and saturated NACl solution, dried with $Na_2SO_4$ and the solvent is removed on the rotary evaporator. The result is 440 mg (973 μmol, 73%) 3'-acetamido-5'-O-(methylsulphonyl)-2'3'-dideoxy-5-(E)-bromovinyluridine as white solid.

1.4.2.3. 3'-acetamido-5'-bromo-2',3',5'-trideoxy-5-(E)-bromovinyluridine 440 mg (973 μmol) 3'-acetamido-5'-O-(methylsulphonyl)-2'3'-dideoxy-5-(E)-bromovinyluridine are placed in 5 ml DMF. 253 mg (2.92 mmol) LiBr are added and the reaction mixture is heated for 3 h. The solvent is removed on the rotary evaporator. The reaction mixture is absorbed in 20 ml acetic ester and the organic phase is washed with NaCl solution. The aqueous phase is extracted three times with acetic ester. The combined organic phase is washed with saturated Nacl solution, dried with $Na_2SO_4$ and the solvent is removed on the rotary evaporator. Purification by column chromatography (chloroform/methanol, 9/1) yields 290 mg (663 μmol, 68%) 3'-acetamido-5'-bromo-2',3',5'-trideoxy-5-(E)-bromovinyluridine as white solid with a melting point of 178-180° C.

$^1$H-NMR (300 MHz, DMSO-$d_6$): 1.84 (s, 3H); 2.15-2.45 (m, 2H); 3.70-3.80 (m, 2H); 3.94 (q, 1H); 4.31 (m, 1H); 6.21 (t, 1H); 6.95 (d, 1H); 7.30 (d, 1H); 7.87 (s, 1H); 8.30 (t, 1H); 11.63 (s, 1H).

2. 5'-substituted BVDU- and BVRU derivatives

2.1. 5'-halogen-BVDU

2.1.1. 2',5'-dideoxy-5'-fluoro-5-(E)-bromovinyluridine 3.5 g (7.18 mmol) 5'-O-methylsulphonyl-2'-deoxy-5-(E)-bromovinyluridine and 9.06 (28.72 mmol) tetrabutylammoniumfluoride trishydrate are dissolved in 50 ml DMF. After addition of 20 g molecular sieve (3 Å) heating to 40° C. takes place. After 4.5 h the reaction is terminated (DC-control with chloroform/methanol 10:1). Filtration takes place over celite, rewashing thoroughly with DMF and DMF is distilled off. Xylene is added as entrainer. The residue is dissolved in acetic ester and washed with 1 M hydrochloric acid. The acetic ester phase is washed with phosphate buffer, thereafter with saturated common salt solution. The combined aqueous phases are neutralised and extracted with acetic ester. All acetic ester phases are combined and dried over magnesium sulphate. After filtration and centrifugation of the solvent, purification by column chromatography is effected (chloroform/methanol 15:1) 1.05 g (43.8%) of a colourless solid with a melting point of 208° C. is obtained.

$^1$H-NMR (500 MHz, DMSO-$d_6$): 2.18 (m, 2H); 3.93 (m, 1H); 4.27 (m, 1H); 4.60 (m, 2H); 5.45 (d, 1H); 6.18 (d, 1H); 6.92 (d, 1H); 7.28 (d, 1H); 7.74 (s, 1H); 11.60 (s, 1H) ppm.

FIG. 4 shows the results of this compound according to the invention in combination with mitomycin C (MMC) in comparison with MMC alone and MMC in combination with BVDU.

2.1.2. 3'-O-methyl-5'-chloro-2',5'-dideoxy-5-(E)-bromovinyluridine 0.55 g (1.56 mmol) 2',5'-dideoxy-5'-chloro-5-(E)-bromovinyluridine is dissolved in 9 ml dioxane. 3 ml toluene, 0.03 ml water and 0.46 g (8.2 mmol) potassium hydroxide are added thereto. After 2 h a fine suspension has formed. Thereafter 0.44 g (3.12 mmol) iodomethane are added. After 1 h the same quantity of iodomethane is added and once again after a further hour. Thereafter the reaction is terminated (DC-control with chloroform/methanol 10:1). The batch is added to a two-phase mixture of 25 ml acetic ester and 25 ml phosphate buffer and the aqueous phase is extracted with acetic ester. The combined organic phases are dried with magnesium sulphate. After filtration and centrifugation of the solvent, purification by column chromatography is effected (chloroform/methanol 60:1). 430 mg (75.4%) of a colourless solid with a melting point of 145° C. is obtained.

$^1$H-NMR (500 MHz, DMSO-$d_6$): 2.30 (m, 2H); 3.31 (s, 3H); 3.86 (m, 2H); 3.99 (m, 1H); 4.11 (m, 1H); 6.12 (m, 1H); 6.90 (d, 1H); 7.29 (d, 1H); 7.82 (s, 1H); 11.65 (s, 1H) ppm.

2.1.3. 3'-O-methyl-5'-fluoro-2',5'-dideoxy-3-methyl-5-(E)-bromovinyluridine 1.24 g (3.7 mmol) 2',5'-dideoxy-5'-fluoro-5-(E)-bromovinyluridine are dissolved in 40 ml dioxane and mixed with 15 ml toluene. Thereafter 1.12 g (20 mmol) potassium hydroxide are added and 65 μl water. Agitation takes place for 2 h at room temperature and a fine suspension is obtained. 1.57 g methyl iodide are added hereto and, after 2 h and 4 h agitation, the same quantity of methyl iodide again. After 16 h agitation at room temperature, the conversion is complete (DC-control with chloroform/methanol 10:1). The reaction mixture is poured into 100 ml phosphate buffer solution and extracted with acetic ester (3×50 ml). The combined extracts are dried with magnesium sulphate. After filtration and centrifugation of the solvent, purification by column chromatography is effected (dichloromethane/acetone 50:1; cyclohexane/acetic ester 1:1). From the concentrated solution, the product is precipitated with cyclohexane and dried. 0.63 g (46.9%) of a colourless solid with a melting point of 95° C. is obtained.

$^1$H-NMR (500 MHz, DMSO-$d_6$): 2.24 (m, 1H); 2.35 (m, 1H); 3.18 (s, 3H); 3.30 (s, 3H); 4.05 (m, 1H); 4.19 (m, 1H); 4.61 (m, 1H); 4.71 (m, 1H); 6.15 (t, 1H); 6.94 (d, 1H); 7.33 (d, 1H); 7.82 (s, 1H) ppm.

2.1.4. 3'-O-methyl-5'-fluoro-2',5'-dideoxy-5-(E)-bromovinyluridine

2.1.4.1. 5'-O-(4,4'-dimethoxytrityl)-2'-deoxy-5-(E)-bromovinyluridine 8.20 g (24.6 mmol) 2'-deoxy-5-(E)-bromovinyluridine are dissolved in 100 ml pyridine. 0.75 g (6.15 mmol) 4-N,N-dimethylaminopyridine and 5.06 g (50 mmol) triethylamine are added thereto. Cooling to 0° C. takes place and two portions of respectively 5 g (in total 10.0 g, 29.51 mmol) 4,4'-dimethoxytritylchloride are added. Agitation takes place for 30 min, the cooling bath is then removed and heating to room temperature takes place. After 22 h the conversion is complete (DC-control with dichloromethane/methanol 15:1). After the addition of 30 ml ethanol and 20 min agitation, pyridine is distilled off several times with toluene. The obtained dark brown oil is dissolved in acetic ester (200 ml) and washed with 5% potassium hydrogen carbonate solution. The aqueous phase is extracted another three times with acetic ester and all the acetic ester phases are combined and dried with magnesium sulphate. After filtration and distilling-off of the solvent, purification by column chromatography is effected (dichloromethane/methanol 35:1 with 1% triethylamine). 13.57 g (86.8%) of a colourless foam is obtained.

2.1.4.2. 3'-O-methyl-5'-O-(4,4'-dimethoxytrityl)-2'-deoxy-5-(E)-bromovinyluridine 7.5 g (11.8 mmol) 5'-O-(4,4'-dimethoxytrityl)-2'-deoxy-5-(E)-bromovinyluridine are dissolved in a mixture of 150 ml dioxane and 50 ml toluene and 3.37 g (60 mmol) potassium hydroxide and 0.29 ml water are added thereto. After agitation for 2 h at room temperature, a fine colourless suspension is obtained. 6.71 g (47.3 mmol) methyl iodide are added thereto and left to agitate for 1 h. Thereafter the same quantity of methyl iodide is added once again and half the quantity of methyl iodide after a further 2 h. After 1.5 h the conversion is complete (DC-control with dichloromethane/methanol 20:1; chloroform/methanol 20:1). The batch is poured into 200 ml phosphate buffer solution and thereafter is extracted several times with acetic ester. The combined extracts are dried with magnesium sulphate and purification by column chromatography is effected after centrifugation of the solvent (dichloromethane/methanol 50:1). 6.32 g (82.5%) of a yellowish foam is obtained.

2.1.4.3. 3'-O-methyl-2'-deoxy-5-(E)-bromovinyluridine 6.32 g (9.72 mmol) 3'-O-methyl-5'-O-(4,4'-dimethoxytrityl)-2'-deoxy-5-(E)-bromovinyluridine are dissolved in 120 ml chloroform. 60 ml methanol are added thereto and, after cooling to 0° C., 1.85 g (9.72 mmol) 4-methylsulphonic acid monohydrate. After 1 h (DC-control with dichloromethane/methanol 15:1), the reaction is terminated. 2.3 g (23 mmol) potassium hydrogen carbonate are added, agitated for five min and mixed with 200 ml saturated common salt solution. Extraction takes place with chloroform and acetic ester, all the extracts are combined and dried with magnesium sulphate. After filtration and distilling-off of the solvent, extraction with cyclohexane, filtration and washing of the residue with cyclohexane takes place. After drying, 3.33 g (98.5%) of a colourless solid is obtained.

2.1.4.4. 5'-O-(4-methylbenzenesulphonyl)-3'-O-methyl-2'-deoxy-5-(E)-bromovinyluridine 3.33 g (9.6 mmol) 3'-O-methyl-2'-deoxy-5-(E)-bromovinyluridine are dissolved in 30 ml pyridine and the obtained solution is cooled to 0° C. Thereafter 2.2 g 4-methylbenzenesulphonyl chloride are added, left to agitate for 30 min at 0° C. and then heated to room temperature. After 7 h, 1.55 g (8.13 mmol) 4-methylbenzenesulphonyl chloride are added once again and agitated for 20 h. The conversion is then complete (DC-control with dichloromethane/methanol 15:1). This is poured on ice, agitated for 30 min and acidified with 6 M hydrochloric acid. After extraction with acetic ester, the combined extracts are washed with 1 M hydrochloric acid, thereafter with phosphate buffer and dried with magnesium sulphate. After distilling-off of the solvent and purification by column chromatography (cyclohexane/acetone 2:1), 3.32 g (68.9%) of a colourless solid is obtained.

2.1.4.5. 3'-O-methyl-5'-fluoro-2',5'-dideoxy-5-(E)-bromovinyluridine 2.5 g (4.98 mmol) 5'-O-(4-methylbenzenesulphonyl)-3'-O-methyl-2'-deoxy-5-(E)-bromovinyluridine are dissolved in 40 ml DMF and 6.27 g (20 mmol) tetra-n-butylammoniumfluoridetrishydrate and 15 g molecular sieve (3 Å) are added. Heating takes place to 35° C. After 1 h the reaction is terminated (DC-control cyclohexane/acetic ester 1:1). Filtration over celite takes place and subsequently washing with DMF. DMF is removed by distilling-off with xylene, the residue is dissolved in acetic ester and washed with 1 M hydrochloric acid (80 ml). The aqueous phase is extracted with acetic ester and all the combined acetic ester phases are washed with phosphate buffer solution. After drying the organic phase with magnesium sulphate and distilling-off of the solvent, purification by column chromatography is effected with cyclohexane/acetic ester 1:1. 0.99 g (56.9%) of a colourless solid with a melting point of 177° C. is obtained.

$^1$H-NMR (500 MHz, DMSO-$d_6$): 2.23 (m, 1H); 2.34 (m, 1H); 3.30 (s, 3H); 4.14 (m, 1H); 4.32 (m, 1H); 4.58 (m, 1H); 4.68 (m, 1H); 6.12 (m, 1H); 6.81 (d, 1H); 7.28 (d, 1H); 7.76 (s, 1H); 11.63 (s, 1H) ppm.

2.2. ester of 5'-halogen-BVDU

2.2.1. 3'-O-acetyl-5'-fluoro-2'-deoxy-5-(E)-bromovinyluridine 300 mg (0.9 mmol) 2',5'-dideoxy-5'-fluoro-5-(E)-bromovinyluridine are suspended in a mixture of 5 ml dichloromethane and 1 ml pyridine, cooled to 0° C. and mixed with 190 mg (2.4 mmol) acetyl chloride. After 2 h the conversion is complete (DC-control with chloroform/methanol 15:1). Dilution takes place with 25 ml acetic ester and the organic phase is washed with 2×25 ml 0.1 M hydrochloric acid. Washing takes place neutrally with phosphate buffer. After drying over magnesium sulphate, filtering-off and centrifugation of the solvent, purification by column chromatography is effected (dichloromethane/acetic ester 4:1). After precipitation from t-butylmethyl ether/cyclohexane, 90 mg (27%) of a colourless solid with a melting point of 81° C. is obtained.

$^1$H-NMR (500 MHz, DMSO-$d_6$): 2.07 (s, 3H); 2.42 (m, 2H); 4.25 (m, 1H); 4.70 (m, 2H); 5.24 (m, 1H); 6.16 (m, 1H); 6.92 (d, 1H); 7.30 (d, 1H); 7.81 (s, 1H); 11.66 (s, 1H) ppm.

2.2.2. amino acid ester of 5'-halogen-BVDU

2.2.2.1. 4-(t-butoxycarbonyl)amino-1-(5'-fluoro-2',5'-dideoxy-5-(E)-bromovinyluridin-3'-yl)butanoate 280 mg (1.33 mmol) N—BOC-4-aminobutanoic acid and 290 mg (2.39 mmol) 40 dimethylaminopyridine are dissolved in 20 ml dichloromethane. 400 mg (1.19 mmol) 2',5'-dideoxy-5'-fluoro-5-(E)-bromovinyluridine and 280 mg (1.34 mmol) N,N'-dicyclohexylcarbodiimide are added thereto. After 2 h the reaction is terminated (DC-control with chloroform/methanol 15:1). The batch is filtered and centrifuged. After dissolving in acetic ester, cooling takes place to −20° C., the precipitate is filtered off and washed with a little acetic ester cooled to −20° C. The filtrate is centrifuged and purified several times by column chromatography with dichloromethane/methanol (30:1). 400 mg (64.1%) of a colourless foam is obtained.

¹H-NMR (500 MHz, DMSO-d₆): 1.37 (s, 9H); 1.62 (m, 2H); 2.37 (m, 2H); 2.40 (m, 1H); 2.51 (m, 1H); 2.94 (m, 2H); 4.25 (m, 1H); 4.68 (m, 2H); 5.24 (m, 1H); 6.18 (m. 1H); 6.84 (t, 1H); 6.91 (d, 1H); 7.28 (d, 1H); 7.83 (s, 1H); 11.66 (s, 1H) ppm.

2.2.2.2. 4-ammonium-1-(5'-fluoro-2',5'-dideoxy-5-(E)-bromovinyluridin-3'-yl)butanoate-trifluoroacetate 290 mg (0.56 mmol) product from 2.2.2.1. are dissolved in 5 ml dichloromethane and mixed with 5 ml trifluoroacetic acid. After 30 min the conversion is terminated (DC-control with dichloromethane/methanol 25:1). After multiple centrifugation with dichloromethane, the residue is treated with diethylether and the colourless residue is filtered off and washed with diethylether. After drying, 270 mg (90.6%) of a colourless powder with a melting point of 129° C. is obtained.

¹H-NMR (500 MHz, DMSO-d₆): 11.75 (s, 1H); 7.82 (s, 1H); 7.71 (s (br.), 3H); 7.29 (d, 1H); 6.91 (d, 1H); 6.18 (m, 1H); 5.27 (m, 1H); 4.74 (m, 1H); 4.67 (m, 1H); 4.24 (m, 1H); 2.83 (m, 2H); 2.44 (m, 3H); 2.37 (m, 1H); 1.80 (m, 2H); ppm.

2.2.2.3. 4-(t-butoxycarbonyl)amino-1-(5'-chloro-2',5'-dideoxy-5-(E)-bromovinyluridin-3'-yl)butanoate 500 mg (1.42 mmol) 5'-chloro-2',5'-dideoxy-5-(E)-bromovinyluridine, 290 mg (1.42 mmol N—BOC-4-aminobutanoic acid) and 175 mg (1.42 mmol) 4-dimethylaminopyridine are added to 12 ml dichloromethane, the obtained suspension is cooled to 0° C. and thereafter 423 mg (1.42 mmol) 1-(3-dimethylaminopropyl)-3-ethylcarbodiimide methiodide are added. After removing the cold bath, agitation takes place for 6 h. Thereafter the reaction is terminated (DC-control with chloroform/methanol 10:1). Dichloromethane is centrifuged off and the residue is absorbed in acetic ester. The organic phase is washed several times with saturated common salt solution. The combined aqueous phases are extracted with acetic ester. All the organic phases are combined and dried with magnesium sulphate. After filtration and centrifugation of the solvent, purification by column chromatography is effected (dichloromethane/methanol 50:1; cyclohexane/acetic ester 1:1). 520 mg (68.2%) of a colourless foam is obtained.

¹H-NMR (500 MHz, DMSO-d₆): 1.37 (s, 9H); 1.64 (m, 2H); 2.36 (m, 3H); 2.51 (m, 1H); 2.94 (m, 2H); 3.91 (m, 2H); 4.21 (m, 1H); 5.24 (m, 1H); 6.18 (m, 1H); 6.82 (t, 1H); 6.91 (d, 1H); 7.29 (d, 1H); 7.87 (s, 1H); 11.67 (s, 1H) ppm.

2.2.2.4. 4-ammonium-1-(5'-chloro-2',5'-dideoxy-5-(E)-bromovinyluridin-3'-yl)butanoate-trifluoroacetate 200 mg (0.372 mmol) 4-(t-butoxycarbonyl)amino-1-(5'-chloro-2',5'-dideoxy-5-(E)-bromovinyluridin-3'-yl)butanoate are dissolved in 4 ml dichloromethane, thereafter 7 ml trifluoroacetic acid are added. After 30 min everything is converted (DC-control with cyclohexane/acetic ester 1:1). After multiple centrifugation with dichloromethane, the residue is treated with diethylether and the colourless precipitate is filtered off and dried. 160 mg (78.0%) of a colourless powder with a melting point of 148° C. is obtained.

¹H-NMR (500 MHz, DMSO-d₆): 11.75 (s, 1H); 7.87 (s, 1H); 7.72 (s, 3H); 7.30 (d, 1H); 6.91 (d, 1H); 6.20 (m, 1H); 5.25 (m, 1H); 4.21 (m, 1H); 3.91 (m, 2H); 2.83 (m, 2H); 2.35 (m, 4H); 1.81 (m, 2H) ppm.

FIG. 5 shows the results of this compound according to the invention in combination with mitomycin C (MMC) in comparison with MMC alone and MMC in combination with BVDU.

2.2.2.5. 3'-O—(N-4-butyloxycarbonyl-L-valinoyl)-5'-chloro-2',5'-dideoxy-5-(E)-bromovinyluridine At 0° C., 1.00 g (2.84 mmol) 5'-chloro-2',5'-dideoxy-5-(E)-bromovinyluridine are placed in 20 ml dichloromethane. Then 618 mg (2.84 mmol, 1.0 eq.) N-t-butyloxycarbonyl-L-valine, 347 mg (2.84 mmol, 1.0 eq.) N,N-dimethylaminopyridine and also 587 mg (2.84 mmol 1.0 eq.) N,N'-dicyclohexylcarbodiimide are added and subsequently the reaction mixture is agitated for 20 h at room temperature. The resulting precipitate is filtered off and washed with dichloromethane. The filtrate is washed with diluted citric acid solution, NaHCO₃ solution and also NaCl solution and subsequently dried with Na₂SO₄. The solvent is removed on the rotary evaporator. Purification by column chromatography (CHCl₃/MeOH, 95/5, dichloromethane/acetic ester, 3/1) yields 1.00 g (1.82 mmol, 64%) 3'-O—(N-t-butyloxycarbonyl-L-valinoyl)-5'-chloro-2',5'-dideoxy-5-(E)-bromovinyluridine as a white solid with a melting point of 87-88° C.

¹H-NMR (500 MHz, DMSO-d₆): 0.89-0.91 (m, 6H); 1.39 (s, 9H); 2.03 (m, 1H); 2.31 (m, 1H); 2.53 (m, 1H); 3.83 (t, 1H); 3.88-3.91 (m, 2H); 4.12 (m, 1H); 5.28 (m, 1H); 6.22 (t, 1H); 6.91 (d, 1H); 7.29 (d, 1H); 7.32 (d, 1H); 7.87 (s, 1H); 11.68 (s, 1H) ppm.

2.2.2.6. (5'-chloro-2',5'-dideoxy-3'-O-L-valinoyl-5-(E)-bromovinyluridine)trifluoroacetate At 0° C., 600 mg (1.09 mmol) 3'-O—(N-t-butyloxycarbonyl-L-valinoyl)-5'-chloro-2',5'-dideoxy-5-(E)-bromovinyluridine are placed in 5 ml dichloromethane, 1.0 ml (14 mmol) trifluoroacetic acid are added and subsequently the reaction mixture is agitated for 2 h at room temperature. The solvent is removed on the rotary evaporator. The crude product is mixed with 5 ml diethylether and agitated for 20 h at room temperature. The solvent is decanted off and the residue is left on the rotary evaporator for 1 h at 40° C. The result is 450 mg (797 µmol, 73%) (5'-chloro-2',5'-dideoxy-3'-O-L-valinoyl-5-(E)-bromovinyluridine) trifluoroacetate as a white solid with a melting point of 108-109° C.

¹H-NMR (500 MHz, DMSO-d₆): 0.97-1.01 (m, 6H); 2.19 (m, 1H); 2.37 (m, 1H); 2.58 (m, 1H); 3.89-3.97 (m, 2H); 4.00 (bs, 1H); 4.27 (m, 1H); 5.39 (m, 1H); 6.25 (dd, 1H); 6.92 (d, 1H); 7.31 (d, 1H); 7.87 (s, 1H); 8.37 (bs, 3H); 11.71 (s, 1H) ppm.

2.2.2.7. 3'-O—(N-t-butyloxycarbonyl-L-valyl-L-valinoyl)-5'-chloro-2',5'-dideoxy-5-(E)-bromovinyluridine At 0° C., 1.00 g (2.84 mmol) 5'-chloro-2',5'-dideoxy-5-(E)-bromovinyluridine are placed in 20 ml dichloromethane. Then 900 mg (2.84 mmol, 1.0 eq.) N-t-butyloxycarbonyl-L-valyl-L-valine, 347 mg (2.84 mmol, 1.0 eq.) N,N-dimethylaminopyridine and also 587 mg (2.84 mmol, 1.0 eq.) N,N'-dicyclohexylcarbodiimide are added and subsequently the reaction mixture is agitated for 24 h at room temperature. The resulting precipitate is filtered off and washed with dichloromethane. The filtrate is washed with diluted citric acid solution, NaHCO₃ solution and also NaCl solution and subsequently dried with Na₂SO₄. The solvent is removed on the rotary evaporator. Purification by column chromatography (dichloromethane/acetic ester, 3/1) yields 850 mg (1.31 mmol, 46%) 3'-O—(N-t-butyloxycarbonyl-L-valyl-L-valinoyl)-5'-chloro-2',5'-dideoxy-5-(E)-bromovinyluridine as a white solid with a melting point of 114-116° C.

$^1$H-NMR (500 MHz, DMSO-d$_6$): 0.83-0.93 (m, 12H); 1.37 (s, 9H); 1.91 (m, 1H); 2.09 (m, 1H); 2.30 (m, 1H); 3.88-3.91 (m, 3H); 4.13-4.22 (m, 2H); 5.27 (m, 1H); 6.20 (m, 1H); 6.70 (m, 1H); 6.91 (d, 1H); 7.30 (d, 1H); 7.87 (s, 1H); 8.15 (m, 1H); 11.68 (s, 1H) ppm.

2.2.2.8. [5'-chloro-2',5'-dideoxy-3'-O-(L-valyl-L-valinoyl)-5-(E)-bromovinyluridine]trifluoroacetate At 0° C., 200 mg (308 µmol) 3'-O—(N-t-butyloxycarbonyl-L-valyl-L-valinoyl)-5'-chloro-2',5'-dideoxy-5-(E)-bromovinyluridine are placed in 5 ml dichloromethane, 0.35 ml (4.7 mmol) trifluoroacetic acid are added and subsequently the reaction mixture is agitated for 3 h at room temperature. The solvent is removed on the rotary evaporator. The crude product is mixed with 5 ml diethylether and agitated for 1 h at room temperature. The solvent is decanted off and the residue is left on the rotary evaporator for 1 h at 40° C. The result is 180 mg (271 µmol, 88%) [5'-chloro-2',5'-dideoxy-3'-O-(L-valyl-L-valinoyl)-5-(E)-bromovinyluridine]trifluoroacetate as a white solid with a melting point of 135-136° C.

$^1$H-NMR (500 MHz, DMSO-d$_6$): 0.92-0.99 (m, 12H); 2.08-2.18 (m, 2H); 2.35 (m, 1H); 2.55 (m, 1H); 3.73 (m, 1H); 3.91 (m, 1H); 4.17 (m, 1H); 4.28 (m, 1H); 5.31 (m, 1H); 6.21 (m, 1H); 6.91 (d, 1H); 7.31 (d, 1H); 7.87 (s, 1H); 8.10 (bs, 3H); 8.73 (d, 1H); 11.70 (s, 1H) ppm.

2.2.2.9. 5'-azido-3'-O—(N-t-butyloxycarbonyl-L-valyl-L-valinoyl)-2',5'-dideoxy-5-(E)-bromovinyluridine At 0° C., 1.10 g (3.07 mmol) 5'-azido-2',5'-dideoxy-5-(E)-bromovinyluridine are placed in 20 ml dichloromethane. Then 950 mg (3.07 mmol, 1.0 eq.) N-t-butyloxycarbonyl-L-valyl-L-valine, 375 mg (3.07 mmol, 1.0 eq.) N,N-dimethylamino-pyridine and also 634 mg (3.07 mmol, 1.0 eq.) N,N'-dicyclohexylcarbodiimide are added and subsequently the reaction mixture is agitated for 2 d at room temperature. The resulting precipitate is filtered off and washed with dichloromethane. The filtrate is washed with diluted citric acid solution, NaHCO$_3$ solution and also NaCl solution and subsequently dried with Na$_2$SO$_4$. The solvent is removed on the rotary evaporator. Purification by column chromatography (dichloromethane/acetic ester, 2/1) yields 600 mg (914 µmol, 30%) 5'-azido-3'-O—(N-t-butyloxycarbonyl-L-valyl-L-valinoyl)-2',5'-dideoxy-5-(E)-bromovinyluridine as a white solid with a melting point of 133-135° C.

$^1$H-NMR (300 MHz, DMSO-d$_6$): 0.83-0.94 (m, 12H); 1.38 (s, 9H); 1.93 (m, 1H); 2.10 (m, 1H); 2.34 (m, 1H); 2.53 (m, 1H); 3.58-3.76 (m, 2H); 3.91 (m, 1H); 4.04-4.24 (m, 2H); 5.24 (m, 1H); 6.22 (m, 1H); 6.72 (m, 1H); 6.94 (d, 1H); 7.32 (d, 1H); 7.92 (s, 1H); 8.14 (m, 1H); 11.70 (s, 1H) ppm. A mixture of two rotational isomers in the ratio 1:1 is present, for which reason some signals occur twice.

2.2.2.10. [5'-azido-2',5'-dideoxy-a-O-(L-valyl-L-valinoyl)-5-(E)-bromovinyluridine]trifluoroacetate At 0° C., 200 mg (305 µmol) 5'-azido-3'-O—(N-t-butyloxycarbonyl-L-valyl-L-valinoyl)-2',5'-dideoxy-5-(E)-bromovinyluridine are placed in 5 ml dichloromethane, 0.33 ml (4.47 mmol) trifluoroacetic acid are added and subsequently the reaction mixture is agitated for 4 h at room temperature. The solvent is removed on the rotary evaporator. The crude product is mixed with 5 ml diethylether and agitated for 20 h at room temperature. The solvent is decanted off and the residue left on the rotary evaporator for 1 h at 40° C. The result is 160 mg (239 µmol, 78%) [5'-azido-2',5'-dideoxy-3'-O-(L-valyl-L-valinoyl)-5-(E)-bromovinyluridine]trifluoroacetate as a white solid with a melting points of 122-124° C.

$^1$H-NMR (300 MHz, DMSO-d$_6$): 0.92-0.99 (m, 12H); 2.09-2.18 (m, 2H); 2.25-2.40 (m, 1H); 2.50-2.62 (m, 1H); 3.56-3.80 (m, 3H); 4.04-4.15 (m, 1H); 4.22-4.29 (m, 1H); 5.25 (m, 1H); 6.20 (m, 1H); 6.92 (d, 1H); 7.31 (d, 1H); 7.91 (s, 1H); 8.10 (bs, 3H); 8.68 (d, 1H); 11.69 (s, 1H) ppm. A mixture of two rotational isomers in the ratio 1:2 is present, for which reason some signals occur twice.

2.2.3. phosphoramidates of 5'-halogen-BVDU

2.2.3.1. (E)-5-(2-bromovinyl)-5'-chloro-2',5'-dideoxyuridine-3'-[phenyl-(methoxy-L-alaninyl)]-phosphate 1.55 g (7.35 mmol) phenyldichlorophosphate and 1.03 g (7.35 mmol) L-alaninemethylester hydrochloride are dissolved or suspended in 15 ml dichloromethane and cooled to −78° C. Triethylamine (1.52 g (15 mmol)) is dissolved in 15 ml dichloromethane and added in drops at −78° C. within 2 h. After the addition in drops, heating to room temperature takes place and agitation for 18 h. Dichloromethane is centrifuged off, the residue is absorbed in diethylether and filtered from the undissolved part. Diethylether is thereafter withdrawn and the oily crude product is further processed without purification.

0.57 g (1.62 mmol) 2',5'-dideoxy-5'-chloro-5-(E)-bromovinyluridine and the previously obtained crude product are dissolved in 15 ml THF and the solution is cooled to −78° C. 0.82 g (10 mmol) N-methylimidazole are dissolved in 5 ml THF and added in drops within 20 min. Heating to room temperature takes place gradually and agitation for another 20 h at this temperature. The reaction is thereafter complete (DC-control with chloroform/methanol 10:1). The batch is added to a two-phase mixture of phosphate buffer and acetic ester and the aqueous phase is extracted several times with acetic ester. The combined extracts are dried with magnesium sulphate, filtered and the solvent is centrifuged off. After purification by column chromatography (dichloromethane/methanol 30:1; chloroform/acetone 5:1), 0.62 g (64.6%) of a colourless foam is obtained.

$^1$H-NMR (500 MHz, CDCl$_3$): 8.56 (s, 1H); 8.55* (s, 1H); 7.66 (s, 1H); 7.63* (s, 1H); 7.35 (m, 3H); 7.22 (m, 3H); 6.68 (d, 1H); 6.66* (d, 1H); 6.30 (m, 1H); 5.11 (m, 1H); 4.50* (m, 1H); 4.37 (m, 1H); 4.02 (m, 1H); 3.91* (m, 2H); 3.83 (m, 2H), 3.76* (s, 3H); 3.73 (s, 3H); 3.71* (m, 1H); 3.63 (m, 1H); 2.65 (m, 1H); 2.58* (m, 1H); 2.25 (m, 1H): 1.40 (d, 3H) ppm.

The substance comprises a diastereomer mixture (ratio approx. 1.2:1). The NMR signals marked with a * relate to the diastereomer which is present in a fairly small proportion.

$^{31}$P-NMR (202 MHz, CDCl$_3$); 2.31; 1.61 ppm

FIG. 6 shows the results of this compound according to the invention in combination with mitomycin C (MMC) in comparison with MMC alone and MMC in combination with BVDU.

2.2.3.2. [-5-(E)-bromovinyl-5'-fluoro-2',5'-dideoxyuridin]-3'-yl-(methoxy-L-alaninyl)-phenylphosphate 600 mg (2.84 mmol, 2 eq.) phenyldichlorophosphate and 397 mg (2.84 mmol, 2 eq.) L-alaninemethylester hydrochloride are placed in 7 ml THF at −78° C. 576 mg (5.69 mol, 4 eq.) triethylamine are dissolved in 7 ml THF, added in drops within 30 min and subsequently agitated for 20 h at room temperature. The reaction mixture is cooled to −78° C. and 477 mg (1.42 mmol). 2',5'-dideoxy-5'-fluoro-5-(E)-bromovinyluridine are added. There is added to the obtained suspension in drops a solution of 700 mg (8.53 mmol, 6 eq.) N-methylimidazole in 7 ml THF within 30 min and subsequently agitation takes place for 20 h at room temperature. The batch is added to a mixture of 25 ml phosphate buffer and 25 ml acetic ester and the aqueous phase is extracted another twice with respectively 20 ml acetic ester. The combined organic phase is dried over $Na_2SO_4$, filtered and the solvent is removed on the rotary evaporator. Purification by column chromatography (dichloromethane/acetic ester, 1/1; acetic ester) yields 310 mg (523 μmol, 37%) [5-(E)-bromovinyl-5'-fluoro-2',5'-dideoxyuridin]-3'-yl-(methoxy-L-alaninyl]-phenylphosphateas white solid.

$^1$H-NMR (300 MHz, DMSO-$d_6$): 1.22 (d, 3H); 1.25* (d, 3H); 2.40-2.59 (m, 4H); 3.61 (s, 3H); 3.62 (8 s, 3H); 3.81-3.98 (m, 2H); 4.19-4.35 (m, 2H); 4.52-4.82 (m, 4H); 5.00-5.12 (m, 2H); 6.13-6.26 (m, 4H); 6.89* (d, 1H); 6.93 (d, 1H); 7.16-7.43 (m, 12H); 7.79* (s, 1H); 7.80 (s, 1H); 11.67* (s, 1H); 11.68 (s, 1H) ppm.

The substance comprises a diastereomer mixture (ratio approx. 1.2:1). The signals characterised with * relate to the deficit isomer.

$^{31}$P-NMR (122 MHz, DMSO-$d_6$): 3.91; 4.54 ppm.

2.2.3.3. [5'azido-5-(E)-bromovinyl-'2,'5-dideoxyuridine]-3'-yl-(methoxy-L 600 mg (2.84 mmol, 2 eq.) phenyldichlorophosphate and 397 mg (2.84 mmol, 2 eq.) L-alaninemethyl ester hydrochloride are placed in 7 ml THF at −78° C. 576 mg (5.69 mmol, 4 eq.) triethylamine are dissolved in 7 ml THF, added in drops within 30 min and subsequently agitated for 20 h at room temperature. The reaction mixture is cooled to −78° C. and 509 mg (1.42 mmol) 5'-azido-2',5'-dideoxy-5-(E)-bromovinyluridine are added. There is added to the obtained suspension in drops a solution of 700 mg (8.53 mmol, 6 eq.) N-methylimidazole in 7 ml THF within 30 min and subsequently agitation takes place for 20 h at room temperature. The batch is added to a mixture of 25 ml phosphate buffer and 25 ml acetic ester and the aqueous phase is extracted another twice with respectively 20 ml acetic ester. The combined organic phase is dried over $Na_2SO_4$, filtered and the solvent is removed on the rotary evaporator. Purification by column chromatography (dichloromethane/acetic ester, 1/1; acetic ester) yields 160 mg (267 μmol, 19%) [5'-azido-5-(E)-bromovinyl-2',5'-dideoxyuridin]-3'-yl-(methoxy-L-alaninyl)-phenylphosphate as white solid.

$^1$H-NMR (500 MHz, DMSO-$d_6$): 1.22 (d, 3H); 1.25* (d, 3H); 2.35-2.58 (m, 4H); 3.57-3.70 (m, 4H); 3.62 (s, 6H); 3.87-3.92 (m, 2H); 4.13-4.18 (m, 2H); 4.94-4.99* (m, 1H); 5.00-5.05 (m, 1H); 6.14-6.22 (m, 4H); 6.90* (d, 1H); 6.93 (d, 1H); 7.16-7.24 (m, 6H); 7.28-7.32 (m, 2H); 7.36-7.42 (m, 4H), 7.88* (s, 1H); 7.89 (s, 1H); 11.69 (s, 2H) ppm.

The substance comprises a diastereomer mixture (ratio approx. 1.5:1). The signals characterised with * relate to the deficit isomer.

$^{31}$P-NMR (122 MHz, DMSO-$d_6$): 3.93; 4.54 ppm.

2.3. 5'bromo-5'-deoxy-5-(E)-bromovinyluridine

2.3.1. 2',3'-O-isopropylidene-5-(E)-bromovinyluridine 1.0 g (2.86 mmol) 5-(E)-bromovinyluridine are suspended in 15 ml acetone. 3.13 g (30 mmol) 2,2-dimethoxypropane and 0.05 g p-toluenesulphonic acid are added thereto. After 2 h the reaction is complete (DC-control with chloroform/methanol 20:1). 0.50 g potassium hydrogen carbonate, 20 ml water and 25 ml acetic ester are added, the phases are separated and the aqueous one is extracted several times with acetic ester. The combined organic phases are dried with magnesium sulphate. After filtering-off of the drying agent and distilling-off of the solvent, purification by column chromatography is effected with chloroform/methanol 30:1. 0.57 g (51.2%) of a colourless foam is obtained.

2.3.2. 2',3'-O-isopropylidene-5'-bromo-5'-deoxy-5-(E)-bromovinyluridine 0.57 g (1.46 mmol) 2',3'-O-isopropylidene-5-(E)-bromovinyluridine and 0.81 g (3.1 mmol) triphenylphosphine are dissolved in 12 ml pyridine. There is added in drops a solution of 0.92 g (2.77 mmol) tetrabromomethane in 8 ml pyridine. After 90 min the conversion is complete (DC-control with chloroform/methanol 30:1). Pyridine is distilled off with acetic ester and the residue is purified by column chromatography with dichloromethane/acetic ester 12:1). 380 mg (57.7%) of a colourless foam is obtained.

2.3.3. 5'-bromo-5'-deoxy-5-(E)-bromovinyluridine 0.38 g (0.84 mmol) 2',3'-O-isopropylidene-5'-bromo-5'-deoxy-5-(E)-bromovinyluridine are dissolved in 5 ml trifluoroacetic acid and 1 ml water and dissolved for 30 min at room temperature. The conversion is thereafter complete (DC-control with chloroform/methanol 30:1). This is evaporated until dry, absorbed several times in methanol and evaporated again. After purification by column chromatography, 0.25 g (72.2%) of a colourless solid with a melting point of 201° C. is obtained.

$^1$H-NMR (500 MHz, DMSO-$d_6$): 3.71 (m, 1H); 3.81 (m, 1H); 3.99 (m, 2H); 4.19 (m, 1H); 5.41 (d, 1H); 5.55 (d, 1H); 5.82 (d, 1H); 6.93 (d, 1H); 7.30 (d, 1H); 7.81 (s, 1H); 11.68 (s, 1H) ppm.

2.4. 5'- or 3'-phosphoramidites of BVDU

2.4.1. [5-(E)-bromovinyl-5'-methoxy-2'-deoxyuridin]-3'-yl-(2-cyanoethyl)-diisopropyl phosphoramidite

2.4.1.1. 3'-O-(t-butyldimethylsilyl)-5'-methoxy-2'-deoxy-5-(E)-bromovinyluridine 1.33 g (2.97 mmol) 3'-O-(t-butyldimethylsilyl)-2'-deoxy-5-(E)-bromovinyluridine are dissolved in 17 ml dioxane and 6 ml toluene and 0.88 g (15.6 mmol) KOH and also 60 μl (3.3 mmol) water are added. The reaction mixture is agitated for 2½ h at room temperature and subsequently 0.85 g (6.0 mmol) MeI are added. After a further 3 h agitation, 120 ml phosphate buffer solution (pH=7) are added and the mixture is extracted three times with 50 ml acetic ester. The combined organic phase is dried over $MgSO_4$, filtered and the solvent is removed on the rotary evaporator. Purification by column chromatography (chloroform/methanol 100/1) yields 1.04 g (2.25 mmol, 76%) 3'-O-(t-butyldimethylsilyl)-5'-methoxy-2'-deoxy-5-(E)-bromovinyluridine as white solid.

2.4.1.2. 2'-deoxy-5'-methoxy-5-(E)-bromovinyluridine 26.2 g (5.68 mmol) 3'-O-(t-butyldimethylsilyl-5'-methoxy-2'-deoxy-5-(E)-bromovinyluridine are dissolved in 25 ml THF and 2.69 g (8.52 mmol) tetrabutylammonium fluoride in 25 ml THF is added in drops. The reaction mixture is agitated for 4 h at room temperature and subsequently the solvent is removed on the rotary evaporator. Purification by column chromatography (chloroform/methanol 25/1 yields 1.73 g (4.98 mmol, 88%) 2'-deoxy-5'-methoxy-5-(E)-bromovinyluridine as white solid.

2.4.1.3. [5-(E)-bromovinyl-5'-methoxy-2'-deoxyuridin]-3'-yl-(2-cyanoethyl)-diisopropylphosphoramidite 200 mg (574 µmol) 2'-deoxy-5'-methoxy-5-(E)-bromovinyluridine are dissolved in 5 ml dichloromethane and 200 µl (1.15 mmol) diisopropylethylamine are added. The reaction mixture is cooled to 0° C. and then 192 µl (861 µmol) 2-cyanoethyl-diisopropylchlorophosphoramidite are added. After 3 h at 0° C., the solvent is removed on the rotary evaporator, the residue is absorbed in 50 ml NaHCO$_3$ solution and extracted three times with 50 ml acetic ester. The combined organic phase is washed with 50 ml saturated NaCl solution, dried over Na$_2$SO$_4$, filtered and the solvent is removed on the rotary evaporator. Purification by column chromatography (chloroform/methanol 9/1, cyclohexane/acetic ester 1/1) yields 130 mg (237 µmol, 41%) [5-(E)-bromovinyl-5'-methoxy-2'-deoxyuridin]-3'-yl-(2-cyanoethyl)diisopropylphosphoramidite as white solid.

$^1$H-NMR (300 MHz, CDCl$_3$): 1.19 (d, 12H); 2.17-2.24 (m, 1H); 2.41-2.58 (m, 1H); 2.64 (t, 2H); 3.46-3.47 (2×s, 3H); 3.55-3.91 (m, 6H); 4.16-4.23 (m, 1H); 4.57-4.61 (m, 1H); 6.30-6.36 (m, 1H); 6.63 (d, 1H); 7.33 (d, 1H); 7.92-7.94 (2×s, 1H); 8.23 (bs, 1H) ppm.

The substance comprises a diastereomer mixture (ratio approx. 1:1).

$^{31}$P-NMR (122 MHz, CDCl$_3$): 149.45; 149.51 ppm.

2.4.2. [5-(E)-bromovinyl-3'-methoxy-2'-deoxyuridin]-5'-yl-(2-cyanoethyl)-diisopropylphosphoramidite 200 mg (574 µmol) 2'-deoxy-3'-methoxy-5-(E)-bromovinyluridine are dissolved in 5 ml dichloromethane and 200 µl (1.15 mmol) diisopropylethylamine are added. The reaction mixture is cooled to 0° C. and then 192 µl (861 µmol) 2-cyanoethyl-diisopropylchlorophosphoramidite are added. After 2 h at 0° C., the solvent is removed on the rotary evaporator, the residue is absorbed in 50 ml NaHCO$_3$ solution and extracted three times with 50 ml acetic ester. The combined organic phase is washed with 50 ml saturated NaCl solution, dried over Na$_2$SO$_4$, filtered and the solvent is removed on the rotary evaporator. Purification by column chromatography (chloroform/methanol 9/1, dichloromethane/acetic ester 1/1) yields 120 mg (219 µmol, 38%) [5-(E)-bromovinyl-3'-methoxy-2'-deoxyuridin]-5'-yl-(2-cyanoethyl)diisopropylphosphoramidite as white solid.

$^1$H-NMR (300 MHz, CDCl$_3$): 1.17-1.26 (m, 12H); 1.96-2.17 (m, 1H); 2.45-2.57 (m, 1H); 2.65-2.74 (m, 2H); 3.35-3.37 (2×s, 3H); 3.55-3.65 (m, 2H); 3.81-4.09 (m, 5H); 4.17-4.25 (2×m, 1H); 6.20-6.34 (2×m, 1H); 6.74-6.83 (2×d, 1H); 7.40-7.42 (2×d, 1H); 7.85, 8.10 (2×s, 1H); 8.03 (bs, 1H) ppm.

The substance comprises a diastereomer mixture (ratio approx. 1:1).

$^{31}$P-NMR (122 MHz, CDCl$_3$): 150.02; 150.48 ppm.

3. 3',5'-dihalogen derivatives of BVDU

3.1. 3',5'-difluoro-2',3',5'-trideoxy-5-(E)-bromovinyluridine

3.1.1. 5'-O-trityl-2,3'-anhydro-2'-deoxy-5-ethyl-uridine 17.84 g (35.78 mmol) 5'-O-trityl-2'-deoxy-5-ethyl-uridine and 14.08 g (53.67 mmol) triphenylphosphine are dissolved in 170 ml THF. There is added to this solution in drops a solution of 10.85 g (53.67 mmol) diisopropylazodicarbonic ester in 120 ml THF within 40 min. After 1 h agitation at room temperature, the conversion is complete (DC-control with chloroform/methanol 10:1). After mixing, there is obtained after purification by column chromatography (chloroform/methanol 10:1) 13.00 g (75.6%) of a colourless foam.

3.1.2. 1-(5'-O-trityl-2'-deoxy-β-D-threo-pentofuranosyl)-5-ethyl)-2,4-(1H, 3H)-pyrimidinedione 14.24 g (29.63 mmol) 5'-O-trityl-2,3'-anhydro-2'-deoxy-5-ethyl-uridine are heated in a mixture of 500 ml ethanol and 140 ml water with 3.03 g (75.85 mmol) sodium hydroxide for 90 min until boiling. Thereafter the reaction is terminated (DC-control with chloroform/methanol 10:1). The solution is mixed, treated with phosphate buffer and acetic ester and the phases are separated. The aqueous phase is extracted several times with acetic ester. The combined acetic ester phases are dried with magnesium sulphate. After filtration and centrifugation of the solvent, the obtained product is dried and 13.25 g (90.4%) of a colourless solid is obtained.

3.1.3. 5'-O-trityl-3'-fluoro-2',3'-dideoxy-5-ethyl-uridine 7.73 g (15.51 mmol) 1-(5'-O-trityl-2'-deoxy-β-D-threo-pentofuranosyl)-5-ethyl)-2,4-(1H, 3H)-pyrimidinedione are dissolved in 130 ml dichloromethane and, at 0° C., a solution of 5.0 g (31.02 mmol) diethylaminosulphurtrifluoride (DAST) is added in drops within 30 min. After 1 h agitation at 0° C., the conversion is complete (DC-control with dichloromethane/methanol 20:1). The batch is poured into ice-cold sodium hydrogen carbonate solution (5%), the phases are separated and the aqueous phase is extracted another twice with respectively 50 ml dichloromethane. The combined organic phases are dried with magnesium sulphate and, after filtration and centrifugation, purification by column chromatography is effected (dichloromethane/acetic ester 5:1). 5.17 g (66.6%) of a colourless foam is obtained.

3.1.4. 3'-fluoro-2',3'-dideoxy-5-ethyl-uridine 4.69 g (9.37 mmol) 5'-O-trityl-3'-fluoro-2',3'-dideoxy-5-ethyl-uridine are dissolved in 70 ml acetic acid and 18 ml water is added slowly. Heating takes place for 20 min to 90° C., thereafter the reaction is terminated (DC-control with chloroform/methanol 15:1). The batch is placed in the ice bath for 1 h, filtered and the residue is washed with 80% acetic acid. The filtrate is diluted with 400 ml water and extracted several times with acetic ester. The combined extracts are washed with saturated common salt solution and dried with magnesium sulphate. After filtration and centrifugation of the solvent, purification by column chromatography is effected (chloroform/methanol 15:1). 1.33 g (55.0%) of a colourless solid is obtained.

3.1.5. 5'-O-methylsulphonyl-3'-fluoro-2',3'-dideoxy-5-ethyl-uridine 1.33 g (5.15 mmol) 3'-fluoro-2',3'-dideoxy-5-ethyl-uridine are dissolved in 8 ml pyridine and there is added thereto in drops at 0° C. a solution of 1.78 g (15.5 mmol) methylsulphonylchloride in 2.5 ml THF within 20 min. Heating to room temperature takes place. The reaction is thereafter terminated (DC-control with chloroform/methanol 10:1). The batch is poured into ice water and agitated for 15 min. After acidification (pH approx. 1.5), it is extracted with acetic ester and the combined extracts are washed with phosphate buffer. After drying with magnesium sulphate, filtration and distilling-off of the solvent, 1.68 g (97.1%) of colourless foam is obtained.

3.1.6. 3',5'-difluoro-2',3',5'-trideoxy-5-ethyl-uridine 1.68 g (4.99 mmol) 5'-O-methylsulphonyl-3'-fluoro-2',3'-dideoxy-5-ethyl-uridine and 6.30 g (20.00 mmol) tetrabutylammoniumfluoride trishydrate are dissolved in 30 ml DMF and 20 g molecular sieve (3 Å) are added. After heating for 1.5 h to 40° C., the reaction is terminated (DC-control with chloroform/methanol 20:1). DMF is removed with xylene and the residue is dissolved in acetic ester. The acetic ester phase is washed with 1 M hydrochloric acid and phosphate buffer. The combined aqueous phases are neutralised and extracted with acetic ester. All the combined acetic ester phases are dried with magnesium sulphate and, after filtration and centrifugation of the solvent, are purified several times by column chromatography (chloroform/methanol 30:1); chloroform/acetic ester 3:1). 0.52 g (40.0%) of a colourless solid is obtained.

3.1.7. 3',5'-difluoro-2',3',5'-trideoxy-5-(E)-bromovinyluridine 520 mg (1.99 mmol) 3',5'-difluoro-2',3',5'-trideoxy-5-ethyl-uridine are dissolved in 15 ml chloroform and heated until boiling. 10 mg azo-bis-isobutyronitrile (AIBN) are added and a solution of 702 mg bromine in 2 ml chloroform is added in drops. During the addition in drops, irradiation with a 500 W lamp takes place. After 40 min, all the bromine is added and heating takes place for another 1 h at reflux. After cooling, argon is conducted through the solution and 304 mg triethylamine are added. After 1.5 h agitation at room temperature, this is shaken out with phosphate buffer and the aqueous phase is extracted again several times with acetic ester. The combined organic phases are dried with magnesium sulphate. After filtration and centrifugation of the solvent, multiple purification by column chromatography is effected (chloroform/methanol 25:1); chloroform/acetic ester 5:1) and subsequently recrystallisation from ethanol and methanol/water. 211 mg (31.3%) of a colourless solid with a melting point of 177-180° C. is obtained.

$^1$H-NMR (500 MHz, DMSO-d$_6$): 2.38 (m, 2H); 4.43 (m, 1H); 4.69 (m, 2H); 5.42 (m, 1H); 6.19 (m, 1H); 6.89 (d, 1H); 7.29 (d, 1H); 7.79 (s, 1H); 11.69 (s, 1H) ppm.

FIG. 7 shows the results of this compound according to the invention in combination with mitomycin C (MMC) in comparison with MMC alone and MMC in combination with BVDU.

3.2. 3'-fluoro-5'-chloro-2',3',5'-trideoxy-5-(E)-bromovinyluridine 190 mg (0.57 mmol) 3'-fluoro-2',3'-diideoxy-5-(E)-bromovinyluridine and 200 mg (0.76 mmol) triphenylphosphine are dissolved in 7 ml DMF and 440 mg (2.83 mmol) tetrachloromethane are added thereto. After 18 h agitation at room temperature, 100 mg (0.38 mmol) triphenylphosphine and 220 mg (1.42 mmol) tetrachloromethane are added. After 22 h the reaction is complete (DC-control with dichloromethane/acetic ester 4:1). DMF is removed by distillation with xylene and the residue is purified by column chromatography (dichloromethane/acetic ester 5:1). 60 ml (30%) of a crystalline solid with a melting point of 203° C. is obtained.

$^1$H-NMR (500 MHz, DMSO-d$_6$): 2.36 (m, 2H); 3.88 (m, 2H); 4.36 (m, 1H); 5.35 (d, 1H); 6.21 (m, 1H); 6.89 (d, 1H); 7.28 (d, 1H); 7.85 (s, 1H); 11.69 (s, 1H) ppm.

3.3. 3',5'-dichloro-2',3',5'-trideoxy-5-(E)-bromovinyluridine 0.70 g (2.0 mmol) 3'-chloro-2',3'-dideoxy-5-(E)-bromovinyluridine and 0.70 g (2.7 mmol) triphenylphosphine are dissolved in 10 ml DMF and 1.59 g (10.0 mmol) tetrachloromethane are added thereto. After 24 h agitation at room temperature, the reaction is complete (DC-control with dichloromethane/acetic ester 4:1). DMF is removed by distillation with xylene and the residue is purified by column chromatography (dichloromethane/acetic ester 4:1). After recrystallisation from n-hexane/acetic ester, 180 mg (24.3%) of a crystalline solid with a melting point of 184° C. is obtained.

$^1$H-NMR (500 MHz, DMSO-d$_6$): 2.59 (m, 1H); 2.76 (m, 1H); 3.94 (m, 2H); 4.27 (m, 1H); 4.71 (m, 1H); 6.26 (m, 1H); 6.90 (d, 1H); 7.29 (d, 1H); 7.81 (s, 1H); 11.67 (s, 1H) ppm.

3.4. 3'-azido-5'-fluoro-2',3,5"-trideoxy-5-(E)-bromovinyluridine

3.4.1. 2',3'-dideoxy-3'-azido-5'-O-(4-methylphenylsulphonyl)-5-(E)-bromovinyluridine 2.54 g (7.09 mmol) 2',3'-dideoxy-3'-azido-5-(E)-bromovinyluridine are dissolved at 0° C. in 20 ml pyridine and 2.56 g (13.42 mmol) 4-methyl-phenylsulphonylchloride are added thereto. Heating to room temperature takes place and agitation for 20 h. The reaction is thereafter complete (DC-control with chloroform/methanol 20:1). The batch is poured into 80 ml ice water and acidified with 6 M hydrochloric acid. Extraction takes place with acetic ester and the combined extracts are washed with saturated common salt solution, and dried with magnesium sulphate. After filtration and centrifugation of the solvent, the yield is 3.32 g (91.5%) of a colourless foam.

3.4.2. 3'-azido-5'-fluoro-2',3,5"-trideoxy 5-(E)-bromovinyluridine 3.32 g (6.48 mmol) 2',3'-dideoxy-3'-azido-5'-O-(4-methylphenylsulphonyl)-5-(E)-bromovinyluridine are dissolved in 50 ml DMF and 20 g molecular sieve (3 Å) and 8.17 tetrabutylammoniumfluoride trishydrate are added thereto. After 6 h heating to 40° C., the reaction is terminated (DC-control with cyclohexane/acetic ester 1:1). DMF is removed with xylene and the brown, oily residue is dissolved in acetic ester and washed with 100 ml 1 M hydrochloric acid, twice with respectively 50 ml phosphate buffer and with saturated common salt solution. The aqueous phases are combined, neutralised and extracted with acetic ester. All the combined organic phases are dried with magnesium sulphate. After filtration and centrifugation of the solvent, purification by column chromatography is effected (dichloromethane/acetic ester 5:1); cyclohexane/acetic ester 1.2:1). 0.72 g (19.2%) of a colourless solid with a melting point of 135° C. is obtained.

$^1$H-NMR (500 MHz, DMSO-d$_6$): 2.45 (m, 2H); 4.05 (m, 1H); 4.53 (m, 1H); 4.62 (m, 1H); 4.73 (m, 1H); 6.13 (m, 1H); 6.90 (d, 1H); 7.28 (d, 1H); 7.74 (s, 1H); 11.64 (s, 1H) ppm.

3.5. 3'-chloro-5'-bromo-2',3',5'-trideoxy-5-(E)-bromovinyluridine

3.5.1. 2',3'-dideoxy-3'-chloro-5'-O-methylsulphonyl-5-(E)-bromovinyluridine 1.0 g (2.84 mmol) 3'-chloro-2',3'-dideoxy-5-(E)-bromovinyluridine are dissolved in 5 ml THF/pyridine (1:1) and, at 0° C., 1.10 g (9.6 mmol) methylsulphonyl chloride, dissolved in 5 ml THF, are added in drops. Heating to room temperature takes place and agitation in total for 20 h. The conversion is thereafter complete (DC-control with dichloromethane/methanol 15:1). The batch is poured into ice water and left to agitate for 15 min. It is acidified with 2 M hydrochloric acid and the precipitating oil is extracted with acetic ester. The combined acetic ester phases are washed with phosphate buffer and dried with magnesium sulphate. After filtration and distilling-off of the solvent 1.22 g (quantitative yield) of a colourless foam is obtained.

3.5.2 3'-chloro-5'-bromo-2',3',5'-trideoxy-5-(E)-bromovinyluridine 510 mg (1.18 mmol) 3'-chloro-5'-O—(methylsulphonyl)-5-(E)-bromovinyluridine are heated with 515 mg (6 mmol) lithium bromide for h. Thereafter the reaction is terminated (DC-control with dichloromethane/methanol 25:1). DMF is removed by distillation with xylene and the residue is purified by column chromatography with chloroform/methanol 60:1, dichloromethane/methanol 40:1 and with cyclohexane/acetic ester 1.2:1. 240 mg (49.1%) of a colourless solid with a melting point of 149° C. is obtained.

$^1$H-NMR (500 MHz, DMSO-d$_6$): 2.52 (m, 1H); 2.76 (m, 1H); 3.73 (m, 1H); 3.81 (m, 1H); 4.27 (m, 1H); 4.68 (m, 1H); 6.27 (m, 1H); 6.90 (d, 1H); 7.29 (d, 1H); 7.82 (s, 1H); 11.67 (s, 1H) ppm.

3.5.3 5'-azido-3'-chloro-2',3',5'-trideoxy-5-(E)-bromovinyluridine 3.50 g (8.15 mmol) 3'-chloro-5'-O-(methylsulphonyl)-2',3'-dideoxy-5-(E)-bromovinyluridine are heated with 1.20 g (24.4 mmol, 3.0 eq.) lithium azide in 20 ml DMF for 1 h. The solvent is removed on the rotary evaporator. Purification by column chromatography (chloroform/methanol, 12/1) yields 2.12 g (5.63 mmol, 69%) 5'-azido-3'-chloro-2',3',5'-trideoxy-5-(E)-bromovinyluridine as white solid with a melting point of 58-60° C.

$^1$H-NMR (500 MHz, DMSO-d$_6$): 2.58 (m, 1H); 2.75 (m, 1H); 3.60 (m, 1H); 3.71 (m, 1H); 4.19 (m, 1H); 4.71 (m, 1H); 6.25 (dd, 1H); 6.93 (d, 1H); 7.30 (d, 1H); 7.86 (s, 1H); 11.69 (s, 1H) ppm.

3.5.4. 3'-azido-5'-chloro-2',3',5'-trideoxy-5-(E)-bromovinyluridine

3.5.4.1. 5'-chloro-3'-O-(methylsulphonyl)-2',5'-dideoxy-5-(E)-bromovinyluridine 1.00 g (2.84 mmol) 5'-chloro-2',5'-dideoxy-5-(E)-bromovinyluridine are placed in 10 ml pyridine at 0° C. 0.34 g (2.99 mmol) methanesulphonic acid chloride is added in drops to 5 ml THF and subsequently agitated for 4 h at room temperature. The reaction mixture is poured onto ice, adjusted with concentrated hydrochloric acid to pH=5 and extracted three times with acetic ester. The organic phase is washed with diluted hydrochloric acid and saturated NaCl solution, dried with Na$_2$SO$_4$, and the solvent is removed on the rotary evaporator. The result is 1.03 g (2.40 mmol, 84%) 5'-chloro-3'-O-(methylsulphonyl)-2',5'-dideoxy-5-(E)-bromovinyluridine as white solid.

3.5.4.2. 2,3'-anhydro-2'-deoxy-5'-chloro-5-(E)-bromovinyluridine 800 mg (1.86 mmol) 5'-chloro-3'-O-(methylsulphonyl)-2',5'-dideoxy-5-(E)-bromovinyluridine are placed in 10 ml THF. 340 mg (2.23 mmol) 1,8-diazabicyclo[5.4.0]undec-7-ene (DMU) are added and heated for 4 h at reflux. The solvent is removed on the rotary evaporator. Purification by column chromatography (chloroform/methanol, 9/1) yields 470 mg (1.41 mmol, 76%) 2,3'-anhydro-2'-deoxy-5'-chloro-5-(E)-bromovinyluridine as white solid.

3.5.4.3. 3'-azido-5'-chloro-2',3',5'-trideoxy-5-(E)-bromovinyluridine 470 mg (1.41 mmol) 2,3'-anhydro-5'-chloro-2'-deoxy-5-(E)-bromovinyluridine are placed in 10 ml DMF. 345 mg (7.05 mmol) LiN$_3$ are added and the reaction mixture is heated for 20 h. The solvent is removed on the rotary evaporator. The reaction mixture is absorbed in 50 ml acetic ester and the organic phase is washed with NaCl solution. The aqueous phase is extracted three times with acetic ester. The combined organic phase is washed with saturated NaCl solution, dried with Na$_2$SO$_4$ and the solvent is removed on the rotary evaporator. Purification by column chromatography (chloroform/methanol 9/1) yields 370 mg (982 µmol, 70%) 3'-azido-5'-chloro-2',3',5'-trideoxy-5-(E)-bromovinyluridine as white solid with a melting point of 124-125° C.

$^1$H-NMR (300 MHz, CDCl$_3$): 2.33-2.57 (m, 2H); 3.58-3.66 (m, 1H); 3.80-3.87 (m, 1H); 3.96-4.02 (m, 1H); 4.21-4.28 (m, 1H); 6.14 (t, 1H); 6.68 (d, 1H); 7.42 (d, 1H); 7.54, (s, 1H); 8.39 (bs, 1H).

3.6. 3',5'-dibromo-2',3',5'-trideoxy-5-(E)-bromovinyluridine 0.52 g (1.31 mmol) 2',3'-dideoxy-3'-bromo-5-(E)-bromovinyluridine are dissolved in 15 ml pyridine and 0.69 g (2.62 mmol) triphenylphosphine are added thereto. There is added to this solution in drops a solution of 0.79 mg (2.36 mmol) tetrabromomethane in 5 ml pyridine within 10 min. After 1 h the reaction is terminated (DC-control with chloroform/methanol 20:1). This is poured onto ice and acidified with 37% hydrochloric acid. Extraction with acetic ester (3×40 ml) follows, washing of the combined acetic ester phases with 1 M hydrochloric acid and with saturated common salt solution. After drying with magnesium sulphate and filtration, the crude substance is purified by column chromatography (dichloromethane/acetic ester 4:1) and reprecipitated from cyclohexane/acetic ester. After drying, 0.21 g (35.0%) of a colourless solid with a melting point of 153° C. is obtained.

$^1$H-NMR (500 MHz, DMSO-d$_6$): 2.68 (m, 1H); 2.81 (m, 1H); 3.74 (m, 1H); 3.82 (m, 1H); 4.38 (m, 1H); 4.65 (m, 1H); 6.27 (m, 1H); 6.91 (d, 1H); 7.29 (d, 1H); 7.82 (s, 1H); 11.66 (s, 1H) ppm.

FIG. 8 shows the results of this compound according to the invention in combination with mitomycin C (MMC) in comparison with MMC alone and MMC in combination with BVDU.

4. 2',3'-didehydro-2',3',5'-trideoxy-5'-bromo-5-(E)-bromovinyluridine

4.1 2',3'-didehydro-2',3'-dideoxy-5-(E)-bromovinyluridine

4.1.1. 1-(2'-deoxy-β-D-theo-pentofuranosyl)-5-(E)-(2-bromovinyl)-2,4(1H, 3H)-pyrimidinedione 20.07 g (47.87 mmol) 2,3'-anhydro-2'-deoxy-5'-O-benzoyl-5-(E)-bromovinyluridine are suspended in 400 ml ethanol and mixed with a solution of 4.78 g (120 mmol) sodium hydroxide in 95 ml water. This is heated for 2.5 h to boiling, thereafter the reaction is terminated (DC-control with dichloromethane/methanol 10:1). After neutralisation with hydrochloric acid, the solvent is distilled off until dry and the residue is extracted several times with acetone/acetic ester mixture (1:1). 13.5 g (84.6%) product are obtained.

4.1.2. 5'-O-benzoyl-1-(2'-deoxy-β-D-threo-pentofuranosyl)-5-(E)-(2-bromovinyl)-2,4(1H, 3H)-pyrimidinedione 5.0 g (15.00 mmol) 1-(2'-deoxy-β-D-threo-pentofuranosyl)-5-(E)-(2-bromovinyl)-2,4(1H, 3H)-pyrimidinedione are dissolved in 125 ml pyridine and cooled to 0° C. There is added thereto in drops at this temperature a solution of 2.53 g (18.0 mmol) benzoylchloride in 30 ml pyridine. After 60 min the addition in drops is terminated. Agitation takes place for another 60 min at 0° C. Thereafter the reaction is terminated (DC-control with dichloromethane/methanol 20:1). The batch is poured into 400 ml ice water, extracted with 4×100 ml acetic ester and the combined extracts are washed with 5% potassium hydrogen carbonate and saturated common salt solution. After drying with magnesium sulphate, filtering-off and distilling-off of the solvent, purification by column chromatography is effected (chloroform/methanol 20:1). 5.52 g (84.1%) of a colourless solid is obtained.

4.1.3. 3'-O-(methylsulphonyl)-5'-O-benzoyl-1-(2'-deoxy-β-D-threo-pentofuranosyl)-5-(E)-(2-bromovinyl)-2,4(1H, 3H)-pyrimidinedione 3.50 g (8.00 mmol) 5'-O-benzoyl-1-(2'-deoxy-β-D-threo-pentofuranosyl)-5-(E)-(2-bromovinyl)-2,4(1H, 3H)-pyrimidinedione are dissolved in 15 ml pyridine and mixed at 0° C. with 1.14 g (10.00 mmol) methanesulphonic acid chloride. After 18 h the reaction is terminated (DC-control with chloroform/methanol 12:1). Thereafter the batch is poured onto ice and left to stand for 20 min. This is acidified with 6 M hydrochloric acid and extracted with acetic ester (3×50 ml). The combined extracts are washed neutrally and dried with magnesium sulphate. After filtration and centrifugation of the solvent, 3.95 g (95.8%) of a yellowish foam is obtained.

4.1.4. 5'-O-benzoyl-2',3'-didehydro-2',3'-dideoxy-5-(E)-bromovinyluridine 3.38 (6.56 mmol) 3'-O-(methylsulphonyl)-5'-O-benzoyl-1-(2'-deoxy-β-D-threo-pentofuranosyl)-5-(E)-(2-bromovinyl)-2,4(1H, 3H)-pyrimidinedione are dissolved in 120 ml THF. 6.20 g (19.68 mmol) tetra-n-butylammoniumfluoride trishydrate and 25.0 g molecular sieve (3 Å) are added thereto and left to agitate for 20 h at room temperature. The reaction is thereafter complete (DC-control with dichloromethane/acetic ester 3:1). Filtration takes place over celite, washing thoroughly with acetic ester, concentration to 80 ml and washing with 3×80 ml saturated common salt solution. After drying with magnesium sulphate, filtration and purification by column chromatography, 2.20 g (80.0%) of a colourless solid is obtained.

4.1.5. 2',3'-didehydro-2',3'-dideoxy-5-(E)-bromovinyluridine 2.47 g (5.89 mmol) 5'-O-benzoyl-2',3'-didehydro-2',3'-dideoxy-5-(E)-bromovinyluridine are suspended in 70 ml THF and mixed with 8.8 ml (17.6 mmol) 2 M sodium hydroxide solution. After 5 h the conversion is complete (DC-control with dichloromethane/methanol 20:1). The batch is poured into 100 ml phosphate buffer solution (pH=7) and extracted with 5×50 ml acetic ester. After drying with magnesium sulphate and distilling-off of the solvent and after purification by column chromatography with chloroform/acetone 3:1, 1.73 g (93%) of a colourless solid with a melting point >250° C. (decomposition) is obtained.

$^1$H-NMR (500 MHz, DMSO-d$_6$): 3.63 (m, 2H); 4.81 (m, 1H); 5.09 (t, 1H); 5.92 (m, 1H); 6.42 (m, 1H); 6.75 (d, 1H); 6.82 (m, 1H); 7.17 (d, 1H); 8.04 (s, 1H); 11.59 (s, 1H) ppm.

4.2. 2',3'-didehydro-2',3',5'-trideoxy-5'-bromo-5-(E)-bromovinyluridine

4.2.1. 5'-O-(4-methylphenylsulphonyl)-2',3'-didehydro-2',3'-dideoxy-5-(E)-bromovinyluridine 0.55 g (1.75 mmol) 2',3'-didehydro-2',3'-dideoxy-5-(E)-bromovinyluridine are dissolved in 5 ml pyridine and mixed at 0° C. with 0.67 g (3.5 mmol) 4-methylphenylsulphonyl chloride. After 20 h the conversion is complete (DC-control with chloroform/methanol 20:1). This is poured on ice, left to agitate for 20 min and filtered. After thorough washing with water, drying takes place over calcium chloride. After purification by column chromatography with cyclohexane/acetone 2:1, 0.65 g (79.4%) of a colourless solid is obtained.

4.2.2. 2',3'-didehydro-2',3',5'-trideoxy-5'-bromo-5-(E)-bromovinyluridine 0.65 g (1.39 mmol) 5'-O-(4-methylphenylsulphonyl)-2',3'-didehydro-2',3'-dideoxy-5-(E)-bromovinyluridine and 0.87 g (10.00 mmol) lithium bromide are dissolved in 10 ml DMF and heated to 50° C. After 3.5 h, another 400 mg (4.6 mmol) lithium bromide is added and, after a further 60 min, the conversion is complete. The batch is poured into 40 ml water, the precipitated precipitate is filtered off and dried over calcium chloride. After purification by column chromatography with cyclohexane/acetone 2:1, 510 mg (97.3%) of a colourless solid with a melting point >150° C. is obtained.

$^1$H-NMR (500 MHz, DMSO-d$_6$): 3.75 (m, 2H); 5.03 (m, 1H); 6.06 (m, 1H); 6.47 (m, 1H); 6.82 (m, 1H); 6.96 (d, 1H); 7.29 (d, 1H); 7.65 (s, 1H); 11.68 (s, 1H) ppm.

5. 2'-fluorine derivatives of BVDU

5.1. 2'-fluoro-2'-deoxy-5-(E)-bromovinyluridine

5.1.1. 3-(2'-deoxy-2'-fluorouridine-5-yl)-acrylic acid 2.2 g (6.66 mmol) 3-(2'-deoxy-2'-fluorouridine-5-yl)-acrylic acid methylester are dissolved in 20 ml (40 mmol) 2 M sodium hydroxide solution. After 3 h, this is acidified with 12 M hydrochloric acid and cooled for one hour in the ice bath. After filtration, washing with ice water and drying in the desiccator, 1.31 g (62.1%) of a colourless solid is obtained.

5.1.2. 2'-fluoro-2'-deoxy-5-(E)-bromovinyluridine 1.31 g (3.97 mmol) 3-(2'-deoxy-2'-fluorouridine-5-yl)-acrylic acid are dissolved in 40 ml DMF and thereafter 1.58 g (16.04 mmol) potassium hydrogen carbonate are added. After 20 min agitation at room temperature, 0.86 g (4.81 mmol) N-bromosuccinimide, dissolved in 20 ml DMF, are added in drops within 3.0 min. After 4 h agitation at room temperature, filtration takes place, the residue is washed with DMF and DMF is distilled off with xylene. The residue is purified by column chromatography with chloroform/methanol 9:1. After digesting in diethylether and drying, 0.84 g (62.7%) of a colourless product with a melting point of 182° C. is obtained.
$^1$H-NMR (500 MHz, DMSO-$d_6$): 3.63 (m, 1H); 3.85 (m, 1H); 3.89 (m, 1H); 4.17 (m, 1H); 5.04 (dd, 1H); 5.35 (t, 1H); 5.61 (d, 1H); 5.88 (d, 1H); 6.75 (d, 1H); 7.21 (d, 1H); 8.19 (s, 1H); 11.65 (s, 1H) ppm.

5.2. 2'-fluoro-5'-bromo-2',5'-dideoxy-5-(E)-bromovinyluridine 0.25 g (0.71 mmol) 2'-fluoro-2'-deoxy-5-(E)-bromovinyluridine and 0.37 g (1.42 mmol) triphenylphosphine are dissolved in 10 ml pyridine. 0.42 g (1.28 mmol) tetrabromomethane are dissolved in 5 ml pyridine and added in drops within 5 min. After 1 h, the reaction is terminated. (DC-control with chloroform/methanol 10:1). After removal of the pyridine with toluene, purification by column chromatography with chloroform/methanol 30:1 is effected. 0.23 g (78%) of a colourless solid with a melting point of 223° C. is obtained.
$^1$H-NMR (500 MHz, DMSO-$d_6$): 3.78 (m, 1H); 3.85 (m, 1H); 4.0 (m, 1H); 4.13 (m, 1H); 5.19 (dd, 1H); 5.87 (d, 1H); 5.91 (dd, 1H); 6.89 (d, 1H); 7.29 (d, 1H); 7.77 (s, 1H); 11.72 (s, 1H) ppm.

5.3. 5-(E)-2-bromovinyl)-1-(2'-deoxy-2'-fluoro-β-D-arabinofuranosyl)uracil

5.3.1 5-iodo-1-(2'-deoxy-2'-fluoro-3',5'-di-O-benzoyl-β-D-arabinofuranosyl)uracil 7.08 g (29.75 mmol) 5-iodouracil are suspended in 105 ml 1,2-dichloroethane. 13.32 g (65.47 mmol) N,O-bis-trimethylsilylacetamide (BSA) are added thereto and agitated for 5 h at room temperature. A clear, colourless solution is produced. 11.40 g (26.9 mmol) 3,5-di-O-benzoyl-2-deoxy-2-fluoro-α-D-arabinosyl-bromide are added thereto. This is heated for 22 h at reflux. The conversion is thereafter complete (DC-control with chloroform/methanol 100:1). The batch is diluted with 450 ml acetic ester and treated with 400 ml phosphate buffer (pH=7). The organic phase is separated and the aqueous one extracted with 3×150 ml acetic ester. After drying the combined organic phases with magnesium sulphate, filtering-off of the drying agent and distilling-off of the solvent, recrystallisation takes place from isopropyl alcohol. 8.47 g (54.3%) of a colourless product is obtained.

5.3.2. 5-iodo-1-(2'-deoxy-2'-fluoro-β-D-arabinofuranosyl)uracil 8.14 (14.03 mmol) 5-iodo-1-(2'-deoxy-2'-fluoro-3',5'-di-O-benzoyl-β-D-arabinofuranosyl)uracil are dissolved in 250 ml THF and mixed with 50 ml (100 mmol) 2 M sodium hydroxide solution. After 4 h the reaction is terminated. The solution is neutralised and extracted several times with acetic ester. The combined extracts are dried with magnesium sulphate. After filtration and centrifugation of the solvent, purification by column chromatography is effected (chloroform/methanol 10:1). 4.80 g (91.8%) of a colourless solid is obtained.

5.3.3. 34(2'-deoxy-2'-fluoro-β-D-arabinofuranosyl) uracil-5-yl)-acrylic acid methyl ester 0.75 g (2.84 mmol) triphenylphosphine, 0.34 g (1.52 mmol) palladium (II) acetate and 6.17 g (61 mmol) triethylamine are heated in 160 ml 1,4-dioxane to 80° C. A deep dark red colouration takes place. This is heated for 10 min at this temperature and then 6.54 g (76 mmol) acrylic acid methyl ester, 4.80 g (12.9 mmol) 5-iodo-1-(2'-deoxy-2'-fluoro-β-D-arabinofuranosyl)uracil and 40 ml 1,4-dioxane are then added. After heating for 1 h at reflux, the conversion is complete (DC-control with chloroform/methanol 9:1). After cooling, this is filtered off via celite from the undissolved part and washed thoroughly again with THF until the filtrate runs colourless. The filtrate is centrifuged off and the oily residue is purified by column chromatography with chloroform/methanol 10:1). 2.72 g (54.4%) of a colourless solid is obtained.

5.3.4. 3-((2'-deoxy-2'-fluoro-β-D-arabinofuranosyl) uracil-5-yl)-acrylic acid 2.72 g (8.25 mmol) 3-((2'deoxy-2'-fluoro-β-D-arabinofuranosyl)uracil-5-yl)acrylic acid methyl ester are dissolved in 40 ml (80 mmol) 2 M sodium hydroxide solution. After 4 h the reaction is terminated (DC-control with chloroform/methanol 8:1). This is acidified with 12 M hydrochloric acid and left to stand for 1 h in the ice bath. The precipitate is suctioned off, washed with ice water and dried in the desiccator. 2.61 g (100%) of a colourless product is obtained.

5.3.5. 5-(E)-(2-bromovinyl)-1-(2'-deoxy-2'-fluoro-β-D-arabinofuranosyl)uracil 2.61 g (7.9 mmol) 3-((2'-deoxy-2'-fluoro-β-D-arabinofuranosyl)uracil-5-yl)-acrylic acid are dissolved in 60 ml DMF and mixed with 3.2 g (32 mmol) potassium hydrogen carbonate. Agitation takes place at room temperature for 30 min and thereafter a solution of 1.78 g (10 mmol) in 30 ml DMF is added in drops within 50 min. After a further 3.5 h agitation at room temperature, the undissolved part is filtered off, the residue is washed thoroughly with acetone/methanol 1:1 and centrifuged. DMF is removed by distillation with xylene. After purification by column chromatography with chloroform/methanol 9:1 and dichloromethane/acetic ester 1:2, 1.51 g (54.5%) of a colourless solid with a melting point of 202° C. is obtained.
$^1$H-NMR (500 MHz, DMSO-$d_6$): 3.62 (m, 1H); 3.65 (m, 1H); 3.81 (m, 1H); 4.25 (dq, 1H); 5.06 (dt, 1H); 5.14 (t, 1H); 5.89 (d, 1H); 6.11 (dd, 1H); 6.88 (d, 1H); 7.27 (d, 1H); 7.99 (s, 1H); 11.75 (s, 1H).

5.4. 5-(E)-(2-bromovinyl)-1-(2',5'-dideoxy-2'-fluoro-5'bromo-βD-arabinofuranosyl)-uracil 0.60 g (1.71 mmol) 5-(E)-(2-bromovinyl)-1-(2'-deoxy-2'-fluoro-β-D-arabinofuranosyl)-uracil and 950 mg (3.62 mmol) triphenylphosphine are dissolved in 10 ml pyridine.

Thereafter, a solution of 1.08 g (3.25 mmol) tetrabromomethane in 10 ml pyridine are added within 10 min. After 1.5 h the conversion is complete (DC-control with chloroform/methanol 10:1). Pyridine is distilled off with toluene and the residue is purified by column chromatography with chloroform/methanol 30:1). 0.63 g (89.0%) of a colourless product with a melting point of 237° C. is obtained.

$^1$H-NMR (300 MHz, DMSO-d$_6$): 3.79 (m, 2H); 4.07 (m, 1H); 4.26 (dq, 1H); 5.09 (ddd, 1H); 6.16 (d, 1H); 6.23 (dd, 1H); 6.98 (d, 1H); 7.30 (d, 1H); 7.74 (d, 1H); 11.80 (s, 1H) ppm.

6. 2',2'-difluorine derivatives of BVDU

6.1. 1-(2'-deoxy-2',2'-difluoro-α-D-erythro-pentofuranos-1'-yl)-5-(E)-bromovinyluracil and 1-(2'-deoxy-2',2'-difluoro-β-D-erythro-pentofuranos-1'-yl)-5-(E)-bromovinyluracil

6.1.1. 1-(3',5'-di-O-benzoyl-2',2'-difluoro-α-D-pentofuranos-1'-yl)-5-(E)-bromovinyluracil and 1-(3',5'-di-O-benzoyl-2',2'-difluoro-β-D-pentofuranos-1'-yl)-5-(E)-bromovinyluracil 1.89 g (8.70 mmol) 5-(E)-bromovinyluracil are suspended in 40 ml 1,2-dichloroethane and 4.28 g (19.23 mmol) trimethylsilyltrifluoromethanesulphonate and 2.14 g (177 mmol) 2,4,6-collidine are added. After 1 h, a clear solution is obtained. 3.98 g (8.7 mmol) 2-deoxy-2,2-difluoro-D-ribofuranose-3,5-dibenzoate-1-methanesulphonate (α/β mixture) are dissolved in 25 ml 1,2-dichloroethane and added in drops within 20 min. Thereafter, a solution of 1.94 g (8.7 mmol) trimethylsilyltrifluoromethanesulphonate is added in drops in 15 ml 1,2-dichloroethane within 10 min and heated for 18 h at reflux. DC-control (chloroform/methanol 10:1 and 100:1) results in the conversion being complete. The solvent is distilled off and the oily residue is dissolved in 80 ml acetic ester. After washing with 2×80 ml 1 M hydrochloric acid, 2×80 ml saturated common salt solution and with 1×80 ml phosphate buffer, drying is effected with magnesium sulphate. After filtration and centrifugation of the solvent, the crude substance is purified by column chromatography with chloroform/methanol 125:1. 3.1 g (61.7%) of a colourless foam is obtained (α/β=1.2).

The separation of the α and β anomers is effected by repeated column chromatography with cyclohexane/acetic ester 3:1.

1.49 g α-anomer and 1.15 g β-anomer are obtained.

6.1.2. 1-(2'-deoxy-2',2'-difluoro-α-D-erythro-pentofuranos-1'-yl)-5-(E)-bromovinyluracil 1.49 g (2.58 mmol) 1-(3',5'-di-O-benzoyl-2',2'-difluoro-α-D-pentofuranos-1'-yl)-5-(E)-bromovinyluracil are dissolved in 55 ml THF and 13 ml (26 mmol) 2 M sodium hydroxide solution are added. After 3 h this is neutralised and extracted with acetic ester. After drying with magnesium sulphate, filtration and centrifugation of the solvent, purification by column chromatography is effected with chloroform/methanol 20:1 and dichloromethane/methanol 20:1. After drying, 0.82 g (86%) of a colourless solid with a melting point of 192° C. is obtained.

$^1$H-NMR (500 MHz, DMSO-d$_6$): 3.56 (m, 1H); 3.65 (m, 1H); 4.35 (m, 2H); 5.08 (s, 1H); 6.22 (m, 1H); 6.34 (d, 1H); 7.02 (d, 1H); 7.32 (d, 1H); 7.85 (s, 1H); 11.81 (s, 1H) ppm.

6.1.3. 1-(2'-deoxy-2',2'-difluoro-β-D-erythro-pentofuranos-1'-yl)-5-(E)-bromovinyluracil 1.15 g (1.99 mmol) 1-(3',5'-di-O-benzoyl-2',2'-difluoro-β-D-pentofuranos-1'-yl)-5-(E)-bromovinyluracil are dissolved in 55 ml THF and mixed with 10 ml (20 mmol) sodium hydroxide solution. The processing and purification by column chromatography is effected analogously, as described above for the α-anomer. 740 mg (100%) of a colourless solid with a melting point of 189° C. is obtained.

$^1$H-NMR (500 MHz, DMSO-d$_6$): 3.64 (m, 1H); 3.81 (m, 1H); 3.87 (m, 1H); 4.22 (m, 1H); 5.36 (t, 1H); 6.06 (t, 1H); 6.33 (d, 1H); 6.83 (d, 1H); 7.27 (d, 1H); 8.05 (s, 1H); 11.86 (s, 1H) ppm.

6.1.4. 1-(5'-chloro-2',5'-dideoxy-2',2'-difluoro-α-D-erythro-pentofuranos-1'-yl)-5-(E)-bromovinyluracil 350 mg (0.95 mmol) 1-(2'-deoxy-2',2'-difluoro-α-D-erythro-pentofuranos-1'-yl)-5-(E)-bromovinyluracil are dissolved in 8 ml DMF. 337 mg (1.29 mmol) triphenylphosphine are added and thereafter 729 mg (4.74 mmol) tetrachloromethane. After 20 h agitation at room temperature, the conversion is complete (DC-control with chloroform/methanol 15:1). After the addition of 2 ml methanol, DMF is removed with xylene and the brown residue is purified several times by column chromatography with chloroform/methanol 30:1. 240 mg (65.2%) of a colourless product with a melting point of 208° C. is obtained.

$^1$H-NMR (500 MHz, DMSO-d$_6$): 3.87 (m, 1H); 3.94 (m, 1H); 4.42 (m, 1H); 4.61 (m, 1H); 6.31 (m, 1H); 6.61 (s (br.), 1H); 6.99 (d, 1H); 7.33 (d, 1H); 7.89 (d, 1H); 11.82 (s, (br.), 1H) ppm.

6.1.5. 1-(5'-chloro-2',5'-dideoxy-2',2'-difluoro-β-D-erythro-pentofuranos-1'-yl)-5-(E)-bromovinyluracil 520 mg (1.41 mmol) 1-(2'-deoxy-2',2'-difluoro-β-D-erythro-pentofuranos-1'-yl)-5-(E)-bromovinyluracil, 500 mg (1.90 mmol) triphenylphosphine are converted and processed with 1083 mg (7.04 mmol) tetrachloromethane analogously, as described above. After multiple purification by column chromatography with chloroform/methanol 20:1, 460 mg (84.1%) of a colourless product with a melting point of 191° C. is obtained.

$^1$H-NMR (500 MHz, DMSO-d$_6$): 3.99 (m, 2H); 4.05 (m, 1H); 4.25 (m, 1H); 6.17 (t, 1H); 6.57 (d, 1H); 6.93 (d, 1H); 7.33 (d, 1H); 7.76 (s, 1H); 11.90 (s, 1H) ppm.

7. 1-(β-D-arabinofuranosyl)-5-(E)-bromovinyluracil

7.1 3-(1-(2,3,6-tri-O-acetyl-β-D-arabinofuranosyl)-uracil-5-yl)-acrylic acid methyl ester 0.84 g (3.2 mmol) palladium(II) acetate, 0.89 g (3.38 mmol) triphenylphosphine and 7.35 g (73.56 mmol) triethylamine are heated in 135 ml dioxane to 70° C. A deep dark red coloured solution is produced. This is heated for 10 min at this temperature, firstly 22.74 g (264 mmol) acrylic acid methyl ester and thereafter 9.0 g (18.13 mmol) 1-(2,3,6-tri-O-acetyl-β-D-arabinofuranosyl)-5-iodouracil and also 90 ml dioxane are added. After 2.5 h heating at reflux, the reaction is terminated (DC-control with dichloromethane/acetic ester 5:2). After cooling, this is diluted with acetic ester, filtered off from the undissolved part and the filtrate is evaporated. The residue is purified by column chromatography (dichloromethane/acetic ester 5:2). 6.3 g (76.5%) of a colourless foam is obtained.

7.2. 3-(1-(β-D-arabinofuranosyl)uracil-5-yl)-acrylic acid 6.3 g (13.86 mmol) 3-(1-(2,3,6-tri-O-acetyl-β-D-arabinofuranosyl)-uracil-5-yl)-acrylic acid methyl ester are dissolved in 140 ml THF and mixed with 140 ml (280 mmol) 2 M sodium hydroxide solution. After 5 h, the solution is concentrated and acidified with 12 M hydrochloric acid. The batch is kept for 1 h in the ice bath and the precipitate is suctioned off and washed with ice water. After drying in the desiccator, 3.45 g (79.4%) of a colourless solid is obtained.

7.2. 3-(1-(β-D-arabinofuranosyl)-uracil-5-yl)-acrylic acid 6.3 g (13.86 mmol) 3-(1-(2,3,6-tri-O-acetyl-β-D-arabinofuranosyl)-uracil-5-yl)-acrylic acid methyl ester are dissolved in 140 ml THF and mixed with 140 ml (280 mmol) 2 M sodium hydroxide solution. After 5 h, the solution is concentrated and acidified with 12 M hydrochloric acid. The batch is kept for 1 h in the ice bath and the precipitate is suctioned off and washed with iced water. After drying in the desiccator, 3.45 g (7.94%) of a colourless solid is obtained.

7.3. 1-(β-D-arabinofuranosyl)-5-(E)-bromovinyluracil 3.46 g (11.01 mmol) 3-(1-(β-D-arabinofuranosyl)-uracil-5-yl)-acrylic acid are dissolved in 100 ml DMF and 5.51 g (55.05 mmol) potassium hydrogen carbonate are added. After 30 min agitation at RT, a solution of 2.37 g (13.4 mmol) N-bromosuccinimide is added in drops within 1 h. After 4.5 h agitation at room temperature, DMF is removed with the xylene and the residue is purified by column chromatography with dichloromethane/methanol 10:1. After recrystallisation from methanol, a colourless, crystalline product (0.84 g, 21.8%) is obtained.

$^1$H-NMR (500 MHz, DMSO-$d_6$): 3.63 (m, 2H); 3.74 (m, 1H); 3.91 (m, 1H); 4.03 (m, 1H); 5.11 (t, 1H); 5.45 (d, 1H); 5.55 (d, 1H); 5.97 (d, 1H); 6.87 (d, 1H); 7.24 (d, 1H); 7.89 (s, 1H); (11.57 (s, 1H) ppm.

8. 5'-deoxy-BVDU and 3',5'-dideoxy-3'-halogen-BVDU

8.1. 5'-deoxy-BVDU

8.1.1. 2',5'-dideoxy-5'-iodo-5-ethyl-uridine 8.0 g (31.22 mmol) 2'-deoxy-5-ethyl-uridine and 10.66 g (40.64 mmol) triphenylphosphine are dissolved in 50 ml pyridine. 10.32 g (40.64 mmol) iodine is added thereto in several portions. After 4 h the conversion is complete (DC-control with dichloromethane/methanol 15:1). Pyridine is distilled off in a vacuum and the residue is dissolved in acetic ester and washed with 1 M hydrochloric acid. The aqueous phase is extracted several times with acetic ester and the combined acetic ester phases are washed with phosphate buffer. After drying with magnesium sulphate, filtering-off and washing with acetic ester, the solvent is distilled off until it is dry and the residue is washed with toluene and dichloromethane. 7.5 g (65.6%) of a faintly yellowish product is obtained.

8.1.2. 2',5'-dideoxy-5-ethyl-uridine 4.68 g (12.78 mmol) 2',5'-dideoxy-5'-iodo-5-ethyl-uridine and 1.08 g (27.0 mmol) sodium hydroxide are dissolved in 280 ml ethanol, mixed with 780 g hydrogenating catalyst (palladium on activated carbon, 10% Pd) and hydrogenated for 12 h. The reaction is terminated thereafter (DC-control with dichloromethane/methanol 10:1). After filtering-off of the hydrogenating catalyst, evaporation until dry takes place and the residue is mixed with phosphate buffer. The precipitate is suctioned off, washed with ice water and dried over potassium hydroxide. The filtrate is extracted several times with acetic ester. The combined extracts are dried with magnesium sulphate. After filtering-off of the drying agent, washing with acetic ester, evaporation until dry takes place. In total 2.97 g (96.7%) of a colourless solid is obtained.

8.1.3. 2',5'-dideoxy-3'-O-benzoyl-5-ethyl-uridine 3.28 g (13.65 mmol) 2',5'-dideoxy-5-ethyl-uridine are dissolved in 35 ml pyridine and mixed at 0° C. with 2.14 g (15.21 mmol) benzoylchloride. After 30 min, the cold bath is removed and agitation takes place for another 1 h at room temperature. Thereafter the conversion is complete. Pyridine is removed with toluene and the residue is dissolved in chloroform. Washing takes place with 0.1 M hydrochloric acid and washing takes place neutrally with phosphate buffer. After drying of the organic phase with magnesium sulphate, filtering-off of the drying agent and centrifugation of the solvent, purification by column chromatography is effected with dichloromethane/acetone 10:1. 3.82 g (81.3%) of a white foam is obtained.

8.1.4. 2',5'-dideoxy-3'-O-benzoyl-5-(E)-bromovinyluridine 2.79 g (8.1 mmol) 2',5'-dideoxy-3'-O-benzoyl-5-ethyl-uridine and 50 mg AIBN are dissolved in 45 ml chloroform and heated until boiling. A solution of 2.88 g (18 mmol) bromine in 15 ml chloroform is added thereto in drops within 1.5 h. Heating takes place until boiling for another 0.5 h and argon is conducted through the solution for 1 h after cooling to room temperature. 2.88 g (19.8 mmol) triethylamine is added thereafter to the solution and agitated for 1 h at room temperature. Chloroform is distilled off and the residue is absorbed in acetic ester and washed with saturated common salt solution. After drying the organic phase with magnesium sulphate, filtering-off of the drying agent and centrifugation of the solvent, purification by column chromatography is effected with dichloromethane/acetone 20:1. 1.97 g (57.8%) of a white foam is obtained.

8.1.5. 2',5'-dideoxy-5-(E)-bromovinyluridine 2.48 g (5.88 mmol) 2',5'-dideoxy-3'-O-benzoyl-5-(E)-bromovinyluridine are dissolved in 25 ml THF and mixed with 15 ml (30 mmol) 2 M sodium hydroxide solution. After 3 h agitation at room temperature the conversion is terminated (DC-control with dichloromethane/acetone 10:1). Mixing takes place with 80 ml phosphate buffer and extraction several times with acetic ester. After drying of the organic phase with magnesium sulphate, filtering-off of the drying agent and centrifugation of the solvent, purification by column chromatography is effected with chloroform/methanol 20:1. 1.65 g (88.7%) of a colourless solid with a melting point of 174° C. (decomposition) is obtained.

¹H-NMR (300 MHz, DMSO-d₆): 2.11 (d, 3H); 2.15 (m, 2H); 3.81 (m, 1H); 3.98 (m, 1H); 5.26 (d, 1H); 6.09 (m, 1H); 6.99 (d, 1H); 7.31 (d, 1H); 7.76 (s, 1H); (11.58 (s, 1H) ppm.

8.2. 3'-chloro-2',3',5'-trideoxy-5-(E)-bromovinyluridine

8.2.1. 2,3'-anhydro-1-(2',5'-dideoxy-β-D-threo-pentofuranosyl)-5-(E)-bromovinyluracil 1.47 g (4.64 mmol) 2',5'-dideoxy-5-(E)-bromovinyluridine and 1.83 g (6.96 mmol) triphenylphosphine are dissolved in 40 ml THF and there is added to this solution in drops a solution of 1.44 g (7.16 mmol) diisopropylazodicarboxylate in 10 ml THF within 20 min. After 4 h the reaction is terminated (DC-control with dichloromethane/methanol 15:1). THF is distilled off and the residue is absorbed in toluene. It is filtered off and the residue is washed several times with toluene. A colourless solid (1.19 g, 85.7%) is obtained.

8.2.2. 3'-chloro-2',3',5'-trideoxy-5-(E)-bromovinyluridine 0.59 g (1.97 mmol) 2,3'-anhydro-1-(2',5'-dideoxy-β-D-threo-pentofuranosyl)-5-(E)-bromovinyluracil and 0.5 g (4.33 mmol) pyridinehydrochloride are suspended in 5 ml DMF and heated to 90° C. After 1 h the reaction is terminated (DC-control with dichloromethane/methanol 15:1). DMF is distilled off with xylene and the residue is treated with acetic ester and saturated common salt solution. The aqueous phase is extracted several times with acetic ester and the combined acetic ester phases dried with magnesium sulphate. After filtering-off of the drying agent, washing with acetic ester and distilling-off of the solvent, purification by column chromatography is effected with chloroform/methanol 100:1 and chloroform/acetic ester 5:1. 0.25 g (37.8%) of a colourless solid with a melting point of 134° C. is obtained.

¹H-NMR (300 MHz, DMSO-d₆): 1.34 (d, 3H); 2.58 (m, 1H); 2.66 (m, 1H); 4.03 (m, 1H); 4.44 (m, 1H); 6.17 (dd, 1H); 6.97 (d, 1H); 7.31 (d, 1H); 7.77 (s, 1H); (11.62 (s, 1H) ppm.

8.3. 3'-bromo-2',3',5-trideoxy-5-(E)-bromovinyluridine 0.59 g (1.97 mmol) 2,3'-anhydro-1-(2',5'-dideoxy-β-D-threo-pentofuranosyl)-5-(E)-bromovinyluracil and 0.96 pyridinehydrobromide (6.0 mmol) are converted in DMF and processed as described above under 8.2.2. The product is purified several times by column chromatography with chloroform/methanol 70:1 and 0.22 g (29.4%) of a colourless solid with a melting point of 128° C. is obtained.

¹H-NMR (300 MHz, DMSO-d₆): 1.35 (d, 3H); 2.65 (m, 2H); 4.12 (m, 1H); 4.41 (m, 1H); 6.15 (dd, 1H); 6.98 (d, 1H); 7.30 (d, 1H); 7.76 (s, 1H); 11.62 (s, 1H) ppm.

9. 1-[2',5-dideoxy-β-D-glycero-pent-4-enofuranosyl]-5-(E)-bromovinyluracil

9.1 2',5'-dideoxy-5'-iodo-5-(E)-bromovinyluridine 3.0 g (9.0 mmol) 2'-deoxy-5-(E)-bromovinyluridine and 3.07 g (11.7 mmol) triphenylphosphine are dissolved in 30 ml pyridine and cooled to 10° C. 2.97 g (11.7 mmol) iodine is added thereto in several portions. Heating to room temperature takes place. After 6 h the conversion is complete (DC-control with dichloromethane/methanol 15:1). Pyridine is distilled off and the residue is absorbed in acetic ester/2-butanone (2:1) and washed with sodium disulphate solution. The aqueous phase is extracted several times with acetic ester and the combined organic phases are dried with magnesium sulphate. After filtering-off of the drying agent and distilling-off of the solvent, the residue is treated with toluene/dichloromethane 1:1 and the obtained solid is dried. 3.77 g (94.5%) of a colourless solid is obtained.

9.2. 2',5'-dideoxy-3'-O-acetyl-5'-iodo-5-(E)-bromovinyluridine 2.48 g (5.59 mmol) 2',5'-dideoxy-5'-iodo-5-(E)-bromovinyluridine are dissolved in 20 ml pyridine and mixed with 3.20 g (31.34 mmol) acetic anhydride. After 90 min the reaction is terminated (DC-control with dichloromethane/methanol 10:1). The batch is poured into phosphate buffer solution and extracted several times with acetic ester after 15 min. The combined extracts are dried with magnesium sulphate and, after normal processing, purified by column chromatography with chloroform/acetone 10:1. 2.14 g (78.7%) of a colourless solid is obtained.

9.3. 1-[3'-O-acetyl-2',5'-dideoxy-β-D-glycero-pent-4-enofuranosyl]-5-(E)-bromovinyluracil 2.14 g (4.41 mmol) 2',5'-dideoxy-3'-O-acetyl-5'-iodo-5-(E)-bromovinyluridine are dissolved in 45 ml acetonitrile and mixed with 2.08 g (13.73 mmol) DBU (1,8-diazabicyclo [5.4.0]undec-7-ene. After 18 h agitation at room temperature the conversion is complete (DC-control with cyclohexane/acetic ester 1:1). This is poured into phosphate buffer and extracted several times with acetic ester. The combined extracts are dried with magnesium sulphate and purified by column chromatography, after normal processing, with cyclohexane/acetic ester 1:1 and chloroform/acetone 8:1. 1.24 g (77.3%) of a colourless solid with a melting point of 148° C. is obtained.

¹H-NMR (500 MHz, DMSO-d₆): 2.07 (s, 3H); 2.44 (m, 1H); 2.71 (m, 1H); 4.27 (dd, 1H); 4.47 (d, 1H); 5.78 (m, 1H); 6.37 (t, 1H); 6.88 (d, 1H); 7.29 (d, 1H); 7.90 (s, 1H), 11.70 (s, 1H) ppm.

9.4. 1-[2',5'-dideoxy-β-D-glycero-pent-4-enofuranosyl]-5-(E)-bromovinyluracil 0.86 g (2.41 mmol) 1-[3'-O-acetyl-2',5'-dideoxy-β-D-glycero-pent-4-enofuranosyl]-5-(E)-bromovinyluracil are dissolved in 10 ml methanol and mixed with 15 ml of a saturated solution of ammonia in methanol. After 7 h the conversion is terminated (DC-control with chloroform/methanol 15:1). The solvent is withdrawn and the residue is purified by column chromatography with chloroform/methanol 15:1 and dichloromethane/acetic ester 1:1. 210 mg (27.6%) of a colourless substance with a melting point of 128° C. (decomposition) is obtained.

¹H-NMR (500 MHz, DMSO-d₆): 2.21 (m, 1H); 2.48 (m, 1H); 4.16 (d, 1H); 4.31 (d, 1H); 4.72 (m, 1H); 5.56 (d, 1H); 6.39 (t, 1H); 6.93 (d, 1H); 7.29 (d, 1H); 7.80 (s, 1H); 11.66 (s, 1H) ppm.

10. 5'-cyano-2',5'-dideoxy-5-(E)-bromovinyluridine

10.1. 5'-cyano-2',5'-dideoxy-5-ethyl-uridine 2.54 g (6.93 mmol) 5'-iodo-2',5'-dideoxy-5-ethyl-uridine are dissolved in 50 ml DMSO and 0.52 g (10.61 mmol)

sodium cyanide are added thereto. After 18 h the conversion is complete (DC-control with acetic ester). The batch is poured into saturated common salt solution and extracted several times with acetic ester. The combined extracts are dried with magnesium sulphate and purified by column chromatography with acetic ester after normal processing. 0.96 g (52.1%) of a colourless substance is obtained.

10.2. 3'-O-acetyl-5'-cyano-2',5'-dideoxy-5-ethyl-uridine 0.96 g (3.62 mmol) 5'-cyano-2',5'-dideoxy-5-ethyl-uridine are dissolved in 15 ml pyridine and mixed with 1.77 g (17.35 mmol) acetic anhydride. After 1 h the conversion is complete (DC-control with acetic ester). The batch is poured into phosphate buffer and extracted several times with acetic ester. The combined extracts are dried with magnesium sulphate and purified by column chromatography with dichloromethane/acetic ester after normal processing. 0.82 g (73.7%) of a colourless substance is obtained.

10.3. 3'-O-acetyl-5'-cyano-2',5'-dideoxy-5-(E)-bromovinyluridine 0.82 g (2.67 mmol) 3'-O-acetyl-5'-cyano-2',5'-dideoxy-5-ethyl-uridine and 0.01 g AIBN (azo-bis-isobutyronitrile) are dissolved in 30 ml chloroform and heated until boiling. A solution of 0.94 g (5.87 mmol) bromine in 10 ml chloroform is added in drops thereto. After 65 min the addition in drops is terminated. Heating takes place for another 1 h at reflux, cooling to room temperature and 0.66 g (6.52 mmol) triethylamine are added. After 1 h, the solvent is distilled off and the residue is treated with acetic ester and phosphate buffer. The aqueous phase is extracted several times with acetic ester and the combined acetic ester phases are dried with magnesium sulphate. After normal processing, purification by column chromatography is effected with cyclohexane/acetic ester 2:3. 0.62 g (59.7%) of a colourless substance with a melting point of 96° C. is obtained.

$^1$H-NMR (300 MHz, DMSO-$d_6$): 2.07 (s, 3H); 2.39 (m, 1H); 2.53 (m, 1H); 3.08 (m, 2H); 4.21 (m, 1H); 5.16 (m, 1H); 6.17 (t, 1H); 6.88 (d, 1H); 7.28 (d, 1H); 7.88 (s, 1H); 11.68 (s, 1H) ppm.

10.4 5'-cyano-2',5'-dideoxy-5-(E)-bromovinyluridine 0.41 g (1.07 mmol) 3'-O-acetyl-5'-cyano-2',5'-dideoxy-5-(E)-bromovinyluridine are dissolved in 20 ml methanol and mixed with 10 ml of a saturated solution of hydrogen chloride in methanol. After 36 h the conversion is complete (DC-control with chloroform/methanol 15:1). After distilling-off of the solvent, purification by column chromatography is effected (chloroform/methanol 15:1). 0.35 g (95.9%) of a colourless substance with a melting point of 177° C. (decomposition) is obtained.

$^1$H-NMR (300 MHz, DMSO-$d_6$): 2.15 (m, 1H); 2.29 (m, 1H); 2.99 (m, 2H); 3.92 (m, 1H); 4.18 (m, 1H); 5.55 (d, 1H); 6.19 (t, 1H); 6.91 (d, 1H); 7.29 (d, 1H); 7.80 (s, 1H); 11.63 (s, 1H) ppm.

11. substituted 1-(2'-deoxy-β-D-threo-pentofuranosyl)-5-(E)-2-bromovinyl)-2,4-(1H, 3H)-pyrimidinedione

11.1 1-(5'-iodo-2',5'-dideoxy-β-D-threo-pentofuranosyl)-5-(E)-(2-bromovinyl)-2,4-(1H,3H)-pyrimidinedione

11.1.1. 1-(2'-deoxy-β-D-threo-pentofuranosyl)-5-(E)-(2-bromovinyl)-2,4-(1H,3H)-pyrimidinedione 15.8 g (37.6 mmol) 2,3'-anhydro-5'-O-benzoyl-2'-deoxy-5-(E)-bromovinyluridine are heated with 65.7 ml (132 mmol, 3.5 eq.) 2 M sodium hydroxide solution in 600 ml of a mixture of ethanol/water (5/1) for 1 h at reflux. After cooling of the reaction mixture to room temperature, this is neutralised with concentrated hydrochloric acid and subsequently the solvent is removed on the rotary evaporator. Purification by column chromatography (acetic ester/methanol, 9/1 and chloroform/methanol, 7/1) yields 10.9 g (32.7 mmol, 87%) 1-(2'-deoxy-β-D-threo-pentofuranosyl)-5-(E)-(2-bromovinyl)-2,4-(1H, 3H)-pyrimidinedione as white solid.

11.1.2. 1-(5'-methylsulphonyl-2'-deoxy-β-D-threo-pentofuranosyl)-5-(E)-(2-bromovinyl)-2,4-(1H,3H)-pyrimidinedione 10.9 g (32.7 mmol) 1-(2'-deoxy-β-D-threo-pentofuranosyl)-5-(E)-(2-bromovinyl)-2,4-(1H, 3H)-pyrimidinedione are placed at 0° C. in 100 ml pyridine. 3.94 g (34.4 mmol, 1.05 eq.) methylsulphonylchloride are dissolved in 50 ml THF and added slowly in drops. Subsequently the reaction mixture is agitated for a further 3 h at 0° C. The batch is poured onto 300 g ice, adjusted to pH=5 with concentrated hydrochloric acid and the mixture is extracted with 3×100 ml acetic ester. The combined organic phase is washed with 1 M hydrochloric acid and also NaCl solution, dried with Na$_2$SO$_4$, filtered and the solvent is removed on the rotary evaporator. The result is 11.8 g (28.7 mmol) 1-(5'-methylsulphonyl-2'-deoxy-β-D-threo-pentofuranosyl)-5-(E)-(2-bromovinyl)-2,4-(1H, 3H)-pyrimidinedione as white solid. The crude product is converted without further purification.

11.1.3. 1-(5'-iodo-2',5'-dideoxy-β-D-threo-pentofuranosyl)-5-(E)-(2-bromovinyl)-2,4-(1H, 3H)-pyrimidinedione 0.50 g (1.22 mmol) 1-(5'-methylsulphonyl-2'-deoxy-β-D-threo-pentofuranosyl)-5-(E)-(2-bromovinyl)-2,4-(1H,3H)-pyrimidinedione are heated with 911 mg (6.08 mmol, 5.0 eq.) sodium iodide in 10 ml DMF for 20 h. The reaction mixture is absorbed in 50 ml acetic ester, washed with water and NaCl solution, dried with Na$_2$SO$_4$, filtered and the solvent is removed on the rotary evaporator. Purification by column chromatography (chloroform/methanol, 9/1) yields 130 mg (293 μmol, 24%) 1-(5'-iodo-2',5'-dideoxy-β-D-threo-pentofuranosyl)-5-(E)-(2-bromovinyl)-2,4-(1H, 3H)-pyrimidinedione as a faintly yellowish solid with a melting point of 79-81° C.

$^1$H-NMR (500 MHz, DMSO-$d_6$): 2.04 (d, 1H); 2.58 (m, 1H); 3.43-3.53 (m, 2H); 4.16 (m, 1H); 4.26 (m, 1H); 5.44 (d, 1H); 6.06 (dd, 1H); 6.93 (d, 1H); 7.24 (d, 1H); 7.98 (s, 1H); 11.57 (s, 1H) ppm.

12. 1-(2',3-didehydro-2'-deoxy-2'-fluoro-β-D-arabinofuranosyl)-5-ethyluracil

12.1. 1-(2'-deoxy-2'-fluoro-5'-O-trityl-β-D-arabinofuranosyl)-5-ethyluracil 22.8 g (83.2 mmol) 1-(2'-deoxy-2'-fluoro-β-D-arabinofuranosyl)-5-ethyluracil are suspended in 200 ml pyridine and 25.5 g (91.6 mmol) tritylchloride are added. The reaction mixture is agitated for 24 h at room temperature and subsequently the solvent is removed on the rotary evaporator. The residue is absorbed in 300 ml acetic ester and washed with diluted hydrochloric acid, NaHCO$_3$ solution and NaCl solution. The organic phase is dried with Na$_2$SO$_4$, filtered and the solvent is removed on the rotary evaporator. Purification by column chromatography (chloroform/methanol, 9/1) yields 26.1 g (50.5 mmol, 61%) 1-(2'-deoxy-2'-fluoro-5'-O-trityl-β-D-arabinofuranosyl)-5-ethyluracil as white solid.

12.2. 2,3'-anhydro-1-(2'-deoxy-2'-fluoro-5'-O-trityl-β-D-arabinofuranosyl)-5-ethyluracil 26.1 g (50.5 mmol) 1-(2'-deoxy-2'-fluoro-5'-O-trityl-β-D-arabinofuranosyl)-5-ethyluracil are placed in 300 ml DMF and 19.9 g (75.7 mmol) PPH$_3$ are added. Subsequently 15.3 g (75.7 mmol) diisopropylazodicarboxylate are dissolved in 50 ml DMF and added in drops. After two hours the solvent is removed on the rotary evaporator, the residue is absorbed in 1 l diethylether and agitated vigorously for 16 h. The resulting solid is suctioned off and washed three times with 50 ml diethylether. Recrystallisation from cyclohexane/acetic ester yields 25.5 g (50.5 mmol, 100%) of 2,3'-anhydro-1-(2'-deoxy-2'-fluoro-5'-O-trityl-β-D-arabinofuranosyl)-5-ethyluracil as white solid.

12.3. 1-(2',3'-didehydro-2'-deoxy-2'-fluoro-5'-O-trityl-β-D-arabinofuranosyl)-5-ethyluracil 25.5 g (50.5 mmol) 2,3'-anhydro-1-(2'-deoxy-2'-fluoro-5'-O-trityl-β-D-arabinofuranosyl)-5-ethyluracil are dissolved in 600 ml ethanol, 125 ml water and 62.5 ml (126 mmol) 2 M NaOH solution are added and the reaction mixture is heated for 2 h under reflux. The ethanol is removed extensively on the rotary evaporator. The residue is neutralised with diluted hydrochloric acid and extracted with acetic ester. The combined organic phases are washed with NaCl solution, dried with Na$_2$SO$_4$, filtered and the solvent is removed on the rotary evaporator. Purification by column chromatography (chloroform/methanol, 95/5) yields 19.6 g (39.2 mmol, 78%) 1-(2',3'-didehydro-2'-deoxy-2'-fluoro-5'-O-trityl-β-D-arabinofuranosyl)-5-ethyluracil as white solid.

12.4 1-(2',3'-didehydro-2'-deoxy-2'-fluoro-β-D-arabinofuranosyl)-5-ethyluracil 5.00 g (10.0 mmol) 1-(2',3'-didehydro-2'-deoxy-2'-fluoro-5'-O-trityl-β-D-arabinofuranosyl)-5-ethyluracil are dissolved in 50 ml dioxane and cooled to 0° C. 4.2 ml (20.0 mmol) 4.8 M HCl in dioxane are added slowly in drops. The cooling bath is removed and the reaction mixture is agitated for 2 h. Subsequently the solvent is removed on the rotary evaporator. Purification by column chromatography (chloroform/methanol, 9/1) yields 2.06 g (8.04 mmol, 80%) 1-(2',3'-didehydro-2'-deoxy-2'-fluoro-β-D-arabinofuranosyl)-5-ethyluracil as white solid with a melting point of 145-146° C.

$^1$H-NMR (300 MHz, DMSO-d$_6$): 1.02 (t, 3H); 2.20 (q, 2H); 3.55-3.65 (m, 2H); 4.76-4.84 (m, 1H); 5.16 (t, 1H); 5.95-6.05 (m, 1H); 6.75-6.80 (m, 1H); 7.86 (s, 1H); 11.42 (s, 1H).

FIG. 9 shows the results of 5'-bromo-2',5'-dideoxy-5-(E)-bromovinyluridine in combination with mitomycin C (MMC) in comparison with MMC alone and MMC in combination with BVDU.

FIG. 10 shows the results of 5'-azido-2',5'-dideoxy-5-(E)-bromovinyluridine in combination with mitomycin C (MMC) in comparison with MMC alone and MMC in combination with BVDU.

FIG. 11 shows the results of 1-(3' azido-2',3'-dideoxy-β-D-erythro-pentofuranosyl)-5-(E)-(2-bromovinyl)-2,4(1H,3H) pyrimidinedione in combination with mitomycin C (MMC) in comparison with MMC alone and MMC in combination with BVDU.

FIG. 12 shows the results of 3'-Cl-BVDU in combination with mitomycin C (MMC) in comparison with MMC alone and MMC in combination with BVDU.

Figure 1:
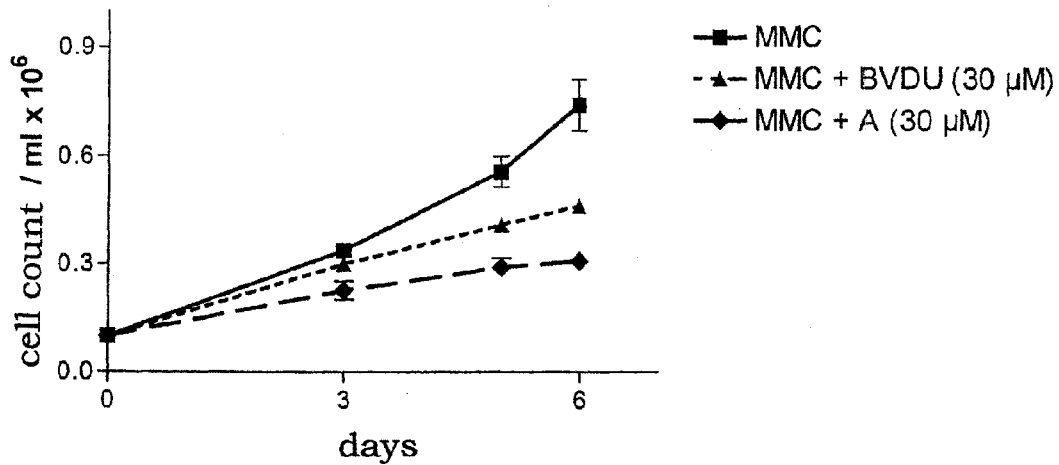
Figure 2:
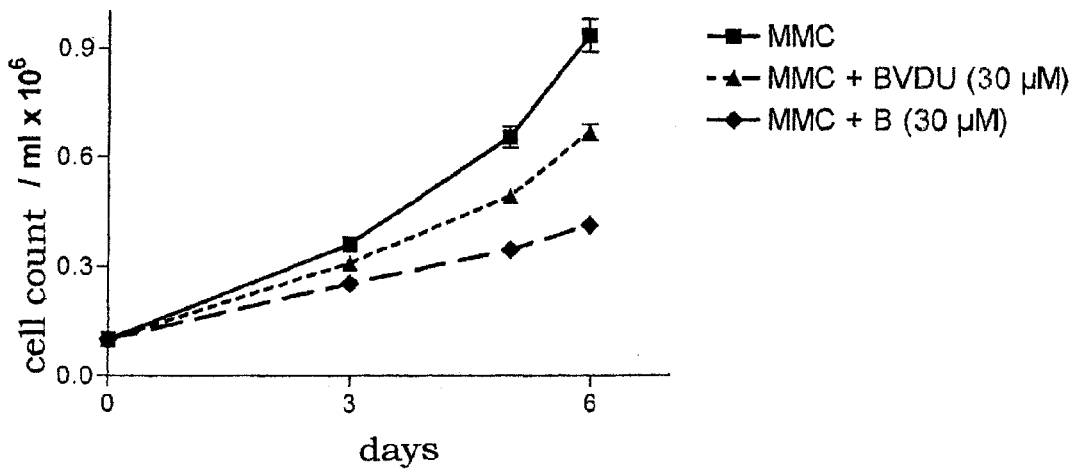
Figure 3:
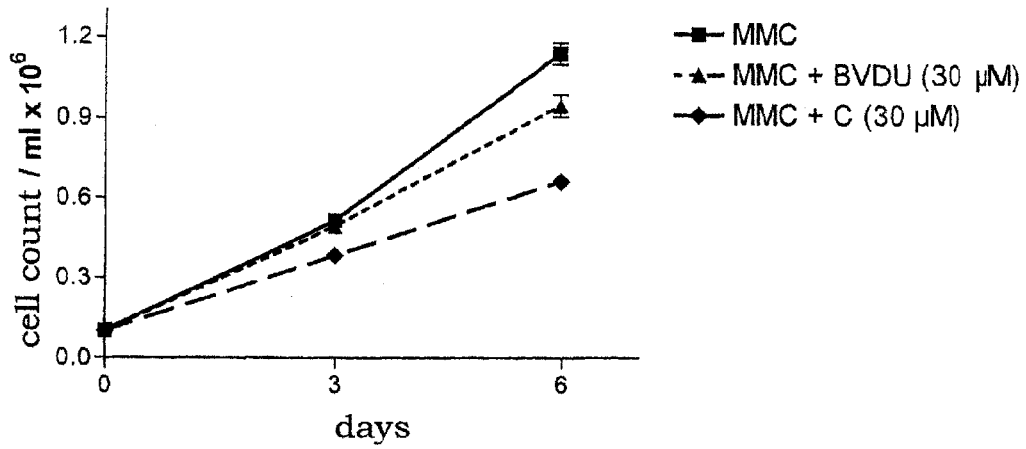
Figure 4:
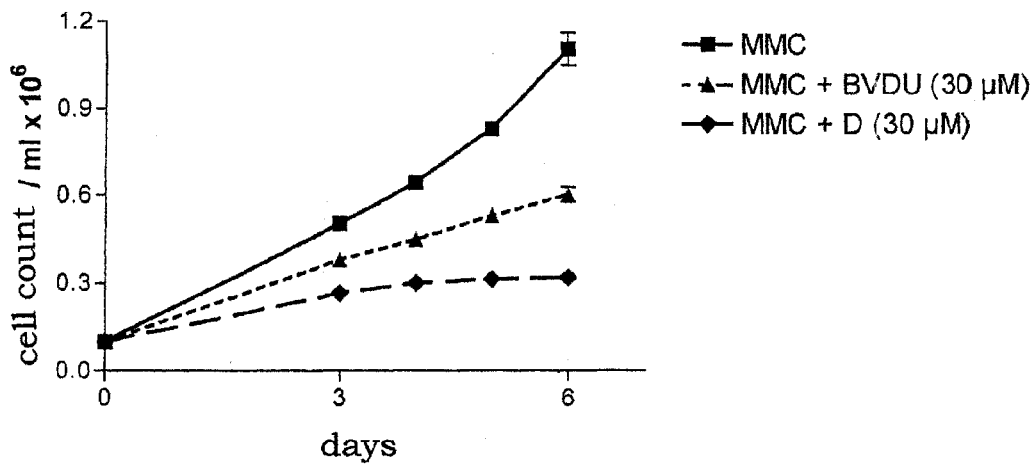
Figure 5:
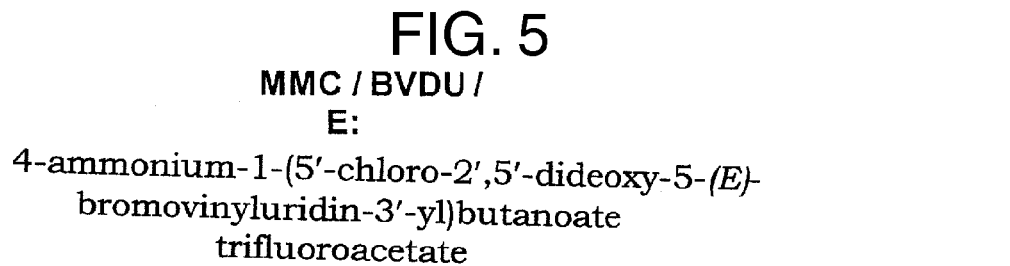
Figure 6:
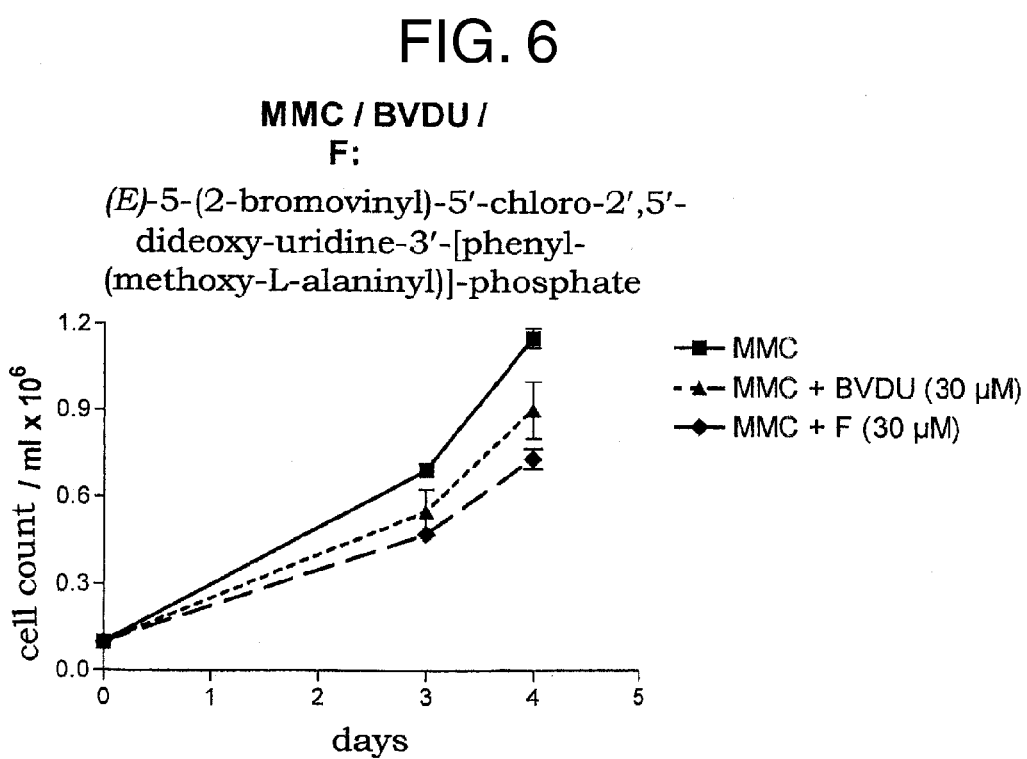
Figure 7:
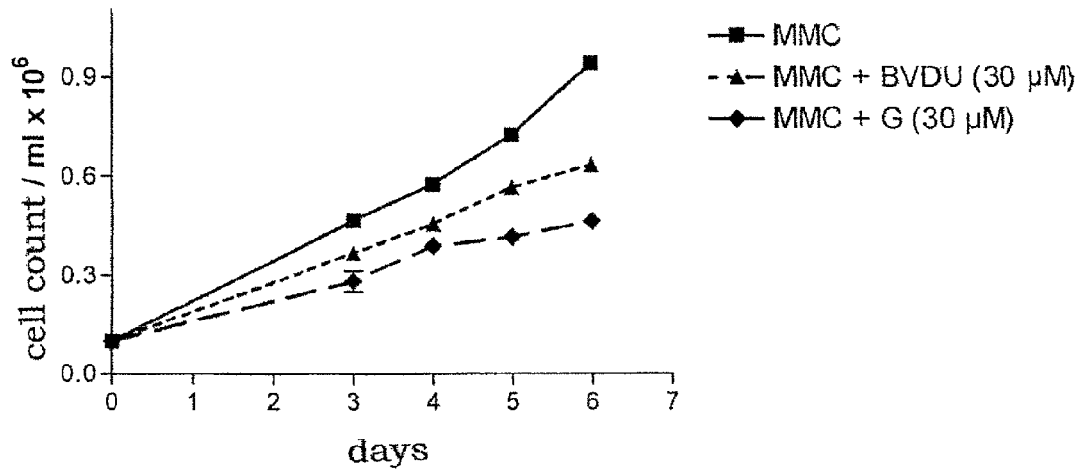
Figure 8:
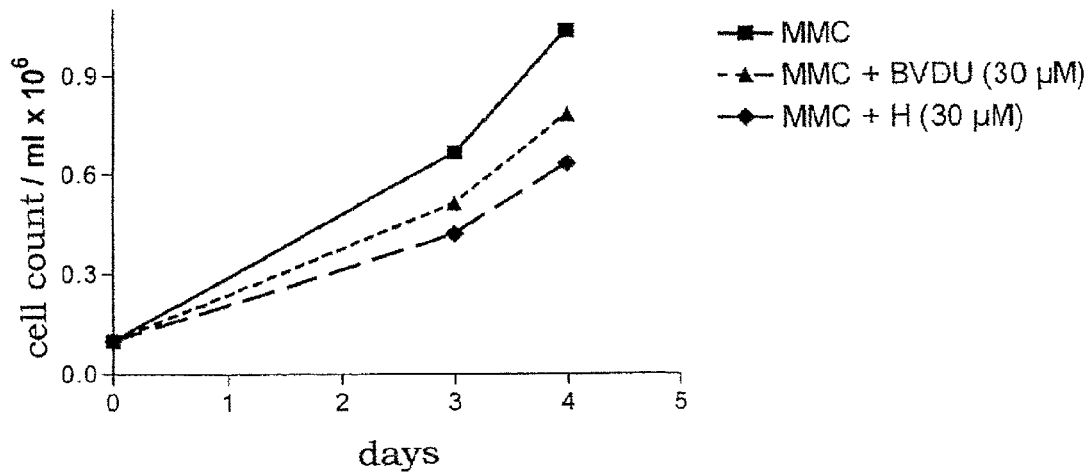
Figure 9:
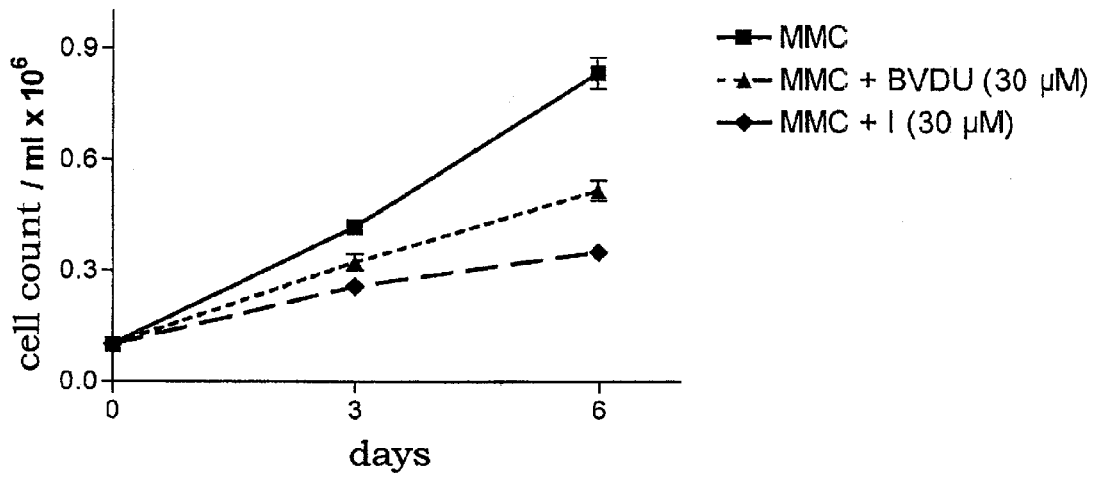
FIGS. 9 to 12 show the results of further compounds according to the invention.
Figure 10:
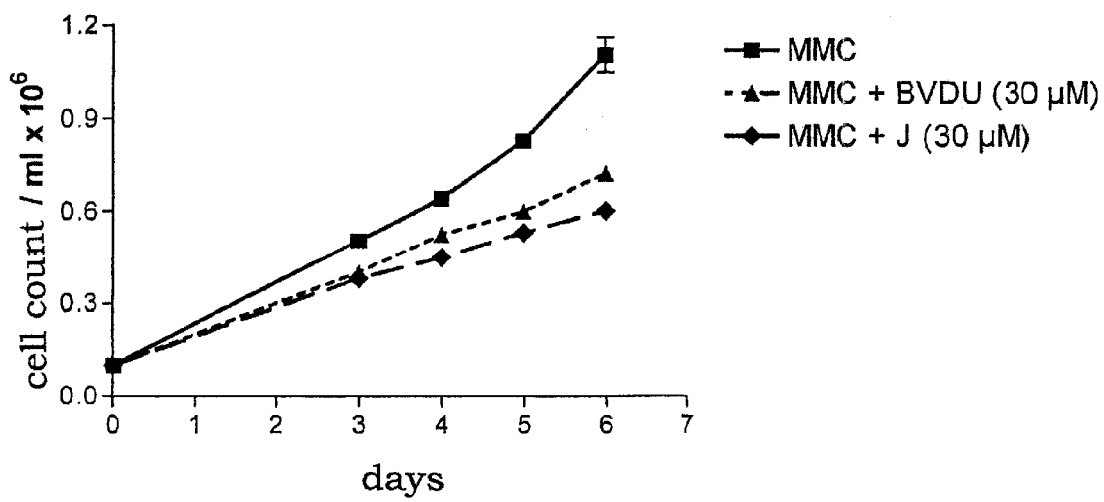
Figure 11:
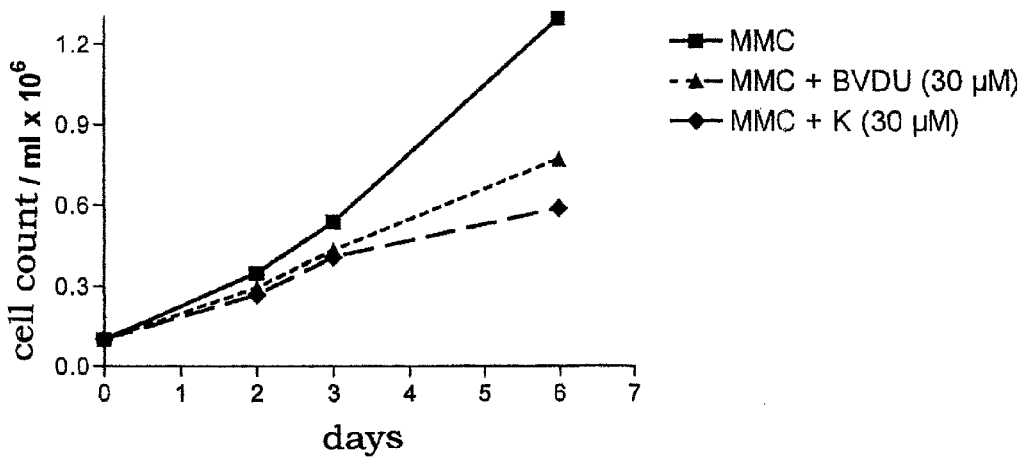
Figure 12:
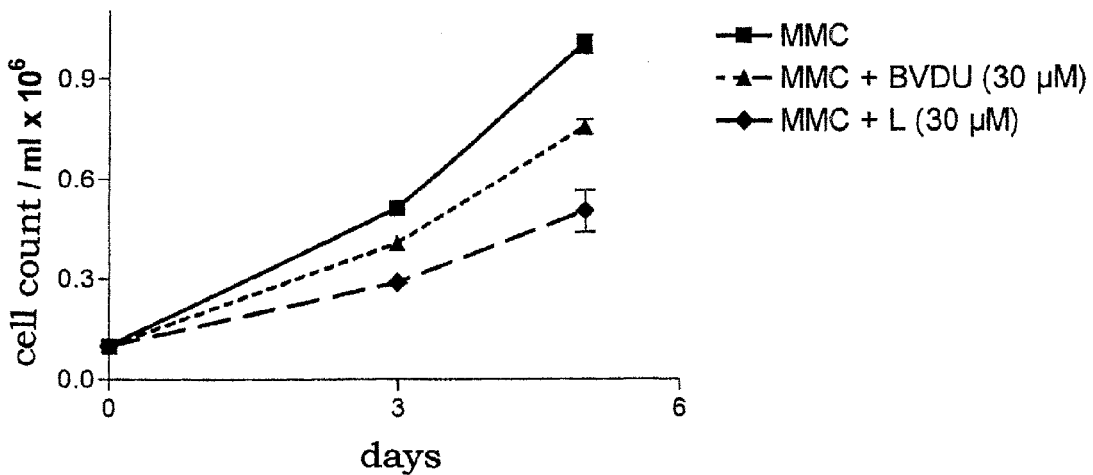

The invention claimed is:
1. A nucleoside of the general formula I

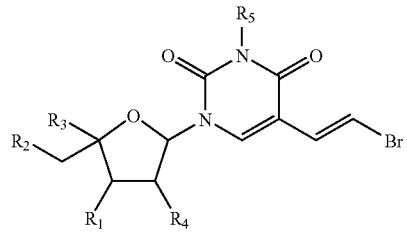

wherein
$R_1$=halogen, $R_2$ is selected from the group consisting of H, halogen, OR$_8$, CN, N$_3$, and NR$_6$R$_7$,
$R_3$=H, straight-chain or branched C$_1$-C$_8$ alkyl, or straight-chain or branched C$_2$-C$_8$ alkylene,
$R_4$=H, halogen, OR$_8$, N$_3$, or NR$_6$R$_7$, or R$_4$ together with R$_1$ represent a second bond between the C-atoms adjacent to R$_1$ and R$_4$,
$R_5$=H, C$_1$-C$_8$ alkyl or aryl,
$R_6$ and $R_7$, independently of each other, are H, straight-chain or branched C$_1$-C$_8$ alkyl or acetyl, and R$_8$ is a straight-chain or branched C$_1$-C$_8$ alkyl.

2. The nucleoside according to claim 1, which is of the general formula V

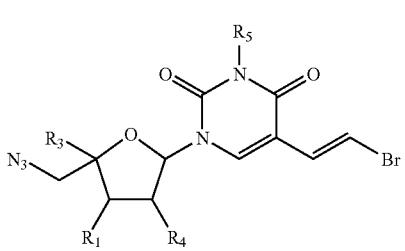

wherein
$R_1$=halogen,
$R_3$=H, straight-chain or branched C$_1$-C$_8$ alkyl, or straight-chain or branched C$_2$-C$_8$ alkylene,
$R_4$=H, halogen, OR$_8$, N$_3$ or NR$_6$R$_7$,
$R_5$=H, C$_1$-C$_8$ alkyl or aryl,
$R_6$ and $R_7$, independently of each other, are H, straight-chain or branched C$_1$-C$_8$ alkyl or acetyl, and R$_8$ is a straight-chain or branched C$_1$-C$_8$ alkyl.

3. The nucleoside according to claim 1, which is of the general formula VI

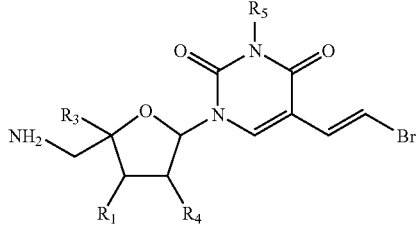

having $R_1$=halogen, $R_3$=H, straight-chain or branched $C_1$-$C_8$ alkyl, or straight-chain or branched $C_2$-$C_8$ alkylene, $R_4$=H, halogen, $OR_8$, $N_3$ or $NR_6R_7$, $R_5$=H, $C_1$-$C_8$ alkyl or aryl, $R_6$ and $R_7$, independently of each other, are H, straight-chain or branched $C_1$-$C_8$ alkyl or acetyl, and $R_8$ is a straight-chain or branched $C_1$-$C_8$ alkyl.

4. The nucleoside according to claim 1, which is of the general formula VII:

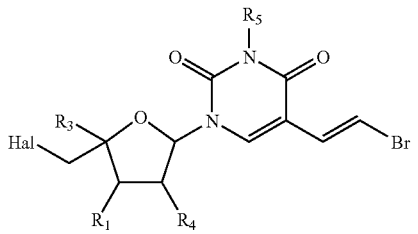

wherein $R_1$=halogen, $R_3$=H, straight-chain or branched $C_1$-$C_8$ alkyl, or straight-chain or branched $C_2$-$C_8$ alkylene, $R_4$=H, halogen, $OR_8$, $N_3$ or $NR_6R_7$, $R_5$=H, $C_1$-$C_8$ alkyl or aryl, $R_6$ and $R_7$, independently of each other, are H, straight-chain or branched $C_1$-$C_8$ alkyl or acetyl, and $R_8$ is a straight-chain or branched $C_1$-$C_8$ alkyl, wherein Hal represents a halogen.

5. A nucleoside of the formula VIII:

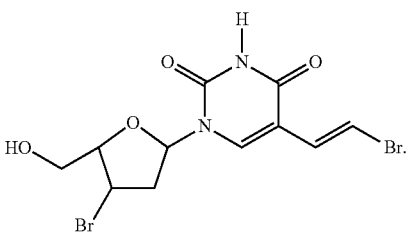

6. The nucleoside according to claim 1, which is of the formula X:

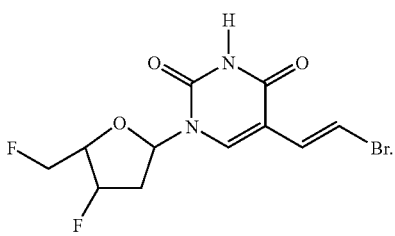

7. The nucleoside according to claim 1, which is of the formula XI:

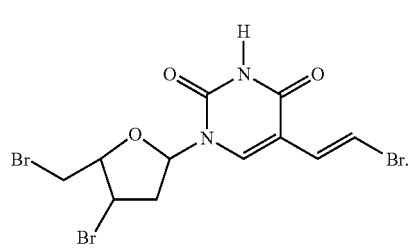

8. A nucleoside of the formula XII, XIII, XIV, or XV:

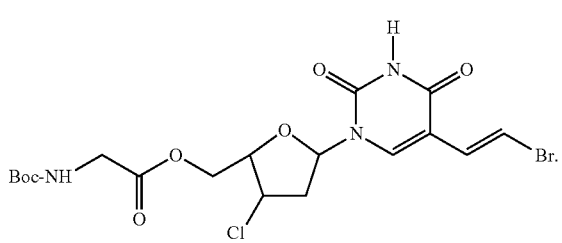

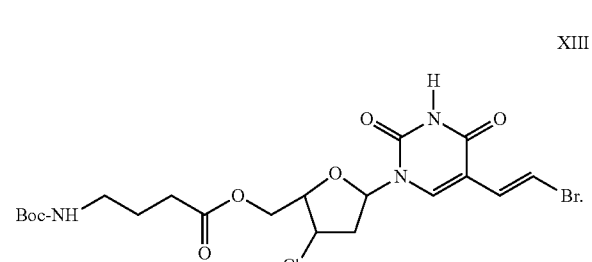

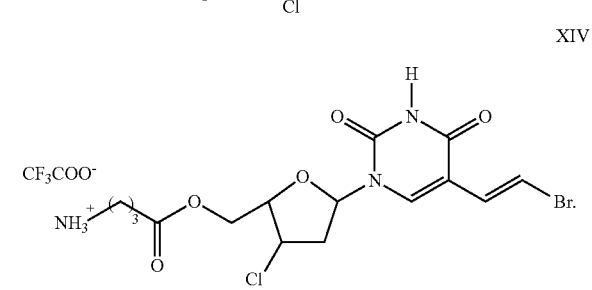

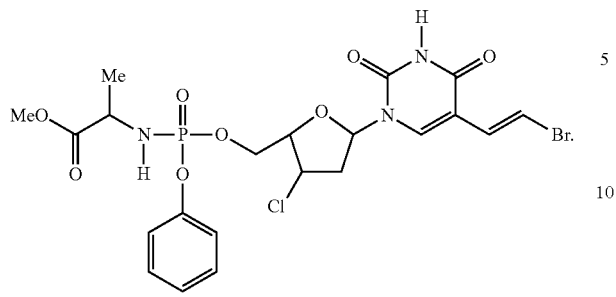

XV

9. A pharmaceutical composition comprising at least one nucleoside according to claim 1 and a pharmaceutically acceptable carrier.

10. The pharmaceutical composition according to claim 9, which further contains at least one cytostatic agent.

11. A pharmaceutical composition comprising at least one nucleoside according to claim 8 and a pharmaceutically acceptable carrier.

12. The pharmaceutical composition according to claim 11, which further contains at least one cytostatic agent.

13. A pharmaceutical composition comprising the nucleoside according to claim 5 and a pharmaceutically acceptable carrier.

14. The pharmaceutical composition according to claim 13, which further contains at least one cytostatic agent.

* * * * *

UNITED STATES PATENT AND TRADEMARK OFFICE
CERTIFICATE OF CORRECTION

PATENT NO. : 8,492,537 B2
APPLICATION NO. : 12/377239
DATED : July 23, 2013
INVENTOR(S) : Fahrig et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 728 days.

Signed and Sealed this
Eighth Day of September, 2015

Michelle K. Lee
*Director of the United States Patent and Trademark Office*